(12) United States Patent
Sato et al.

(10) Patent No.: US 11,390,860 B2
(45) Date of Patent: Jul. 19, 2022

(54) SET OF POLYPEPTIDES EXHIBITING NUCLEASE ACTIVITY OR NICKASE ACTIVITY WITH DEPENDENCE ON LIGHT OR IN PRESENCE OF DRUG OR SUPPRESSING OR ACTIVATING EXPRESSION OF TARGET GENE

(71) Applicant: The University of Tokyo, Tokyo (JP)

(72) Inventors: Moritoshi Sato, Tokyo (JP); Yuta Nihongaki, Tokyo (JP)

(73) Assignee: The University of Tokyo, Tokyo (JP)

(*) Notice: Subject to any disclaimer, the term of this patent is extended or adjusted under 35 U.S.C. 154(b) by 0 days.

(21) Appl. No.: 15/515,750

(22) PCT Filed: Apr. 13, 2016

(86) PCT No.: PCT/JP2016/061949
§ 371 (c)(1),
(2) Date: Mar. 30, 2017

(87) PCT Pub. No.: WO2016/167300
PCT Pub. Date: Oct. 20, 2016

(65) Prior Publication Data
US 2017/0298330 A1    Oct. 19, 2017

(30) Foreign Application Priority Data
Apr. 13, 2015   (JP) .............................. JP2015-082012

(51) Int. Cl.
| | | |
|---|---|---|
| *C12N 9/22* | (2006.01) | |
| *C12N 15/90* | (2006.01) | |
| *C07K 14/37* | (2006.01) | |
| *C07K 14/415* | (2006.01) | |
| *C07K 14/47* | (2006.01) | |
| *C12N 9/90* | (2006.01) | |
| *C12N 13/00* | (2006.01) | |
| *C12N 15/63* | (2006.01) | |
| *C12N 15/113* | (2010.01) | |

(52) U.S. Cl.
CPC .............. *C12N 9/22* (2013.01); *C07K 14/37* (2013.01); *C07K 14/415* (2013.01); *C07K 14/4728* (2013.01); *C12N 9/90* (2013.01); *C12N 13/00* (2013.01); *C12N 15/63* (2013.01); *C12N 15/90* (2013.01); *C12N 15/907* (2013.01); *C12Y 502/01008* (2013.01); *C07K 2319/00* (2013.01); *C07K 2319/09* (2013.01); *C12N 15/113* (2013.01); *C12N 2310/20* (2017.05)

(58) Field of Classification Search
None
See application file for complete search history.

(56) References Cited

U.S. PATENT DOCUMENTS

| | | | |
|---|---|---|---|
| 9,839,698 B2* | 12/2017 | Yang | C12N 15/85 |
| 10,266,850 B2* | 4/2019 | Doudna | C12N 15/902 |
| 2015/0291966 A1 | 10/2015 | Zhang et al. | |
| 2016/0177278 A1* | 6/2016 | Wolfe | C12N 9/22 |
| | | | 435/199 |
| 2016/0186208 A1 | 6/2016 | Jaenisch | |
| 2016/0272999 A1 | 9/2016 | Duchateau | |
| 2017/0369891 A1 | 12/2017 | Ge | |
| 2018/0073002 A1 | 3/2018 | Deiters | |

FOREIGN PATENT DOCUMENTS

| | | |
|---|---|---|
| EP | 2682469 A1 | 1/2014 |
| JP | 2015065776 A | 4/2015 |
| WO | 2014018423 A | 1/2014 |
| WO | 2014172470 A2 | 10/2014 |
| WO | 2014191128 A1 | 12/2014 |
| WO | 2016100272 A1 | 6/2016 |
| WO | 2016164797 A1 | 10/2016 |

OTHER PUBLICATIONS

DeRose et al., "Manipulating signaling at will: chemically-inducible dimerization (CID) techniques resolve problems in cell biology" 465(3) Pflugers Archive—European Journal of Physiology 409-417 (Year: 2013).*
Cong, et al., "Multiplex Genome Engineering Using CRISPR/Cas Systems", Jan. 3, 2013, pp. 819-823, vol. 339, Publisher: Science.
International Search Report received in PCT/JP2016/061949, dated Jul. 5, 2016.
Jinek, et al., "RNA-Programmed Genome Editing in Human Cells", Jan. 29, 2013, p. e00471, vol. 2, Publisher: eLife.
Kwano, et al., "Engineered pairs of distinct photoswitches for optogenetic control of cellular proteins", Feb. 24, 2015, p. 6256, vol. 6, No. 6, Publisher: Nat. Commun.
Mali, et al., "RNA-Guided Human Genome Engineering via Cas9", Jan. 3, 2013, p. 823826, vol. 339, No. 6121, Publisher: Science.
Mali, et al., "CAS9 transcriptional activators for target specificity screening and paired nickases for cooperative genome engineering", Aug. 1, 2013, pp. 833-838 and Suppl., vol. 31, No. 9, Publisher: Nat. Biotechnol.
Mueller, et al., "Multi-Chromatic Control of Mammalian Gene Expression and Signaling", Apr. 26, 2013, p. e124, vol. 41, No. 12, Publisher: Nucleic Acids Research.
Nihongaki, et al., "CRISPR-Cas9-based photoactivatable transcription system", Dec. 1, 2014, pp. 169-174, vol. 22, No. 2, Publisher: Chemistry & Biology.
Nihongaki, et al., "Photoactivatable CRISPR-Cas9 for optogenetic genome editing", Jun. 15, 2015, pp. 755-762, vol. 33, No. 7, Publisher: Nat. Biotechnol.

(Continued)

*Primary Examiner* — Nancy J Leith
(74) *Attorney, Agent, or Firm* — Suzannah K. Sundby, Esq.; Canady + Lortz LLP

(57) ABSTRACT

The present invention provides, for example, a set of two polypeptides exhibiting the nuclease activity with dependence on light or in the presence of a drug, in which an N-terminal side fragment and a C-terminal side fragment of a Cas9 protein are bound to each of two polypeptides which form a dimer with dependence on light or in the presence of a drug.

19 Claims, 23 Drawing Sheets

Specification includes a Sequence Listing.

(56) References Cited

OTHER PUBLICATIONS

Polstein, et al., "A light-inducible CRISPR-Cas9 system for control of endogenous gene activation", Feb. 9, 2015, pp. 198-200, vol. 11, No. 3, Publisher: Nat. Chem. Biol.

Qi, et al., "Repurposing CRISPR as an RNA-guided platform for sequence-specific control of gene expression", Feb. 28, 2013, pp. 1173-1183, vol. 152, No. 5, Publisher: Cell.

Ran, et al., "Double nicking by RNA-guided CRISPR Cas9 for enhanced genome editing specificity", Sep. 12, 2013, pp. 1380-1389, vol. 154, Publisher: Cell.

Toettcher, et al., "The Promise of Optogenetics in Cell Biology: Interrogating Molecular Circuits in Space and Time", Dec. 20, 2010, pp. 35-38, vol. 8, No. 1, Publisher: Nature Methods.

Written Opinion received in PCT/JP2016/061949, dated Jul. 5, 2016.

Zetsche, et al., "A split-Cas9 architecture for inducible genome editing and transcription modulation", Feb. 2, 2015, pp. 139-142 and Suppl., vol. 33, No. 2, Publisher: Nat. Biotechnol.

Wright, et al., "Rational design of a split-Cas9 enzyme complex", Feb. 23, 2015, pp. 2984-2989, vol. 112, No. 10, Publisher: PNAS USA.

\* cited by examiner

[Fig. 1]
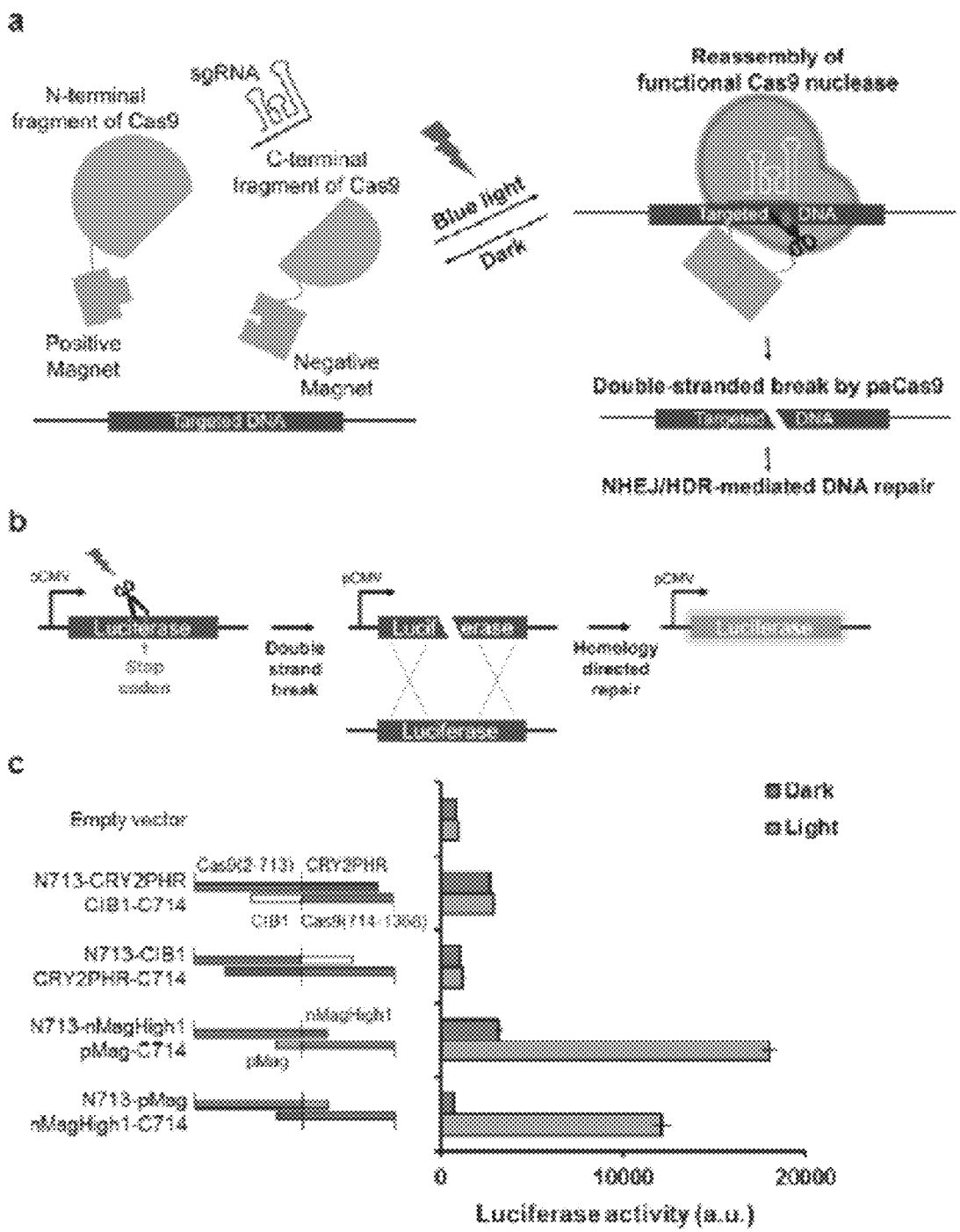

[Fig. 1, cont.]
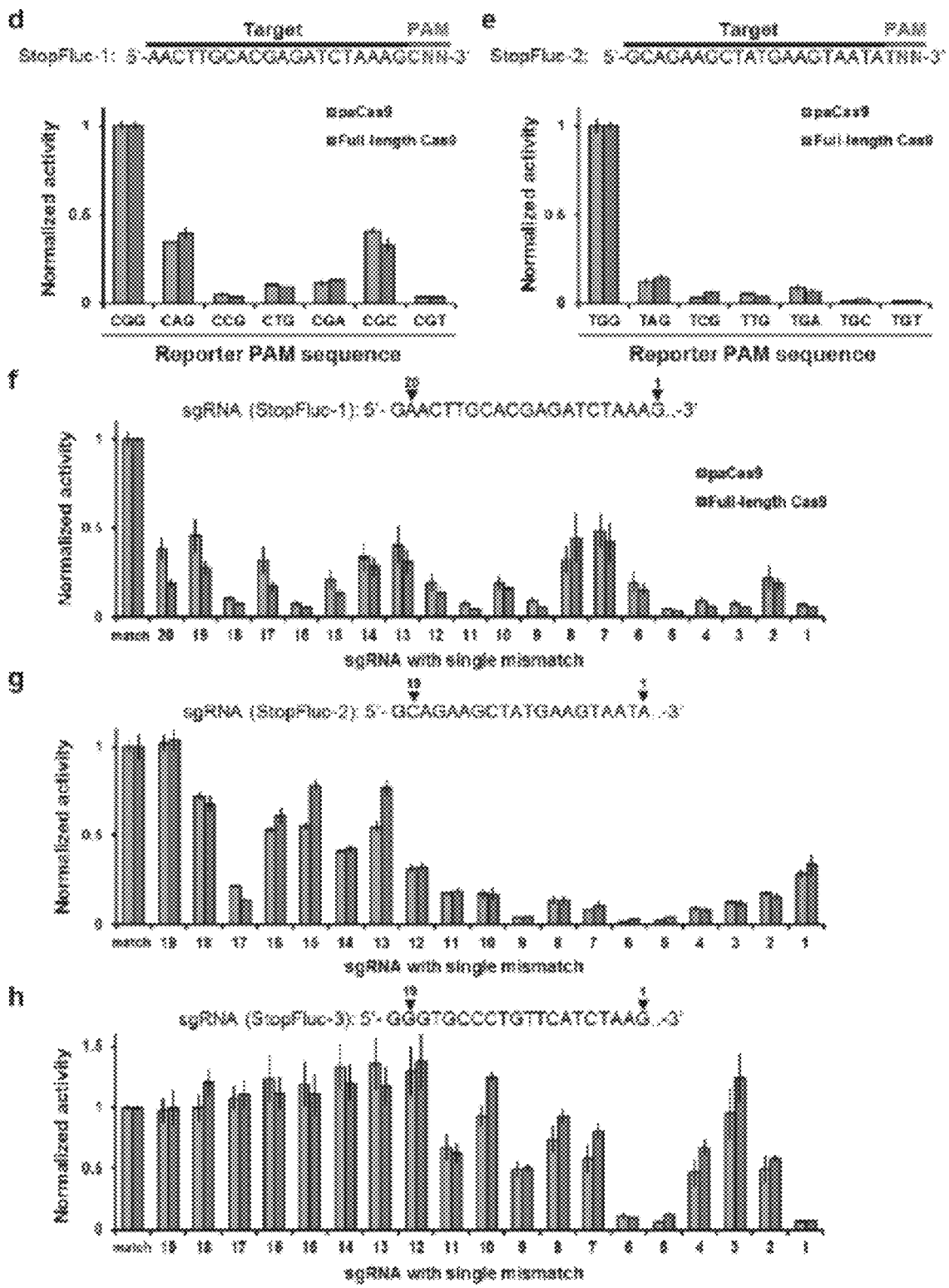

[Fig. 2]
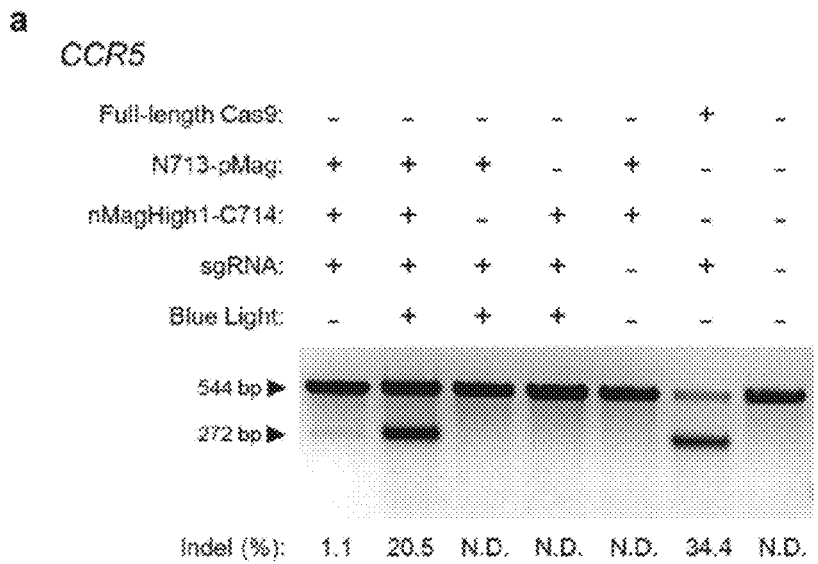
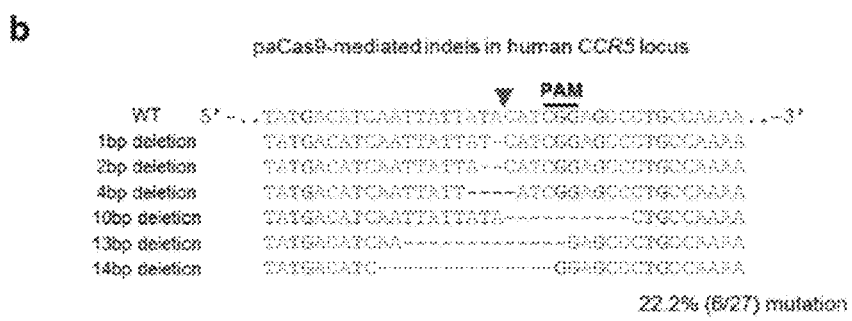
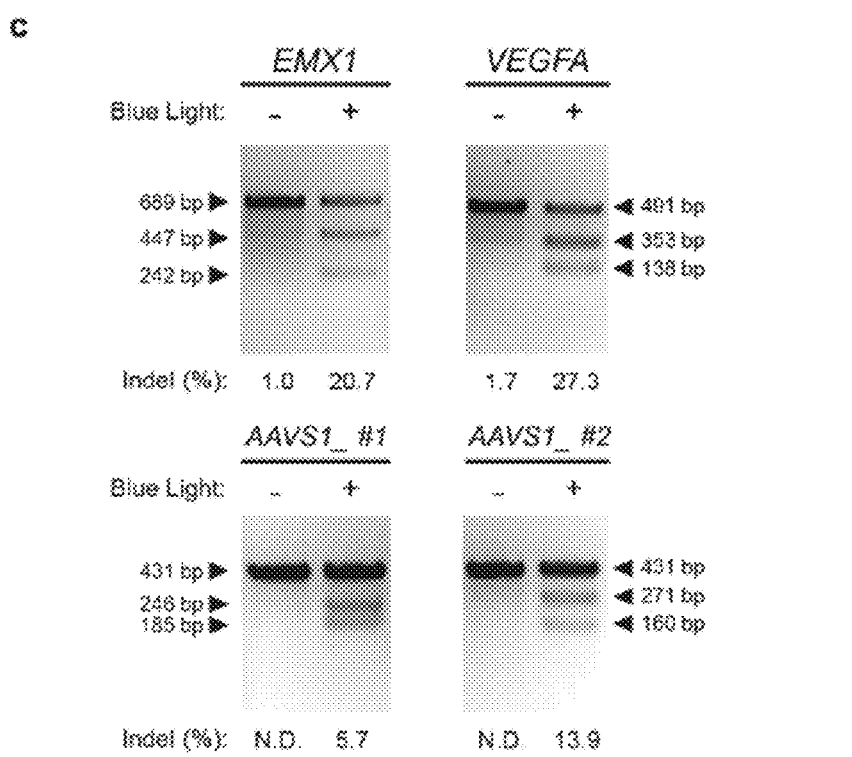

[Fig. 2, cont.]
d
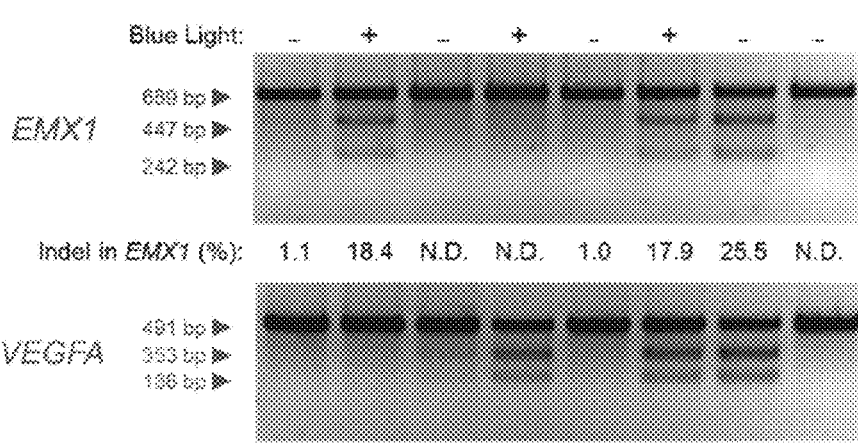
e
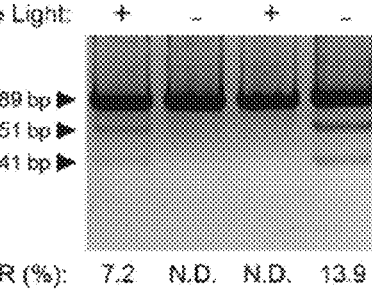

[Fig. 3]
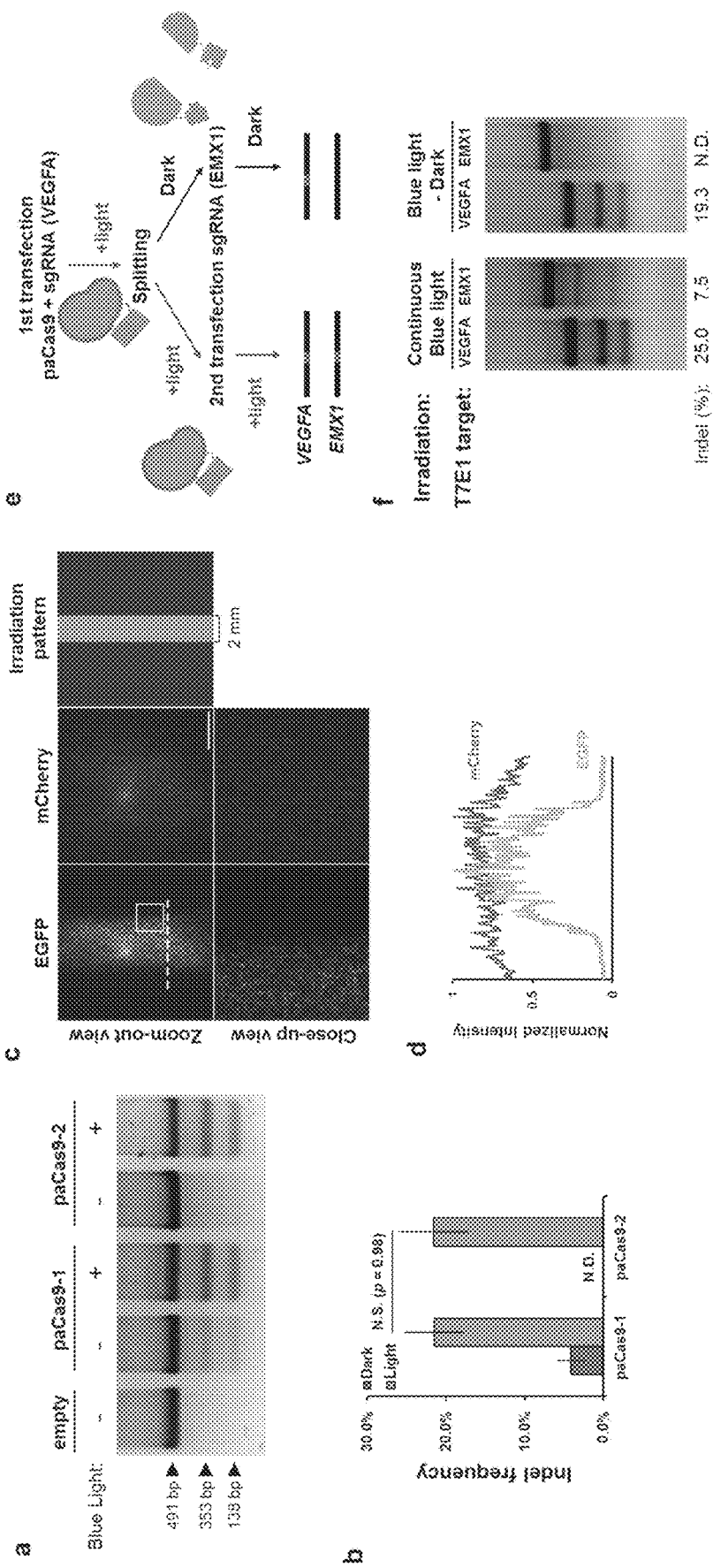

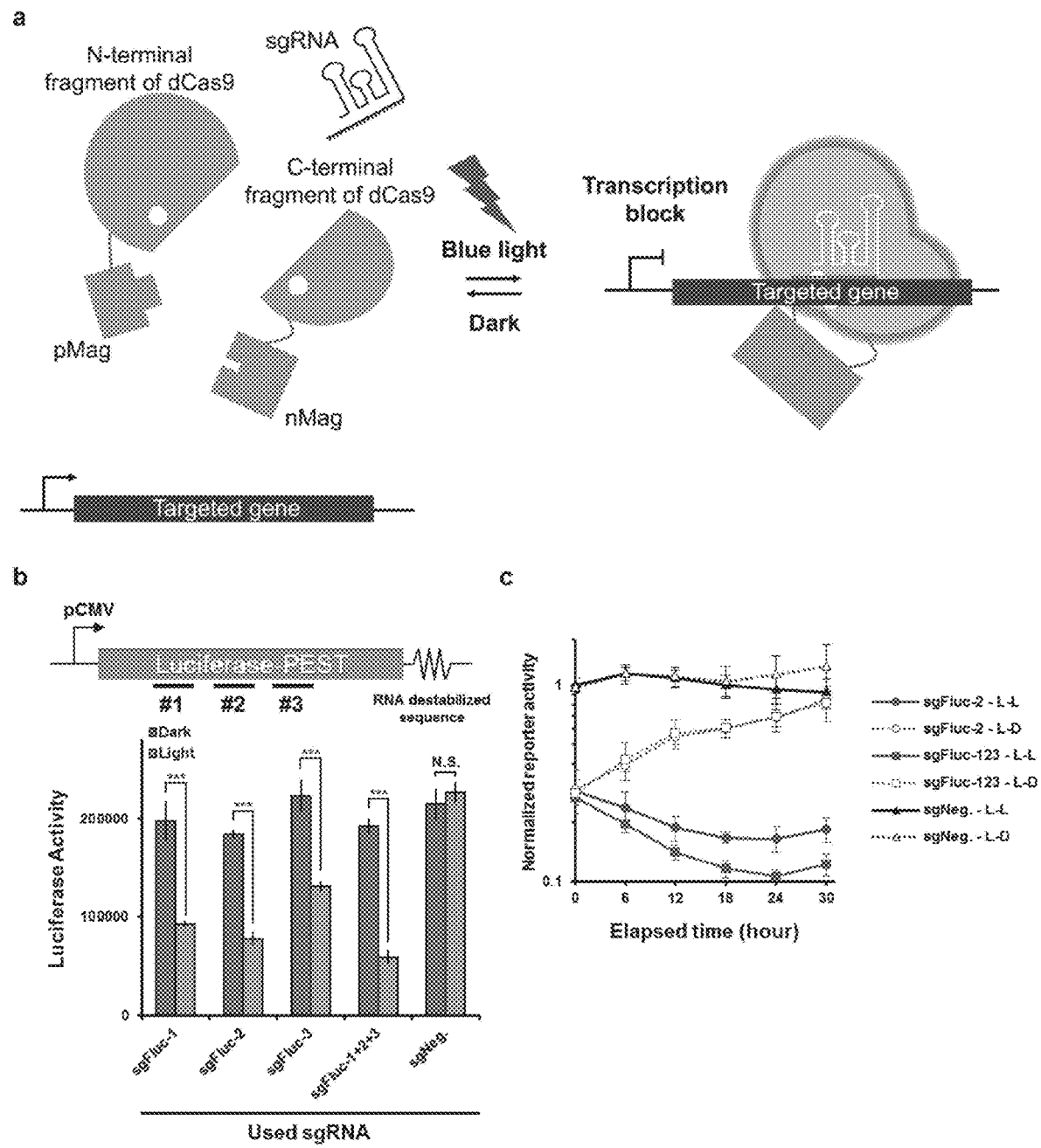
[Fig. 4]

[Fig. 5]
a
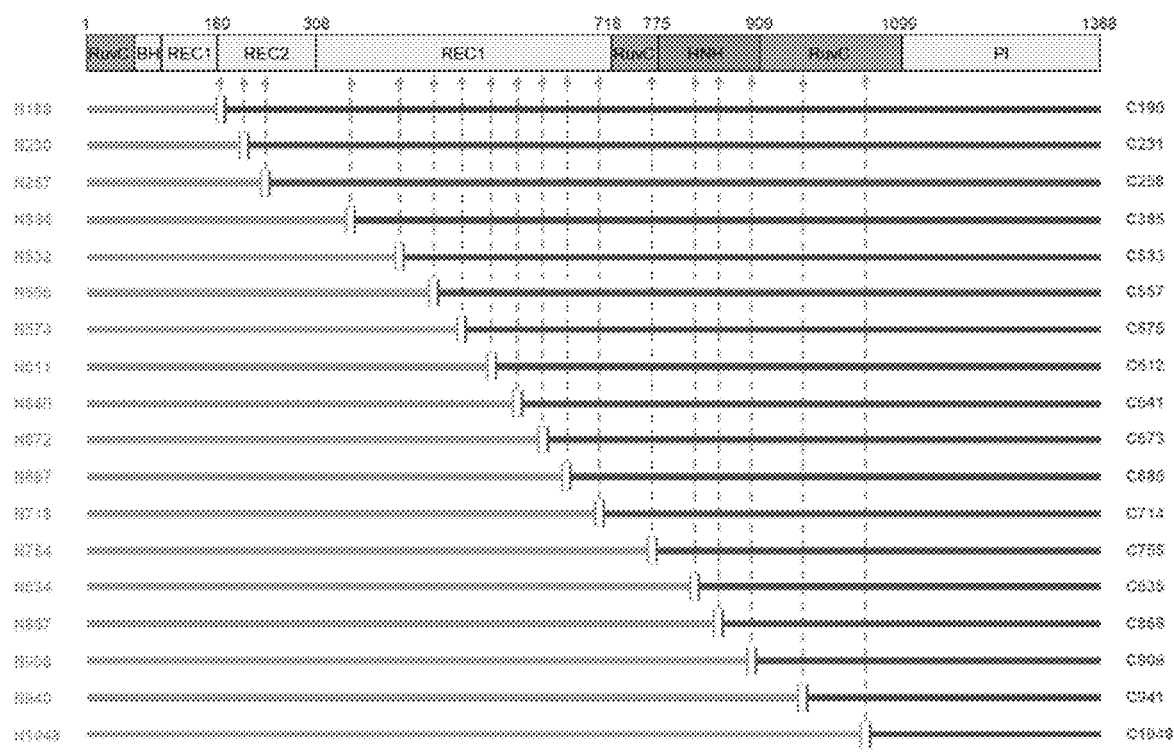
b
N_Cas9-FRB
FKBP-C_Cas9

[Fig. 6]
a
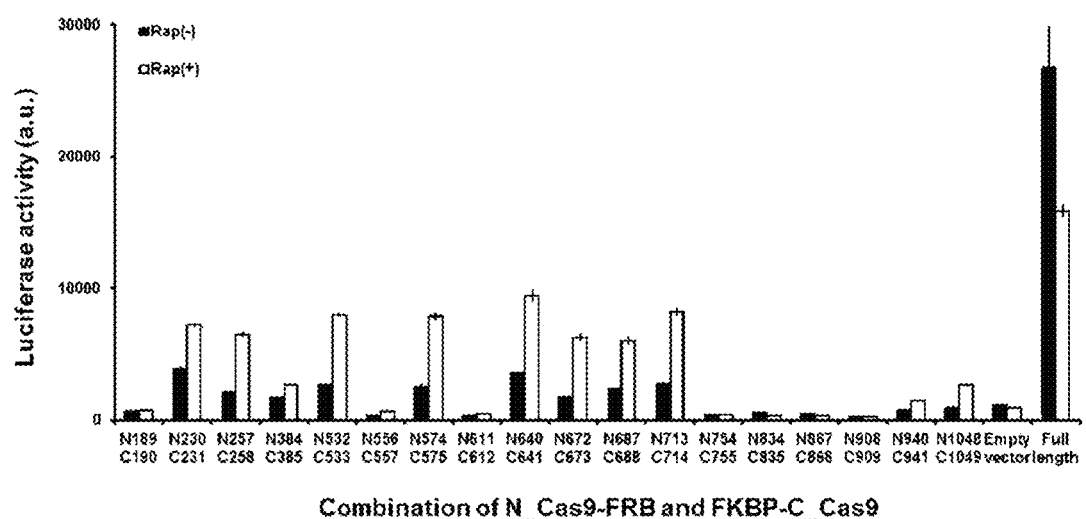
b
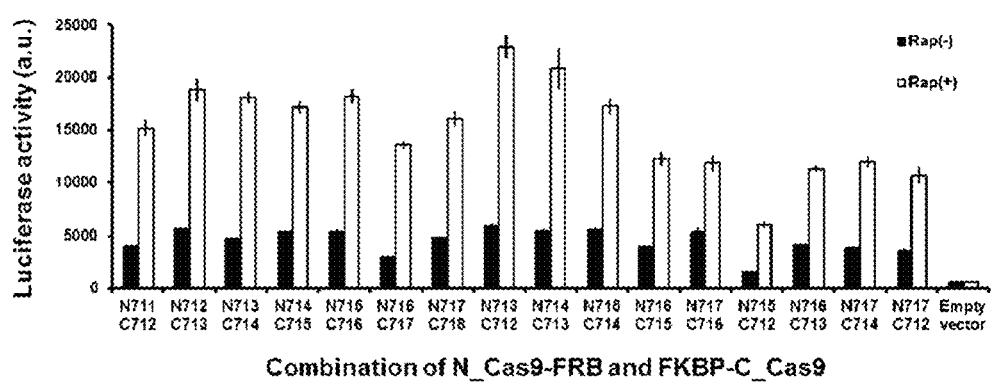

[Fig. 7]
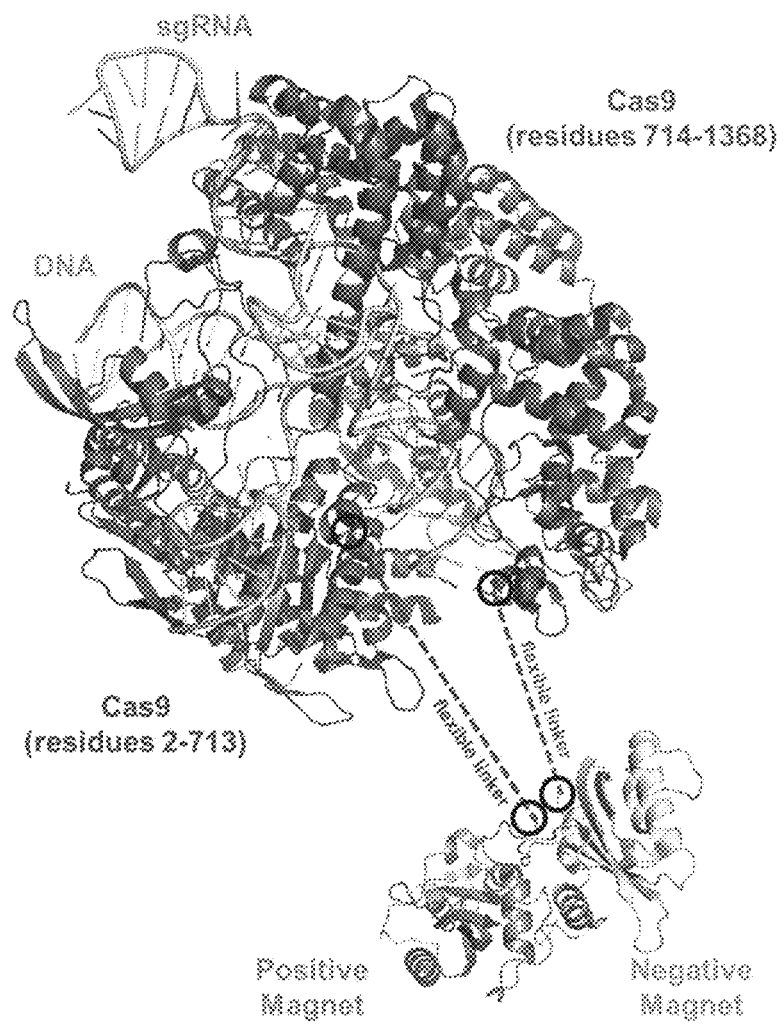

[Fig. 8]
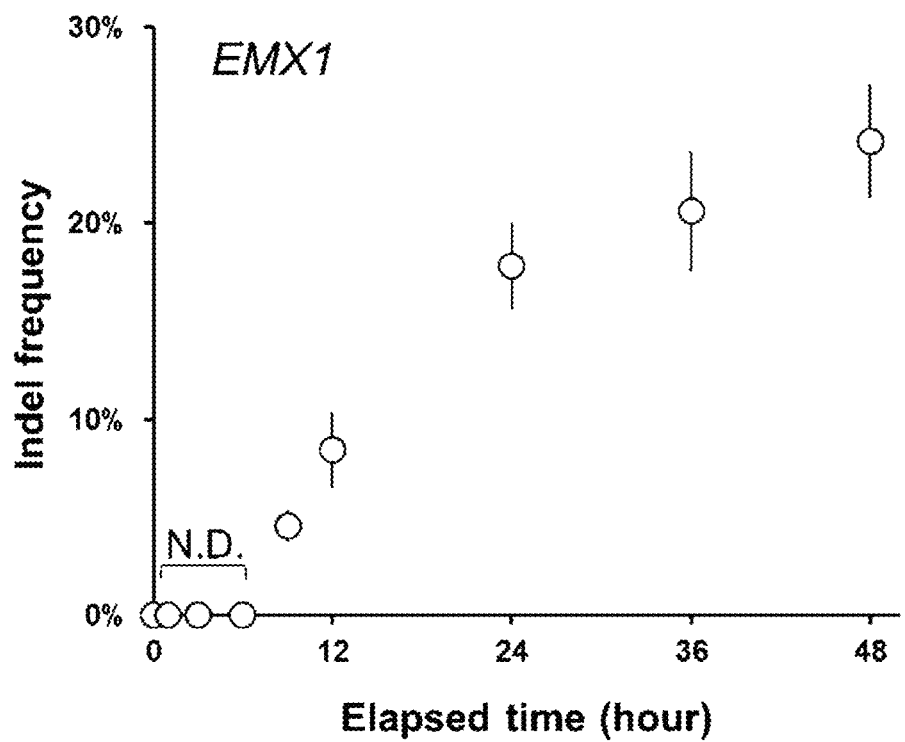
[Fig. 9]
*EMX1*
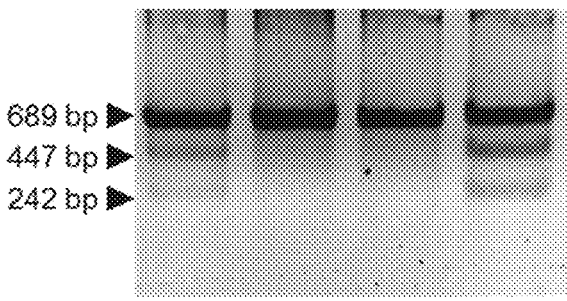

[Fig. 10]
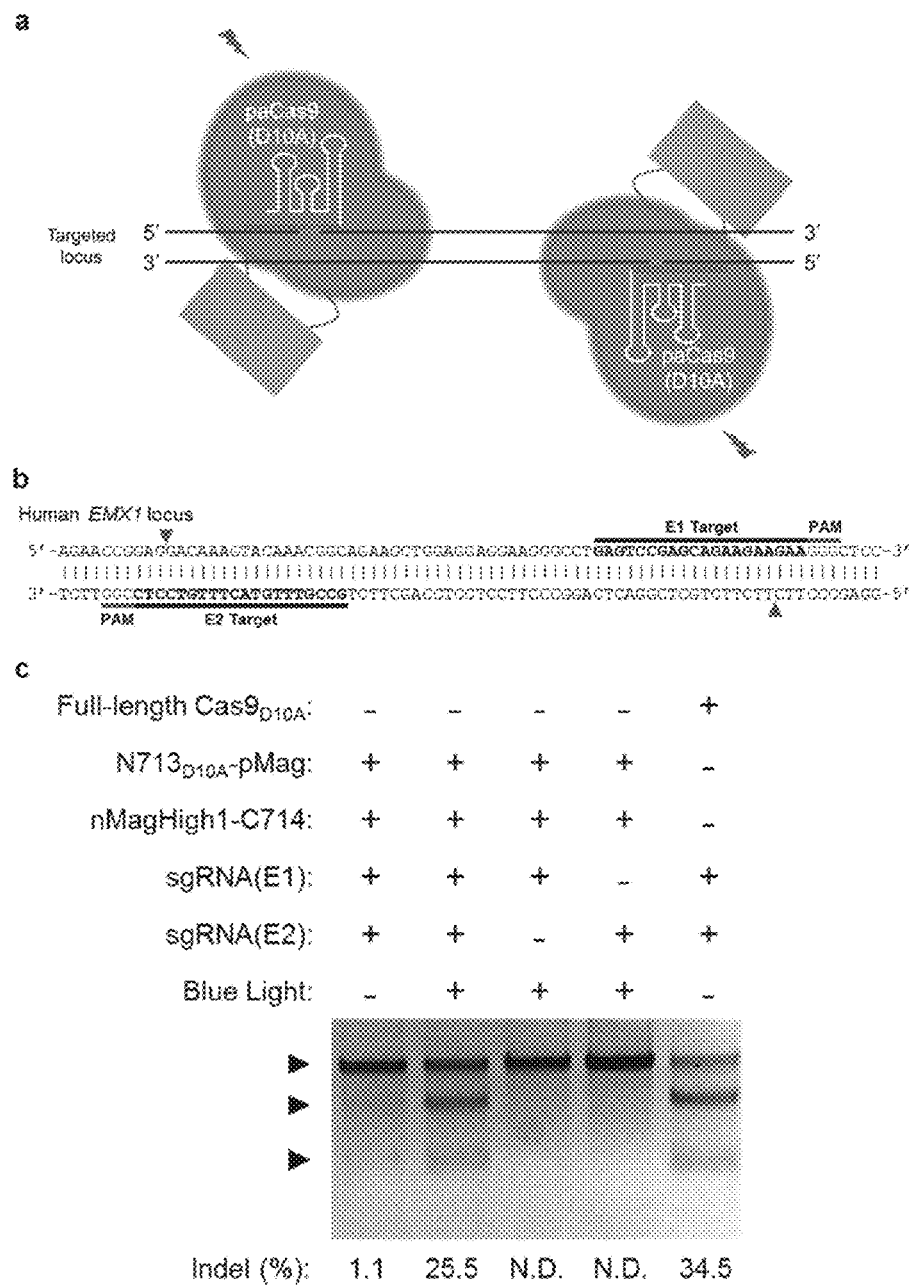

[Fig. 11]
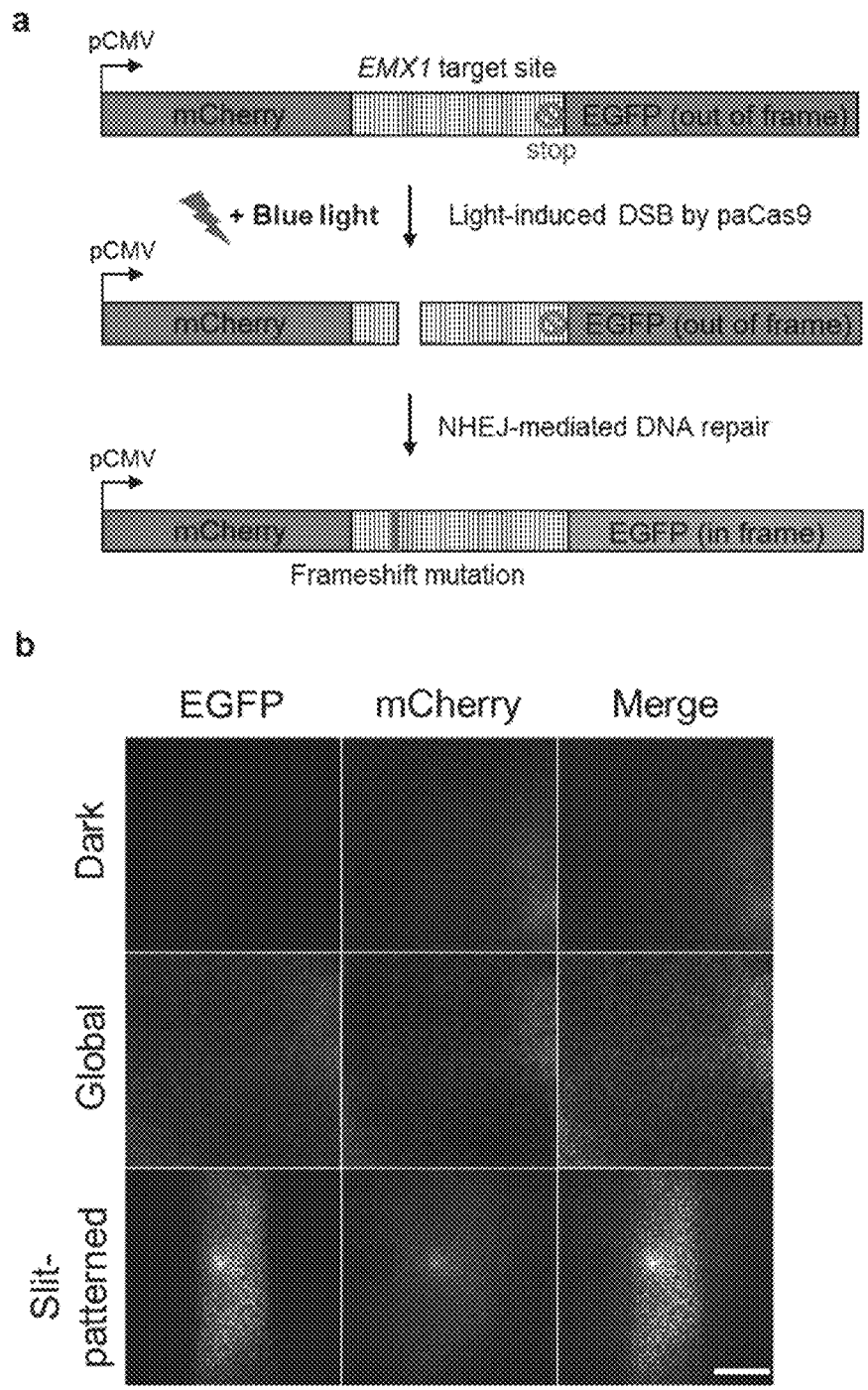

[Fig. 12]

NLS-N713-GS-pMag-GS

MGTPKKKRKVGIHGVPAADKKYSIGLDIGTNSVGWAVITDEYKVPSKKFKVLGNT
DRHSIKKNLIGALLFDSGETAEATRLKRTARRRYTRRKNRICYLQEIFSNEMAKV
DDSFFHRLEESFLVEEDKKHERHPIFGNIVDEVAYHEKYPTIYHLRKKLVDSTDKA
DLRLIYLALAHMIKFRGHFLIEGDLNPDNSDVDKLFIQLVQTYNQLFEENPINASG
VDAKAILSARLSKSRRLENLIAQLPGEKKNGLFGNLIALSLGLTPNFKSNFDLAE
DAKLQLSKDTYDDDLDNLLAQIGDQYADLFLAAKNLSDAILLSDILRVNTEITKAP
LSASMIKRYDEHHQDLTLLKALVRQQLPEKYKEIFFDQSKNGYAGYIDGGASQE
EFYKFIKPILEKMDGTEELLVKLNREDLLRKQRTFDNGSIPHQIHLGELHAILRRQ
EDFYPFLKDNREKIEKILTFRIPYYVGPLARGNSRFAWMTRKSEETITPWNFEEVV
DKGASAQSFIERMTNFDKNLPNEKVLPKHSLLYEYFTVYNELTKVKYVTEGMRK
PAFLSGEQKKAIVDLLFKTNRKVTVKQLKEDYFKKIECFDSVEISGVEDRFNASL
GTYHDLLKIIKDKDFLDNEENEDILEDIVLTLTLFEDREMIEERLKTYAHLFDDKVM
KQLKRRRYTGWGRLSRKLINGIRDKQSGKTILDFLKSDGFANRNFMQLIHDDSLT
FKEDIQKAQVEFGGSGSSGGSGHTLYAPGGYDIMGYLRQIRNRPNPQVELGPVD
TSCALILCDLKQKDTPIVYASEAFLYMTGYSNAEVLGRNCRFLQSPDGMVKPKS
TRKYVDSNTINTMRKAIDRNAEVQVEVVNFKKNGQRFVNFLTMIPVRDETGEYRY
SMGFQCETEGGSGGSGGGSGSGSGGLESRGPFEGKPIPNPLLGLDSTRTGHHH
HHH

[Fig. 13]

GS-nMagHigh1-GS-C714-NLS

MGGSGSSGGSGGSGGSGHTLYAPGGYDIMGYLDQIGNRPNPQVELGPVDTSCA
LILCDLKQKDTPIVYASEAFLYMTGYSNAEVLGRNCRFLQSPDGMVKPKSTRKY
VDSNTINTIRKAIDRNAEVQVEVVNFKKNGQRFVNFLTIIPVRDETGEYRYSMGFQ
CETEGGSGGSGGGSGSGSGGGTSGGGDSLHEHIANLAGSPAIKKGILQTVKVV
DELVKVMGRHKPENIVIEMARENQTTQKGQKNSRERMKRIEEGIKELGSQILKEH
PVENTQLQNEKLYLYYLQNGRDMYVDQELDINRLSDYDVDHIVPQSFLKDDSIDN
KVLTRSDKNRGKSDNVPSEEVVKKMKNYWRQLLNAKLITQRKFDNLTKAERGG
LSELDKAGFIKRQLVETRQITKHVAQILDSRMNTKYDENDKLIREVKVITLKSKLV
SDFRKDFQFYKVREINNYHHAHDAYLNAVVGTALIKKYPKLESEFVYGDYKVYDV
RKMIAKSEQEIGKATAKYFFYSNIMNFFKTEITLANGEIRKRPLIETNGETGEIVWD
KGRDFATVRKVLSMPQVNIVKKTEVQTGGFSKESILPKRNSDKLIARKKDWDPK
KYGGFDSPTVAYSVLVVAKVEKGKSKKLKSVKELLGITIMERSSFEKNPIDFLEA
KGYKEVKKDLIIKLPKYSLFELENGRKRMLASAGELQKGNELALPSKYVNFLYLA
SHYEKLKGSPEDNEQKQLFVEQHKHYLDEIIEQISEFSKRVILADANLDKVLSAYN
KHRDKPIREQAENIIHLFTLTNLGAPAAFKYFDTTIDRKRYTSTKEVLDATLIHQSIT
GLYETRIDLSQLGGDEFASPKKKRKVLESRGPFEGKPIPNPLLGLDSTRTGHHHH
HH

[Fig. 14]

GS-nMag-GS-C714-NLS

MGGSGSSGGSGGSGGSGHTLYAPGGYDIMGYLDQIGNRPNPQVELGPVDTSCA
LILCDLKQKDTPIVYASEAFLYMTGYSNAEVLGRNCRFLQSPDGMVKPKSTRKY
VDSNTINTMRKAIDRNAEVQVEVVNFKKNGQRFVNFLTMIPVRDETGEYRYSMG
FQCETEGGSGGSGGGSGSGSGGGTSGGGDSLHEHIANLAGSPAIKKGILQTVK
VVDELVKVMGRHKPENIVIEMARENQTTQKGQKNSRERMKRIEEGIKELGSQILK
EHPVENTQLQNEKLYLYYLQNGRDMYVDQELDINRLSDYDVDHIVPQSFLKDDSI
DNKVLTRSDKNRGKSDNVPSEEVVKKMKNYWRQLLNAKLITQRKFDNLTKAER
GGLSELDKAGFIKRQLVETRQITKHVAQILDSRMNTKYDENDKLIREVKVITLKSK
LVSDFRKDFQFYKVREINNYHHAHDAYLNAVVGTALIKKYPKLESEFVYGDYKVY
DVRKMIAKSEQEIGKATAKYFFYSNIMNFFKTEITLANGEIRKRPLIETNGETGEIV
WDKGRDFATVRKVLSMPQVNIVKKTEVQTGGFSKESILPKRNSDKLIARKKDWD
PKKYGGFDSPTVAYSVLVVAKVEKGKSKKLKSVKELLGITIMERSSFEKNPIDFL
EAKGYKEVKKDLIIKLPKYSLFELENGRKRMLASAGELQKGNELALPSKYVNFLY
LASHYEKLKGSPEDNEQKQLFVEQHKHYLDEIIEQISEFSKRVILADANLDKVLSA
YNKHRDKPIREQAENIIHLFTLTNLGAPAAFKYFDTTIDRKRYTSTKEVLDATLIHQ
SITGLYETRIDLSQLGGDEFASPKKKRKVLESRGPFEGKPIPNPLLGLDSTRTGHH
HHHH

[Fig. 15]

StopFluc-1

ATGGAAGATGCCAAAAACATTAAGAAGGGCCCAGCGCCATTCTACCCACTCGA
AGACGGGACCGCCGGCGAGCAGCTGCACAAAGCCATGAAGCGCTACGCCCT
GGTGCCCGGCACCATCGCCTTTACCGACGCACATATCGAGGTGGACATTACC
TACGCCGAGTACTTCGAGATGAGCGTTCGGCTGGCAGAAGCTATGAAGCGCT
ATGGGCTGAATACAAACCATCGGATCGTGGTGTGCAGCGAGAATAGCTTGCA
GTTCTTCATGCCCGTGTTGGGTGCCCTGTTCATCGGTGTGGCTGTGGCCCCA
GCTAACGACATCTACAACGAGCGCGAGCTGCTGAACAGCATGGGCATCAGCC
AGCCCACCGTCGTATTCGTGAGCAAGAAGGGCTGCAAAGATCCTCAACGT
GCAAAAGAAGCTACCGATCATACAAAGATCATCATCATGGATAGCAAGACCG
ACTACCAGGGCTTCCAAAGCATGTACACCTTCGTGACTTCCCATTTGCCACCC
GGCTTCAACGAGTACGACTTCGTGCCCGAGAGCTTCGACCGGGACAAAACCA
TCGCCCTGATCATGAACAGTAGTGGCAGTACCGGATTGCCCAAGGGCGTAGC
CCTACCGCACCGCACCGCTTGTGTCCGATTCAGTCATGCCCGCGACCCCATC
TTCGGCAACCAGATCATCCCCGACACCGCTATCCTCAGCGTGGTGCCATTTCA
CCACGGCTTCGGCATGTTCACCACGCTGGGCTACTTGATCTGCGGCTTTCGG
GTCGTGCTCATGTACCGCTTCGAGGAGGAGCTATTCTTGCGCAGCTTGCAAGA
CTATAAGATTCAATCTGCCCTGCTGGTGCCCACACTATTTAGCTTCTTCGCTAA
GAGCACTCTCATCGACAAGTACGACCTAAGCAACTTGCACGAGATCT<u>AA</u>AG<u>C</u>
<u>GG</u>CGGGGCGCCGCTCAGCAAGGAGGTAGGTGAGGCCGTGGCCAAACGCTTC
CACCTACCAGGCATCCGCCAGGGCTACGGCCTGACAGAAACAACCAGCGCCA
TTCTGATCACCCCCGAAGGGGACGACAAGCCTGGCGCAGTAGGCAAGGTGGT
GCCCTTCTTCGAGGCTAAGGTGGTGGACTTGGACACCGGTAAGACACTGGGT
GTGAACCAGCGCGGCGAGCTGTGCGTCCGTGGCCCCATGATCATGAGCGGC
TACGTTAACAACCCCGAGGCTACAAACGCTCTCATCGACAAGGACGGCTGGC
TGCACAGCGGCGACATCGCCTACTGGGACGAGGACGAGCACTTCTTCATCGT
GGACCGGCTGAAGAGCCTGATCAAATACAAGGGCTACCAGGTAGCCCCAGCC
GAACTGGAGAGCATCCTGCTGCAACACCCCAACATCTTCGACGCCGGGGTCG
CCGGCCTGCCCGACGACGATGCCGGCGAGCTGCCCGCCGCAGTCGTCGTGC
TGGAACACGGTAAAACCATGACCGAGAAGGAGATCGTGGACTATGTGGCCAG
CCAGGTTACAACCGCCAAGAAGCTGCGCGGTGGTGTTGTGTTCGTGGACGAG
GTGCCTAAAGGACTGACCGGCAAGTTGGACGCCCGCAAGATCCGCGAGATTC
TCATTAAGGCCAAGAAGTAA

[Fig. 16]

StopFluc-2

ATGGAAGATGCCAAAAACATTAAGAAGGGCCCAGCGCCATTCTACCCACTCGA
AGACGGGACCGCCGGCGAGCAGCTGCACAAAGCCATGAAGCGCTACGCCCT
GGTGCCCGGCACCATCGCCTTTACCGACGCACATATCGAGGTGGACATTACC
TACGCCGAGTACTTCGAGATGAGCGTTCGGCTGGCAGAAGCTATGAAGTAAT
ATGGGCTGAATACAAACCATCGGATCGTGGTGTGCAGCGAGAATAGCTTGCA
GTTCTTCATGCCCGTGTTGGGTGCCCTGTTCATCGGTGTGGCTGTGGCCCCA
GCTAACGACATCTACAACGAGCGCGAGCTGCTGAACAGCATGGGCATCAGCC
AGCCCACCGTCGTATTCGTGAGCAAGAAGGGCTGCAAAGATCCTCAACGT
GCAAAAGAAGCTACCGATCATACAAAGATCATCATCATGGATAGCAAGACCG
ACTACCAGGGCTTCCAAAGCATGTACACCTTCGTGACTTCCCATTTGCCACCC
GGCTTCAACGAGTACGACTTCGTGCCCGAGAGCTTCGACCGGGACAAAACCA
TCGCCCTGATCATGAACAGTAGTGGCAGTACCGGATTGCCCAAGGGCGTAGC
CCTACCGCACCGCACCGCTTGTGTCCGATTCAGTCATGCCCGCGACCCCATC
TTCGGCAACCAGATCATCCCCGACACCGCTATCCTCAGCGTGGTGCCATTTCA
CCACGGCTTCGGCATGTTCACCACGCTGGGCTACTTGATCTGCGGCTTTCGG
GTCGTGCTCATGTACCGCTTCGAGGAGGAGCTATTCTTGCGCAGCTTGCAAGA
CTATAAGATTCAATCTGCCCTGCTGGTGCCCACACTATTTAGCTTCTTCGCTAA
GAGCACTCTCATCGACAAGTACGACCTAAGCAACTTGCACGAGATCGCCAGC
GGCGGGGCGCCGCTCAGCAAGGAGGTAGGTGAGGCCGTGGCCAAACGCTTC
CACCTACCAGGCATCCGCCAGGGCTACGGCCTGACAGAAACAACCAGCGCCA
TTCTGATCACCCCCGAAGGGGACGACAAGCCTGGCGCAGTAGGCAAGGTGGT
GCCCTTCTTCGAGGCTAAGGTGGTGGACTTGGACACCGGTAAGACACTGGGT
GTGAACCAGCGCGGCGAGCTGTGCGTCCGTGGCCCCATGATCATGAGCGGC
TACGTTAACAACCCCGAGGCTACAAACGCTCTCATCGACAAGGACGGCTGGC
TGCACAGCGGCGACATCGCCTACTGGGACGAGGACGAGCACTTCTTCATCGT
GGACCGGCTGAAGAGCCTGATCAAATACAAGGGCTACCAGGTAGCCCCAGCC
GAACTGGAGAGCATCCTGCTGCAACACCCCAACATCTTCGACGCCGGGGTCG
CCGGCCTGCCCGACGACGATGCCGGCGAGCTGCCCGCCGCAGTCGTCGTGC
TGGAACACGGTAAAACCATGACCGAGAAGGAGATCGTGGACTATGTGGCCAG
CCAGGTTACAACCGCCAAGAAGCTGCGCGGTGGTGTTGTGTTCGTGGACGAG
GTGCCTAAAGGACTGACCGGCAAGTTGGACGCCCGCAAGATCCGCGAGATTC
TCATTAAGGCCAAGAAGTAA

[Fig. 17]

StopFluc-3

ATGGAAGATGCCAAAAACATTAAGAAGGGCCCAGCGCCATTCTACCCACTCGA
AGACGGGACCGCCGGCGAGCAGCTGCACAAAGCCATGAAGCGCTACGCCCT
GGTGCCCGGCACCATCGCCTTTACCGACGCACATATCGAGGTGGACATTACC
TACGCCGAGTACTTCGAGATGAGCGTTCGGCTGGCAGAAGCTATGAAGCGCT
ATGGGCTGAATACAAACCATCGGATCGTGGTGTGCAGCGAGAATAGCTTGCA
GTTCTTCATGCCCGTGTTGGGTGCCCTGTTCATCTAAG<u>TGG</u>CTGTGGCCCCA
GCTAACGACATCTACAACGAGCGCGAGCTGCTGAACAGCATGGGCATCAGCC
AGCCCACCGTCGTATTCGTGAGCAAGAAGGGCTGCAAAGATCCTCAACGT
GCAAAAGAAGCTACCGATCATACAAAGATCATCATCATGGATAGCAAGACCG
ACTACCAGGGCTTCCAAAGCATGTACACCTTCGTGACTTCCCATTTGCCACCC
GGCTTCAACGAGTACGACTTCGTGCCCGAGAGCTTCGACCGGGACAAAACCA
TCGCCCTGATCATGAACAGTAGTGGCAGTACCGGATTGCCCAAGGGCGTAGC
CCTACCGCACCGCACCGCTTGTGTCCGATTCAGTCATGCCCGCGACCCCATC
TTCGGCAACCAGATCATCCCCGACACCGCTATCCTCAGCGTGGTGCCATTTCA
CCACGGCTTCGGCATGTTCACCACGCTGGGCTACTTGATCTGCGGCTTTCGG
GTCGTGCTCATGTACCGCTTCGAGGAGGAGCTATTCTTGCGCAGCTTGCAAGA
CTATAAGATTCAATCTGCCCTGCTGGTGCCCACACTATTTAGCTTCTTCGCTAA
GAGCACTCTCATCGACAAGTACGACCTAAGCAACTTGCACGAGATCTAAAGCG
GCGGGGCGCCGCTCAGCAAGGAGGTAGGTGAGGCCGTGGCCAAACGCTTCC
ACCTACCAGGCATCCGCCAGGGCTACGGCCTGACAGAAACAACCAGCGCCAT
TCTGATCACCCCCGAAGGGGACGACAAGCCTGGCGCAGTAGGCAAGGTGGT
GCCCTTCTTCGAGGCTAAGGTGGTGGACTTGGACACCGGTAAGACACTGGGT
GTGAACCAGCGCGGCGAGCTGTGCGTCCGTGGCCCCATGATCATGAGCGGC
TACGTTAACAACCCCGAGGCTACAAACGCTCTCATCGACAAGGACGGCTGGC
TGCACAGCGGCGACATCGCCTACTGGGACGAGGACGAGCACTTCTTCATCGT
GGACCGGCTGAAGAGCCTGATCAAATACAAGGGCTACCAGGTAGCCCCAGCC
GAACTGGAGAGCATCCTGCTGCAACACCCCAACATCTTCGACGCCGGGGTCG
CCGGCCTGCCCGACGACGATGCCGGCGAGCTGCCCGCCGCAGTCGTCGTGC
TGGAACACGGTAAAACCATGACCGAGAAGGAGATCGTGGACTATGTGGCCAG
CCAGGTTACAACCGCCAAGAAGCTGCGCGGTGGTGTTGTGTTCGTGGACGAG
GTGCCTAAAGGACTGACCGGCAAGTTGGACGCCCGCAAGATCCGCGAGATTC
TCATTAAGGCCAAGAAGTAA

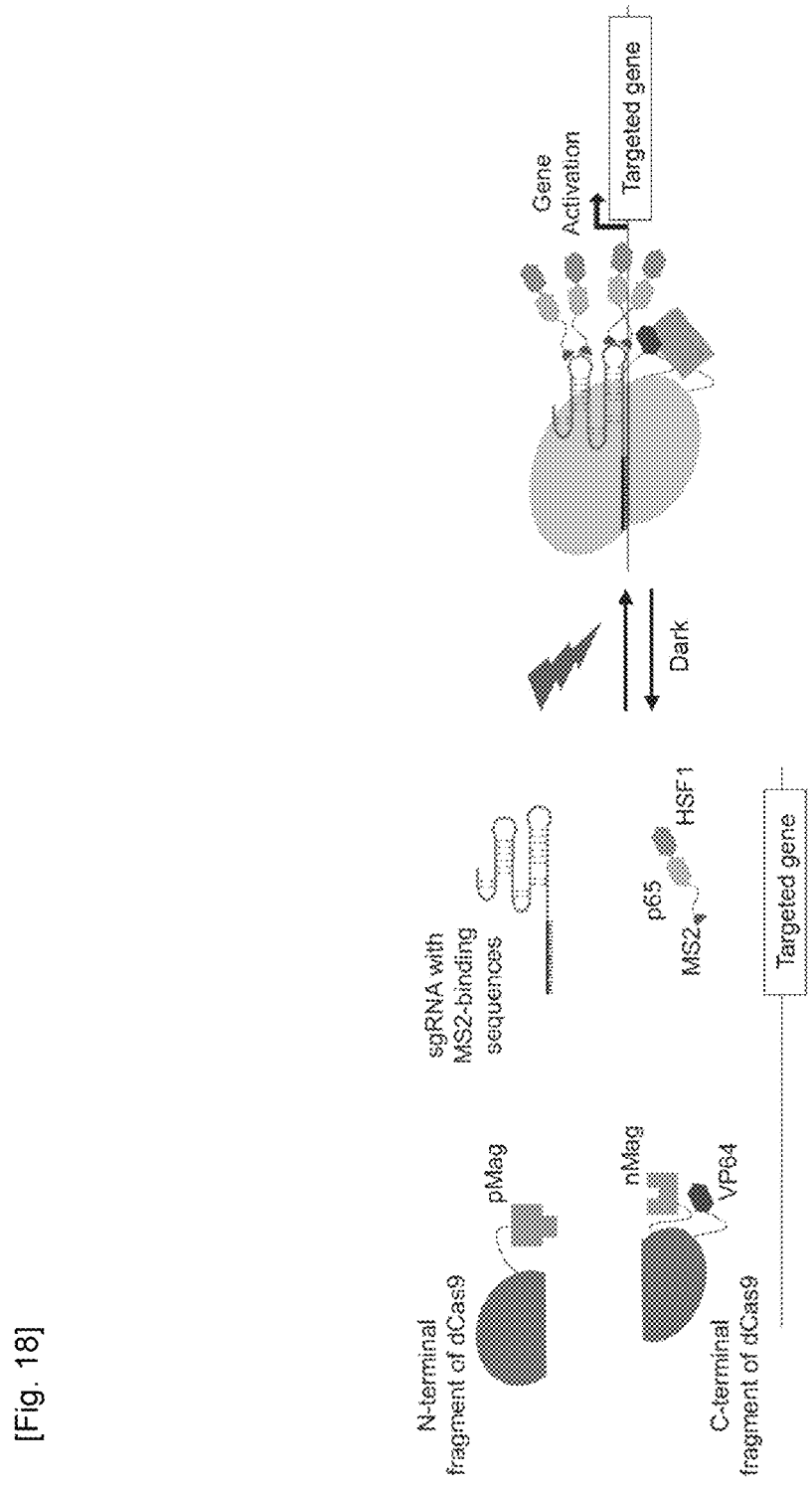
[Fig. 18]

[Fig. 19]
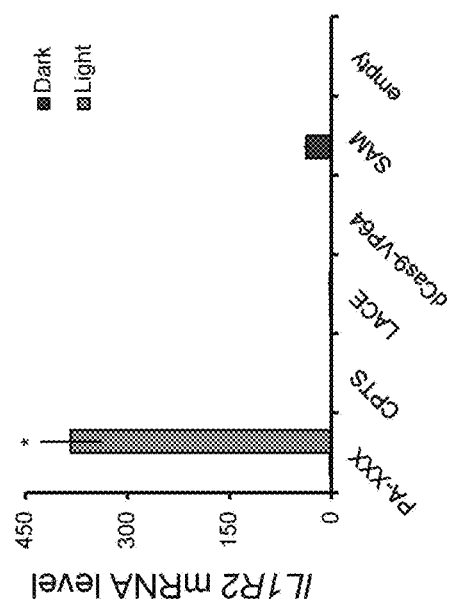
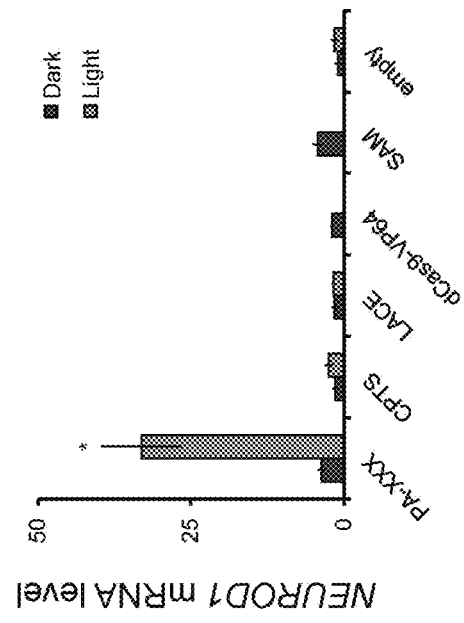
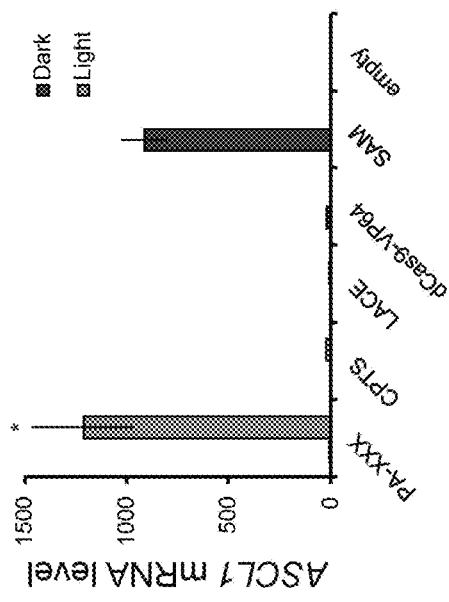

[Fig. 20]
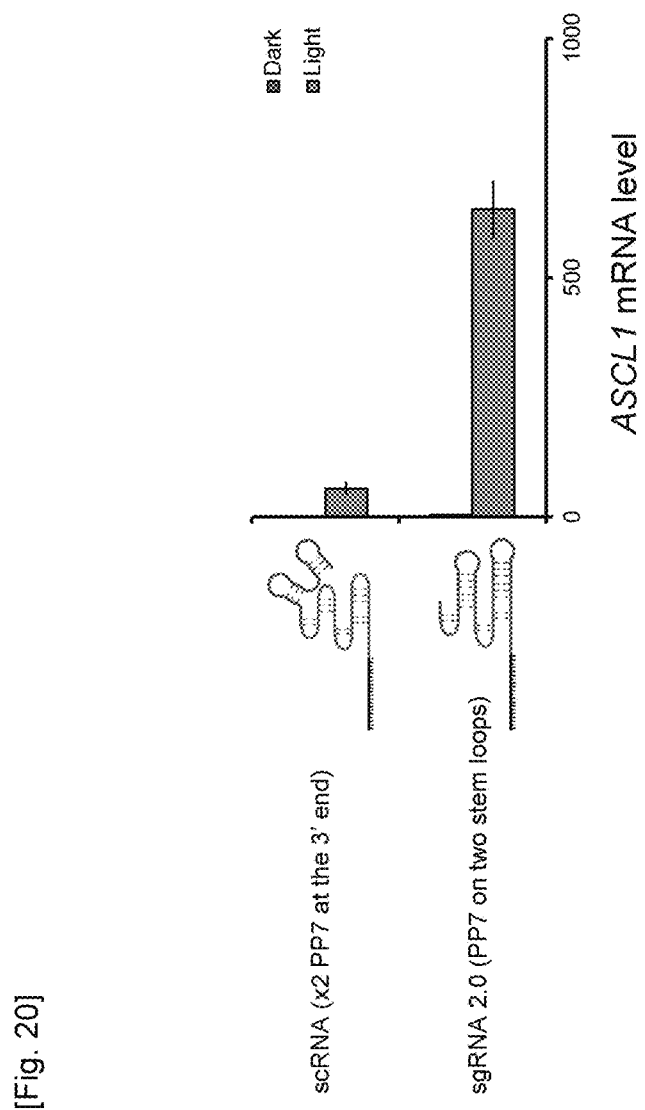

[Fig. 21]
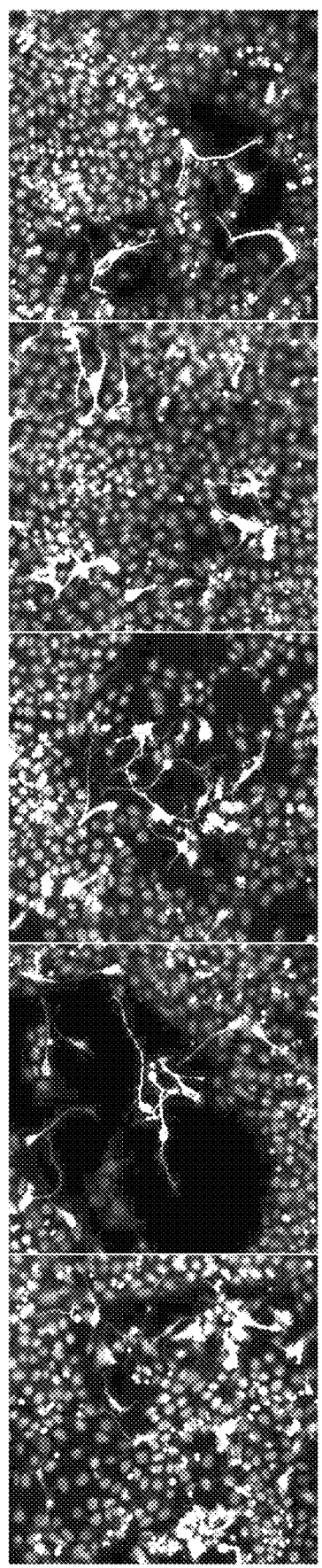
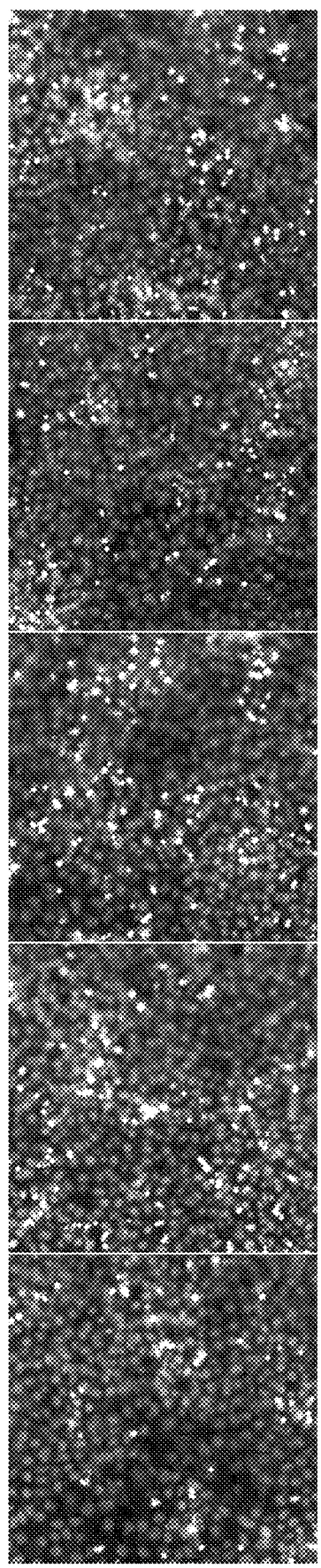

[Fig. 22]

NES-dN713-GS-pMag-GS-NES

MGLPPLERLTLGSDKKYSIGLAIGTNSVGWAVITDEYKVPSKKFKVLGNTDRH
SIKKNLIGALLFDSGETAEATRLKRTARRRYTRRKNRICYLQEIFSNEMAKVD
DSFFHRLEESFLVEEDKKHERHPIFGNIVDEVAYHEKYPTIYHLRKKLVDSTDK
ADLRLIYLALAHMIKFRGHFLIEGDLNPDNSDVDKLFIQLVQTYNQLFEENPIN
ASGVDAKAILSARLSKSRRLENLIAQLPGEKKNGLFGNLIALSLGLTPNFKSN
FDLAEDAKLQLSKDTYDDDLDNLLAQIGDQYADLFLAAKNLSDAILLSDILRV
NTEITKAPLSASMIKRYDEHHQDLTLLKALVRQQLPEKYKEIFFDQSKNGYAG
YIDGGASQEEFYKFIKPILEKMDGTEELLVKLNREDLLRKQRTFDNGSIPHQIH
LGELHAILRRQEDFYPFLKDNREKIEKILTFRIPYYVGPLARGNSRFAWMTRK
SEETITPWNFEEVVDKGASAQSFIERMTNFDKNLPNEKVLPKHSLLYEYFTVY
NELTKVKYVTEGMRKPAFLSGEQKKAIVDLLFKTNRKVTVKQLKEDYFKKIE
CFDSVEISGVEDRFNASLGTYHDLLKIIKDKDFLDNEENEDILEDIVLTLTLFED
REMIEERLKTYAHLFDDKVMKQLKRRRYTGWGRLSRKLINGIRDKQSGKTIL
DFLKSDGFANRNFMQLIHDDSLTFKEDIQKAQVGTGGSGSSGGSGHTLYAPG
GYDIMGYLRQIRNRPNPQVELGPVDTSCALILCDLKQKDTPIVYASEAFLYMT
GYSNAEVLGRNCRFLQSPDGMVKPKSTRKYVDSNTINTMRKAIDRNAEVQV
EVVNFKKNGQRFVNFLTMIPVRDETGEYRYSMGFQCETEGGSGGSGGGSGS
GSGGEFLPPLERLTL

[Fig. 23]

GS-nMagHigh1-GS-dC714-GS-NLS-VP64

MGGSGSSGGSGGSGGSGHTLYAPGGYDIMGYLDQIGNRPNPQVELGPVDT
SCALILCDLKQKDTPIVYASEAFLYMTGYSNAEVLGRNCRFLQSPDGMVKPK
STRKYVDSNTINTIRKAIDRNAEVQVEVVNFKKNGQRFVNFLTIIPVRDETGEY
RYSMGFQCETEGGSGGSGGGSGSGSGGGTSGQGDSLHEHIANLAGSPAIK
KGILQTVKVVDELVKVMGRHKPENIVIEMARENQTTQKGQKNSRERMKRIEE
GIKELGSQILKEHPVENTQLQNEKLYLYYLQNGRDMYVDQELDINRLSDYDV
DAIVPQSFLKDDSIDNKVLTRSDKNRGKSDNVPSEEVVKKMKNYWRQLLNA
KLITQRKFDNLTKAERGGLSELDKAGFIKRQLVETRQITKHVAQILDSRMNTK
YDENDKLIREVKVITLKSKLVSDFRKDFQFYKVREINNYHHAHDAYLNAVVGT
ALIKKYPKLESEFVYGDYKVYDVRKMIAKSEQEIGKATAKYFFYSNIMNFFKT
EITLANGEIRKRPLIETNGETGEIVWDKGRDFATVRKVLSMPQVNIVKKTEVQ
TGGFSKESILPKRNSDKLIARKKDWDPKKYGGFDSPTVAYSVLVVAKVEKG
KSKKLKSVKELLGITIMERSSFEKNPIDFLEAKGYKEVKKDLIIKLPKYSLFELE
NGRKRMLASAGELQKGNELALPSKYVNFLYLASHYEKLKGSPEDNEQKQLF
VEQHKHYLDEIIEQISEFSKRVILADANLDKVLSAYNKHRDKPIREQAENIIHLF
TLTNLGAPAAFKYFDTTIDRKRYTSTKEVLDATLIHQSITGLYETRIDLSQLGG
DEFGGGGSGGGGSGGGGSGPKKKRKVAAAGSGRADALDDFDLDMLGSDA
LDDFDLDMLGSDALDDFDLDMLGSDALDDFDLDMLIN

[Fig. 24]

NLS-GS-MS2-GS-NLS-p65-GS-HSF1

MGPKKKRKVGGSGMASNFTQFVLVDNGGTGDVTVAPSNFANGIAEWISSNS
RSQAYKVTCSVRQSSAQNRKYTIKVEVPKGAWRSYLNMELTIPIFATNSDCE
LIVKAMQGLLKDGNPIPSAIAANSGIYAGGSGGSGGGSGSGSGSGPKKKRK
VAAAGSPSGQISNQALALAPSSAPVLAQTMVPSSAMVPLAQPPAPAPVLTPG
PPQSLSAPVPKSTQAGEGTLSEALLHLQFDADEDLGALLGNSTDPGVFTDLAS
VDNSEFQQLLNQGVSMSHSTAEPMLMEYPEAITRLVTGSQRPPDPAPTPLGT
SGLPNGLSGDEDFSSIADMDFSALLSQISSSGQGGGGSGFSVDTSALLDLFS
PSVTVPDMSLPDLDSSLASIQELLSPQEPPRPPEAENSSPDSGKQLVHYTAQ
PLFLLDPGSVDTGSNDLPVLFELGEGSYFSEGDGFAEDPTISLLTGSEPPKA
KDPTVS

SEQUENCE LISTING

<160> NUMBER OF SEQ ID NOS: 269

<210> SEQ ID NO 1
<211> LENGTH: 186
<212> TYPE: PRT
<213> ORGANISM: NEUROSPORA CRASSA

<400> SEQUENCE: 1

Met Ser His Thr Val Asn Ser Ser Thr Met Asn Pro Trp Glu Val Glu
1               5                   10                  15

Ala Tyr Gln Gln Tyr His Tyr Asp Pro Arg Thr Ala Pro Thr Ala Asn
            20                  25                  30

Pro Leu Phe Phe His Thr Leu Tyr Ala Pro Gly Gly Tyr Asp Ile Met
        35                  40                  45

Gly Tyr Leu Ile Gln Ile Met Asn Arg Pro Asn Pro Gln Val Glu Leu
50                  55                  60

Gly Pro Val Asp Thr Ser Cys Ala Leu Ile Leu Cys Asp Leu Lys Gln
65                  70                  75                  80

Lys Asp Thr Pro Ile Val Tyr Ala Ser Glu Ala Phe Leu Tyr Met Thr
                85                  90                  95

Gly Tyr Ser Asn Ala Glu Val Leu Gly Arg Asn Cys Arg Phe Leu Gln
            100                 105                 110

Ser Pro Asp Gly Met Val Lys Pro Lys Ser Thr Arg Lys Tyr Val Asp
        115                 120                 125

Ser Asn Thr Ile Asn Thr Met Arg Lys Ala Ile Asp Arg Asn Ala Glu
130                 135                 140

Val Gln Val Glu Val Val Asn Phe Lys Lys Asn Gly Gln Arg Phe Val
145                 150                 155                 160

Asn Phe Leu Thr Met Ile Pro Val Arg Asp Glu Thr Gly Glu Tyr Arg
                165                 170                 175

Tyr Ser Met Gly Phe Gln Cys Glu Thr Glu
            180                 185

<210> SEQ ID NO 2
<211> LENGTH: 1368
<212> TYPE: PRT
<213> ORGANISM: Streptococcus pyogenes

<400> SEQUENCE: 2

Met Asp Lys Lys Tyr Ser Ile Gly Leu Asp Ile Gly Thr Asn Ser Val
1               5                   10                  15

Gly Trp Ala Val Ile Thr Asp Glu Tyr Lys Val Pro Ser Lys Lys Phe
            20                  25                  30

Lys Val Leu Gly Asn Thr Asp Arg His Ser Ile Lys Lys Asn Leu Ile
        35                  40                  45

Gly Ala Leu Leu Phe Asp Ser Gly Glu Thr Ala Glu Ala Thr Arg Leu
50                  55                  60

Lys Arg Thr Ala Arg Arg Arg Tyr Thr Arg Arg Lys Asn Arg Ile Cys
65                  70                  75                  80

Tyr Leu Gln Glu Ile Phe Ser Asn Glu Met Ala Lys Val Asp Asp Ser
                85                  90                  95

Phe Phe His Arg Leu Glu Glu Ser Phe Leu Val Glu Glu Asp Lys Lys
            100                 105                 110

His Glu Arg His Pro Ile Phe Gly Asn Ile Val Asp Glu Val Ala Tyr
        115                 120                 125

His Glu Lys Tyr Pro Thr Ile Tyr His Leu Arg Lys Lys Leu Val Asp

```
                130             135             140
    Ser Thr Asp Lys Ala Asp Leu Arg Leu Ile Tyr Leu Ala Leu Ala His
    145                 150                 155                 160

Met Ile Lys Phe Arg Gly His Phe Leu Ile Glu Gly Asp Leu Asn Pro
                    165                 170                 175

Asp Asn Ser Asp Val Asp Lys Leu Phe Ile Gln Leu Val Gln Thr Tyr
                180                 185                 190

Asn Gln Leu Phe Glu Glu Asn Pro Ile Asn Ala Ser Gly Val Asp Ala
                195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
    225                 230                 235                 240

Leu Ile Ala Leu Ser Leu Gly Leu Thr Pro Asn Phe Lys Ser Asn Phe
                    245                 250                 255

Asp Leu Ala Glu Asp Ala Lys Leu Gln Leu Ser Lys Asp Thr Tyr Asp
                260                 265                 270

Asp Asp Leu Asp Asn Leu Leu Ala Gln Ile Gly Asp Gln Tyr Ala Asp
                275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
    305                 310                 315                 320

Met Ile Lys Arg Tyr Asp Glu His His Gln Asp Leu Thr Leu Leu Lys
                    325                 330                 335

Ala Leu Val Arg Gln Gln Leu Pro Glu Lys Tyr Lys Glu Ile Phe Phe
                340                 345                 350

Asp Gln Ser Lys Asn Gly Tyr Ala Gly Tyr Ile Asp Gly Gly Ala Ser
                355                 360                 365

Gln Glu Glu Phe Tyr Lys Phe Ile Lys Pro Ile Leu Glu Lys Met Asp
                370                 375                 380

Gly Thr Glu Glu Leu Leu Val Lys Leu Asn Arg Glu Asp Leu Leu Arg
    385                 390                 395                 400

Lys Gln Arg Thr Phe Asp Asn Gly Ser Ile Pro His Gln Ile His Leu
                    405                 410                 415

Gly Glu Leu His Ala Ile Leu Arg Arg Gln Glu Asp Phe Tyr Pro Phe
                420                 425                 430

Leu Lys Asp Asn Arg Glu Lys Ile Glu Lys Ile Leu Thr Phe Arg Ile
                435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
    465                 470                 475                 480

Val Val Asp Lys Gly Ala Ser Ala Gln Ser Phe Ile Glu Arg Met Thr
                    485                 490                 495

Asn Phe Asp Lys Asn Leu Pro Asn Glu Lys Val Leu Pro Lys His Ser
                500                 505                 510

Leu Leu Tyr Glu Tyr Phe Thr Val Tyr Asn Glu Leu Thr Lys Val Lys
                515                 520                 525

Tyr Val Thr Glu Gly Met Arg Lys Pro Ala Phe Leu Ser Gly Glu Gln
                530                 535                 540

Lys Lys Ala Ile Val Asp Leu Leu Phe Lys Thr Asn Arg Lys Val Thr
    545                 550                 555                 560
```

```
Val Lys Gln Leu Lys Glu Asp Tyr Phe Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
            595                 600                 605

Asn Glu Glu Asn Glu Asp Ile Leu Glu Asp Ile Val Leu Thr Leu Thr
        610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670

Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975
```

-continued

```
Glu Ile Asn Asn Tyr His His Ala His Asp Ala Tyr Leu Asn Ala Val
            980                 985                 990

Val Gly Thr Ala Leu Ile Lys Lys Tyr Pro Lys Leu Glu Ser Glu Phe
    995                 1000                1005

Val Tyr Gly Asp Tyr Lys Val Tyr Asp Val Arg Lys Met Ile Ala
1010                1015                1020

Lys Ser Glu Gln Glu Ile Gly Lys Ala Thr Ala Lys Tyr Phe Phe
1025                1030                1035

Tyr Ser Asn Ile Met Asn Phe Phe Lys Thr Glu Ile Thr Leu Ala
1040                1045                1050

Asn Gly Glu Ile Arg Lys Arg Pro Leu Ile Glu Thr Asn Gly Glu
1055                1060                1065

Thr Gly Glu Ile Val Trp Asp Lys Gly Arg Asp Phe Ala Thr Val
1070                1075                1080

Arg Lys Val Leu Ser Met Pro Gln Val Asn Ile Val Lys Lys Thr
1085                1090                1095

Glu Val Gln Thr Gly Gly Phe Ser Lys Glu Ser Ile Leu Pro Lys
1100                1105                1110

Arg Asn Ser Asp Lys Leu Ile Ala Arg Lys Lys Asp Trp Asp Pro
1115                1120                1125

Lys Lys Tyr Gly Gly Phe Asp Ser Pro Thr Val Ala Tyr Ser Val
1130                1135                1140

Leu Val Val Ala Lys Val Glu Lys Gly Lys Ser Lys Lys Leu Lys
1145                1150                1155

Ser Val Lys Glu Leu Leu Gly Ile Thr Ile Met Glu Arg Ser Ser
1160                1165                1170

Phe Glu Lys Asn Pro Ile Asp Phe Leu Glu Ala Lys Gly Tyr Lys
1175                1180                1185

Glu Val Lys Lys Asp Leu Ile Ile Lys Leu Pro Lys Tyr Ser Leu
1190                1195                1200

Phe Glu Leu Glu Asn Gly Arg Lys Arg Met Leu Ala Ser Ala Gly
1205                1210                1215

Glu Leu Gln Lys Gly Asn Glu Leu Ala Leu Pro Ser Lys Tyr Val
1220                1225                1230

Asn Phe Leu Tyr Leu Ala Ser His Tyr Glu Lys Leu Lys Gly Ser
1235                1240                1245

Pro Glu Asp Asn Glu Gln Lys Gln Leu Phe Val Glu Gln His Lys
1250                1255                1260

His Tyr Leu Asp Glu Ile Ile Glu Gln Ile Ser Glu Phe Ser Lys
1265                1270                1275

Arg Val Ile Leu Ala Asp Ala Asn Leu Asp Lys Val Leu Ser Ala
1280                1285                1290

Tyr Asn Lys His Arg Asp Lys Pro Ile Arg Glu Gln Ala Glu Asn
1295                1300                1305

Ile Ile His Leu Phe Thr Leu Thr Asn Leu Gly Ala Pro Ala Ala
1310                1315                1320

Phe Lys Tyr Phe Asp Thr Thr Ile Asp Arg Lys Arg Tyr Thr Ser
1325                1330                1335

Thr Lys Glu Val Leu Asp Ala Thr Leu Ile His Gln Ser Ile Thr
1340                1345                1350

Gly Leu Tyr Glu Thr Arg Ile Asp Leu Ser Gln Leu Gly Gly Asp
1355                1360                1365
```

-continued

```
<210> SEQ ID NO 3
<211> LENGTH: 939
<212> TYPE: PRT
<213> ORGANISM: Artificial Sequence
<220> FEATURE:
<223> OTHER INFORMATION: NLS-N713-GS-pMag-GS

<400> SEQUENCE: 3

Met Gly Thr Pro Lys Lys Arg Lys Val Gly Ile His Gly Val Pro
1               5                   10                  15

Ala Ala Asp Lys Lys Tyr Ser Ile Gly Leu Asp Ile Gly Thr Asn Ser
                20                  25                  30

Val Gly Trp Ala Val Ile Thr Asp Glu Tyr Lys Val Pro Ser Lys Lys
            35                  40                  45

Phe Lys Val Leu Gly Asn Thr Asp Arg His Ser Ile Lys Lys Asn Leu
        50                  55                  60

Ile Gly Ala Leu Leu Phe Asp Ser Gly Glu Thr Ala Glu Ala Thr Arg
65                  70                  75                  80

Leu Lys Arg Thr Ala Arg Arg Arg Tyr Thr Arg Arg Lys Asn Arg Ile
                85                  90                  95

Cys Tyr Leu Gln Glu Ile Phe Ser Asn Glu Met Ala Lys Val Asp Asp
            100                 105                 110

Ser Phe Phe His Arg Leu Glu Glu Ser Phe Leu Val Glu Glu Asp Lys
        115                 120                 125

Lys His Glu Arg His Pro Ile Phe Gly Asn Ile Val Asp Glu Val Ala
    130                 135                 140

Tyr His Glu Lys Tyr Pro Thr Ile Tyr His Leu Arg Lys Lys Leu Val
145                 150                 155                 160

Asp Ser Thr Asp Lys Ala Asp Leu Arg Leu Ile Tyr Leu Ala Leu Ala
                165                 170                 175

His Met Ile Lys Phe Arg Gly His Phe Leu Ile Glu Gly Asp Leu Asn
            180                 185                 190

Pro Asp Asn Ser Asp Val Asp Lys Leu Phe Ile Gln Leu Val Gln Thr
        195                 200                 205

Tyr Asn Gln Leu Phe Glu Glu Asn Pro Ile Asn Ala Ser Gly Val Asp
    210                 215                 220

Ala Lys Ala Ile Leu Ser Ala Arg Leu Ser Lys Ser Arg Arg Leu Glu
225                 230                 235                 240

Asn Leu Ile Ala Gln Leu Pro Gly Glu Lys Lys Asn Gly Leu Phe Gly
                245                 250                 255

Asn Leu Ile Ala Leu Ser Leu Gly Leu Thr Pro Asn Phe Lys Ser Asn
            260                 265                 270

Phe Asp Leu Ala Glu Asp Ala Lys Leu Gln Leu Ser Lys Asp Thr Tyr
        275                 280                 285

Asp Asp Asp Leu Asp Asn Leu Leu Ala Gln Ile Gly Asp Gln Tyr Ala
    290                 295                 300

Asp Leu Phe Leu Ala Ala Lys Asn Leu Ser Asp Ala Ile Leu Leu Ser
305                 310                 315                 320

Asp Ile Leu Arg Val Asn Thr Glu Ile Thr Lys Ala Pro Leu Ser Ala
                325                 330                 335

Ser Met Ile Lys Arg Tyr Asp Glu His His Gln Asp Leu Thr Leu Leu
            340                 345                 350

Lys Ala Leu Val Arg Gln Gln Leu Pro Glu Lys Tyr Lys Glu Ile Phe
        355                 360                 365

Phe Asp Gln Ser Lys Asn Gly Tyr Ala Gly Tyr Ile Asp Gly Gly Ala
```

```
            370                 375                 380
Ser Gln Glu Glu Phe Tyr Lys Phe Ile Lys Pro Ile Leu Glu Lys Met
385                 390                 395                 400

Asp Gly Thr Glu Glu Leu Leu Val Lys Leu Asn Arg Glu Asp Leu Leu
                405                 410                 415

Arg Lys Gln Arg Thr Phe Asp Asn Gly Ser Ile Pro His Gln Ile His
            420                 425                 430

Leu Gly Glu Leu His Ala Ile Leu Arg Arg Gln Glu Asp Phe Tyr Pro
        435                 440                 445

Phe Leu Lys Asp Asn Arg Glu Lys Ile Glu Lys Ile Leu Thr Phe Arg
    450                 455                 460

Ile Pro Tyr Tyr Val Gly Pro Leu Ala Arg Gly Asn Ser Arg Phe Ala
465                 470                 475                 480

Trp Met Thr Arg Lys Ser Glu Glu Thr Ile Thr Pro Trp Asn Phe Glu
                485                 490                 495

Glu Val Val Asp Lys Gly Ala Ser Ala Gln Ser Phe Ile Glu Arg Met
                500                 505                 510

Thr Asn Phe Asp Lys Asn Leu Pro Asn Glu Lys Val Leu Pro Lys His
            515                 520                 525

Ser Leu Leu Tyr Glu Tyr Phe Thr Val Tyr Asn Glu Leu Thr Lys Val
        530                 535                 540

Lys Tyr Val Thr Glu Gly Met Arg Lys Pro Ala Phe Leu Ser Gly Glu
545                 550                 555                 560

Gln Lys Lys Ala Ile Val Asp Leu Leu Phe Lys Thr Asn Arg Lys Val
                565                 570                 575

Thr Val Lys Gln Leu Lys Glu Asp Tyr Phe Lys Lys Ile Glu Cys Phe
                580                 585                 590

Asp Ser Val Glu Ile Ser Gly Val Glu Asp Arg Phe Asn Ala Ser Leu
            595                 600                 605

Gly Thr Tyr His Asp Leu Leu Lys Ile Ile Lys Asp Lys Asp Phe Leu
        610                 615                 620

Asp Asn Glu Glu Asn Glu Asp Ile Leu Glu Asp Ile Val Leu Thr Leu
625                 630                 635                 640

Thr Leu Phe Glu Asp Arg Glu Met Ile Glu Glu Arg Leu Lys Thr Tyr
                645                 650                 655

Ala His Leu Phe Asp Asp Lys Val Met Lys Gln Leu Lys Arg Arg Arg
                660                 665                 670

Tyr Thr Gly Trp Gly Arg Leu Ser Arg Lys Leu Ile Asn Gly Ile Arg
            675                 680                 685

Asp Lys Gln Ser Gly Lys Thr Ile Leu Asp Phe Leu Lys Ser Asp Gly
        690                 695                 700

Phe Ala Asn Arg Asn Phe Met Gln Leu Ile His Asp Asp Ser Leu Thr
705                 710                 715                 720

Phe Lys Glu Asp Ile Gln Lys Ala Gln Val Glu Phe Gly Gly Ser Gly
                725                 730                 735

Ser Ser Gly Gly Ser Gly His Thr Leu Tyr Ala Pro Gly Gly Tyr Asp
                740                 745                 750

Ile Met Gly Tyr Leu Arg Gln Ile Arg Asn Arg Pro Asn Pro Gln Val
            755                 760                 765

Glu Leu Gly Pro Val Asp Thr Ser Cys Ala Leu Ile Leu Cys Asp Leu
        770                 775                 780

Lys Gln Lys Asp Thr Pro Ile Val Tyr Ala Ser Glu Ala Phe Leu Tyr
785                 790                 795                 800
```

```
Met Thr Gly Tyr Ser Asn Ala Glu Val Leu Gly Arg Asn Cys Arg Phe
            805                 810                 815

Leu Gln Ser Pro Asp Gly Met Val Lys Pro Lys Ser Thr Arg Lys Tyr
        820                 825                 830

Val Asp Ser Asn Thr Ile Asn Thr Met Arg Lys Ala Ile Asp Arg Asn
    835                 840                 845

Ala Glu Val Gln Val Glu Val Asn Phe Lys Lys Asn Gly Gln Arg
850                 855                 860

Phe Val Asn Phe Leu Thr Met Ile Pro Val Arg Asp Glu Thr Gly Glu
865                 870                 875                 880

Tyr Arg Tyr Ser Met Gly Phe Gln Cys Glu Thr Glu Gly Gly Ser Gly
                885                 890                 895

Gly Ser Gly Gly Gly Ser Gly Ser Gly Gly Gly Leu Glu Ser Arg
            900                 905                 910

Gly Pro Phe Glu Gly Lys Pro Ile Pro Asn Pro Leu Leu Gly Leu Asp
            915                 920                 925

Ser Thr Arg Thr Gly His His His His His
    930                 935

<210> SEQ ID NO 4
<211> LENGTH: 882
<212> TYPE: PRT
<213> ORGANISM: Artificial Sequence
<220> FEATURE:
<223> OTHER INFORMATION: GS-nMagHigh1-GS-C714-NLS

<400> SEQUENCE: 4

Met Gly Gly Ser Gly Ser Ser Gly Gly Ser Gly Gly Ser Gly Gly Ser
1               5                   10                  15

Gly His Thr Leu Tyr Ala Pro Gly Gly Tyr Asp Ile Met Gly Tyr Leu
            20                  25                  30

Asp Gln Ile Gly Asn Arg Pro Asn Pro Gln Val Glu Leu Gly Pro Val
        35                  40                  45

Asp Thr Ser Cys Ala Leu Ile Leu Cys Asp Leu Lys Gln Lys Asp Thr
    50                  55                  60

Pro Ile Val Tyr Ala Ser Glu Ala Phe Leu Tyr Met Thr Gly Tyr Ser
65                  70                  75                  80

Asn Ala Glu Val Leu Gly Arg Asn Cys Arg Phe Leu Gln Ser Pro Asp
                85                  90                  95

Gly Met Val Lys Pro Lys Ser Thr Arg Lys Tyr Val Asp Ser Asn Thr
            100                 105                 110

Ile Asn Thr Ile Arg Lys Ala Ile Asp Arg Asn Ala Glu Val Gln Val
        115                 120                 125

Glu Val Val Asn Phe Lys Lys Asn Gly Gln Arg Phe Val Asn Phe Leu
    130                 135                 140

Thr Ile Ile Pro Val Arg Asp Glu Thr Gly Glu Tyr Arg Tyr Ser Met
145                 150                 155                 160

Gly Phe Gln Cys Glu Thr Glu Gly Gly Ser Gly Gly Ser Gly Gly Gly
                165                 170                 175

Ser Gly Ser Gly Ser Gly Gly Gly Thr Ser Gly Gly Gly Asp Ser Leu
            180                 185                 190

His Glu His Ile Ala Asn Leu Ala Gly Ser Pro Ala Ile Lys Lys Gly
        195                 200                 205

Ile Leu Gln Thr Val Lys Val Val Asp Glu Leu Val Lys Val Met Gly
    210                 215                 220
```

-continued

Arg His Lys Pro Glu Asn Ile Val Ile Glu Met Ala Arg Glu Asn Gln
225                 230                 235                 240

Thr Thr Gln Lys Gly Gln Lys Asn Ser Arg Glu Arg Met Lys Arg Ile
            245                 250                 255

Glu Glu Gly Ile Lys Glu Leu Gly Ser Gln Ile Leu Lys Glu His Pro
                260                 265                 270

Val Glu Asn Thr Gln Leu Gln Asn Glu Lys Leu Tyr Leu Tyr Tyr Leu
            275                 280                 285

Gln Asn Gly Arg Asp Met Tyr Val Asp Gln Glu Leu Asp Ile Asn Arg
290                 295                 300

Leu Ser Asp Tyr Asp Val Asp His Ile Val Pro Gln Ser Phe Leu Lys
305                 310                 315                 320

Asp Asp Ser Ile Asp Asn Lys Val Leu Thr Arg Ser Asp Lys Asn Arg
                325                 330                 335

Gly Lys Ser Asp Asn Val Pro Ser Glu Glu Val Val Lys Lys Met Lys
                340                 345                 350

Asn Tyr Trp Arg Gln Leu Leu Asn Ala Lys Leu Ile Thr Gln Arg Lys
            355                 360                 365

Phe Asp Asn Leu Thr Lys Ala Glu Arg Gly Gly Leu Ser Glu Leu Asp
370                 375                 380

Lys Ala Gly Phe Ile Lys Arg Gln Leu Val Glu Thr Arg Gln Ile Thr
385                 390                 395                 400

Lys His Val Ala Gln Ile Leu Asp Ser Arg Met Asn Thr Lys Tyr Asp
                405                 410                 415

Glu Asn Asp Lys Leu Ile Arg Glu Val Lys Val Ile Thr Leu Lys Ser
            420                 425                 430

Lys Leu Val Ser Asp Phe Arg Lys Asp Phe Gln Phe Tyr Lys Val Arg
            435                 440                 445

Glu Ile Asn Asn Tyr His His Ala His Asp Ala Tyr Leu Asn Ala Val
450                 455                 460

Val Gly Thr Ala Leu Ile Lys Lys Tyr Pro Lys Leu Glu Ser Glu Phe
465                 470                 475                 480

Val Tyr Gly Asp Tyr Lys Val Tyr Asp Val Arg Lys Met Ile Ala Lys
                485                 490                 495

Ser Glu Gln Glu Ile Gly Lys Ala Thr Ala Lys Tyr Phe Phe Tyr Ser
            500                 505                 510

Asn Ile Met Asn Phe Phe Lys Thr Glu Ile Thr Leu Ala Asn Gly Glu
            515                 520                 525

Ile Arg Lys Arg Pro Leu Ile Glu Thr Asn Gly Glu Thr Gly Glu Ile
530                 535                 540

Val Trp Asp Lys Gly Arg Asp Phe Ala Thr Val Arg Lys Val Leu Ser
545                 550                 555                 560

Met Pro Gln Val Asn Ile Val Lys Lys Thr Glu Val Gln Thr Gly Gly
                565                 570                 575

Phe Ser Lys Glu Ser Ile Leu Pro Lys Arg Asn Ser Asp Lys Leu Ile
            580                 585                 590

Ala Arg Lys Lys Asp Trp Asp Pro Lys Lys Tyr Gly Gly Phe Asp Ser
            595                 600                 605

Pro Thr Val Ala Tyr Ser Val Leu Val Val Ala Lys Val Glu Lys Gly
            610                 615                 620

Lys Ser Lys Lys Leu Lys Ser Val Lys Glu Leu Leu Gly Ile Thr Ile
625                 630                 635                 640

-continued

```
Met Glu Arg Ser Ser Phe Glu Lys Asn Pro Ile Asp Phe Leu Glu Ala
            645                 650                 655

Lys Gly Tyr Lys Glu Val Lys Lys Asp Leu Ile Ile Lys Leu Pro Lys
        660                 665                 670

Tyr Ser Leu Phe Glu Leu Glu Asn Gly Arg Lys Arg Met Leu Ala Ser
            675                 680                 685

Ala Gly Glu Leu Gln Lys Gly Asn Glu Leu Ala Leu Pro Ser Lys Tyr
        690                 695                 700

Val Asn Phe Leu Tyr Leu Ala Ser His Tyr Glu Lys Leu Lys Gly Ser
705                 710                 715                 720

Pro Glu Asp Asn Glu Gln Lys Gln Leu Phe Val Glu Gln His Lys His
                725                 730                 735

Tyr Leu Asp Glu Ile Ile Glu Gln Ile Ser Glu Phe Ser Lys Arg Val
            740                 745                 750

Ile Leu Ala Asp Ala Asn Leu Asp Lys Val Leu Ser Ala Tyr Asn Lys
        755                 760                 765

His Arg Asp Lys Pro Ile Arg Glu Gln Ala Glu Asn Ile Ile His Leu
    770                 775                 780

Phe Thr Leu Thr Asn Leu Gly Ala Pro Ala Ala Phe Lys Tyr Phe Asp
785                 790                 795                 800

Thr Thr Ile Asp Arg Lys Arg Tyr Thr Ser Thr Lys Glu Val Leu Asp
                805                 810                 815

Ala Thr Leu Ile His Gln Ser Ile Thr Gly Leu Tyr Glu Thr Arg Ile
            820                 825                 830

Asp Leu Ser Gln Leu Gly Gly Asp Glu Phe Ala Ser Pro Lys Lys Lys
        835                 840                 845

Arg Lys Val Leu Glu Ser Arg Gly Pro Phe Glu Gly Lys Pro Ile Pro
    850                 855                 860

Asn Pro Leu Leu Gly Leu Asp Ser Thr Arg Thr Gly His His His His
865                 870                 875                 880

His His
```

<210> SEQ ID NO 5
<211> LENGTH: 882
<212> TYPE: PRT
<213> ORGANISM: Artificial Sequence
<220> FEATURE:
<223> OTHER INFORMATION: GS-nMag-GS-C714-NLS

<400> SEQUENCE: 5

```
Met Gly Gly Ser Gly Ser Ser Gly Gly Ser Gly Gly Ser Gly Gly Ser
1               5                   10                  15

Gly His Thr Leu Tyr Ala Pro Gly Gly Tyr Asp Ile Met Gly Tyr Leu
            20                  25                  30

Asp Gln Ile Gly Asn Arg Pro Asn Pro Gln Val Glu Leu Gly Pro Val
        35                  40                  45

Asp Thr Ser Cys Ala Leu Ile Leu Cys Asp Leu Lys Gln Lys Asp Thr
    50                  55                  60

Pro Ile Val Tyr Ala Ser Glu Ala Phe Leu Tyr Met Thr Gly Tyr Ser
65                  70                  75                  80

Asn Ala Glu Val Leu Gly Arg Asn Cys Arg Phe Leu Gln Ser Pro Asp
                85                  90                  95

Gly Met Val Lys Pro Lys Ser Thr Arg Lys Tyr Val Asp Ser Asn Thr
            100                 105                 110

Ile Asn Thr Met Arg Lys Ala Ile Asp Arg Asn Ala Glu Val Gln Val
```

```
            115                 120                 125
Glu Val Val Asn Phe Lys Lys Asn Gly Gln Arg Phe Val Asn Phe Leu
130                 135                 140
Thr Met Ile Pro Val Arg Asp Glu Thr Gly Glu Tyr Arg Tyr Ser Met
145                 150                 155                 160
Gly Phe Gln Cys Glu Thr Glu Gly Gly Ser Gly Gly Ser Gly Gly Gly
                165                 170                 175
Ser Gly Ser Gly Ser Gly Gly Thr Ser Gly Gly Asp Ser Leu
                180                 185                 190
His Glu His Ile Ala Asn Leu Ala Gly Ser Pro Ala Ile Lys Lys Gly
                195                 200                 205
Ile Leu Gln Thr Val Lys Val Val Asp Glu Leu Val Lys Val Met Gly
210                 215                 220
Arg His Lys Pro Glu Asn Ile Val Ile Glu Met Ala Arg Glu Asn Gln
225                 230                 235                 240
Thr Thr Gln Lys Gly Gln Lys Asn Ser Arg Glu Arg Met Lys Arg Ile
                245                 250                 255
Glu Glu Gly Ile Lys Glu Leu Gly Ser Gln Ile Leu Lys Glu His Pro
                260                 265                 270
Val Glu Asn Thr Gln Leu Gln Asn Glu Lys Leu Tyr Leu Tyr Tyr Leu
                275                 280                 285
Gln Asn Gly Arg Asp Met Tyr Val Asp Gln Glu Leu Asp Ile Asn Arg
                290                 295                 300
Leu Ser Asp Tyr Asp Val Asp His Ile Val Pro Gln Ser Phe Leu Lys
305                 310                 315                 320
Asp Asp Ser Ile Asp Asn Lys Val Leu Thr Arg Ser Asp Lys Asn Arg
                325                 330                 335
Gly Lys Ser Asp Asn Val Pro Ser Glu Glu Val Val Lys Lys Met Lys
                340                 345                 350
Asn Tyr Trp Arg Gln Leu Leu Asn Ala Lys Leu Ile Thr Gln Arg Lys
                355                 360                 365
Phe Asp Asn Leu Thr Lys Ala Glu Arg Gly Gly Leu Ser Glu Leu Asp
370                 375                 380
Lys Ala Gly Phe Ile Lys Arg Gln Leu Val Glu Thr Arg Gln Ile Thr
385                 390                 395                 400
Lys His Val Ala Gln Ile Leu Asp Ser Arg Met Asn Thr Lys Tyr Asp
                405                 410                 415
Glu Asn Asp Lys Leu Ile Arg Glu Val Lys Val Ile Thr Leu Lys Ser
                420                 425                 430
Lys Leu Val Ser Asp Phe Arg Lys Asp Phe Gln Phe Tyr Lys Val Arg
                435                 440                 445
Glu Ile Asn Asn Tyr His His Ala His Asp Ala Tyr Leu Asn Ala Val
                450                 455                 460
Val Gly Thr Ala Leu Ile Lys Lys Tyr Pro Lys Leu Glu Ser Glu Phe
465                 470                 475                 480
Val Tyr Gly Asp Tyr Lys Val Tyr Asp Val Arg Lys Met Ile Ala Lys
                485                 490                 495
Ser Glu Gln Glu Ile Gly Lys Ala Thr Ala Lys Tyr Phe Phe Tyr Ser
                500                 505                 510
Asn Ile Met Asn Phe Phe Lys Thr Glu Ile Thr Leu Ala Asn Gly Glu
                515                 520                 525
Ile Arg Lys Arg Pro Leu Ile Glu Thr Asn Gly Glu Thr Gly Glu Ile
                530                 535                 540
```

Val Trp Asp Lys Gly Arg Asp Phe Ala Thr Val Arg Lys Val Leu Ser
545                 550                 555                 560

Met Pro Gln Val Asn Ile Val Lys Lys Thr Glu Val Gln Thr Gly Gly
                565                 570                 575

Phe Ser Lys Glu Ser Ile Leu Pro Lys Arg Asn Ser Asp Lys Leu Ile
            580                 585                 590

Ala Arg Lys Lys Asp Trp Asp Pro Lys Lys Tyr Gly Gly Phe Asp Ser
        595                 600                 605

Pro Thr Val Ala Tyr Ser Val Leu Val Ala Lys Val Glu Lys Gly
    610                 615                 620

Lys Ser Lys Lys Leu Lys Ser Val Lys Glu Leu Leu Gly Ile Thr Ile
625                 630                 635                 640

Met Glu Arg Ser Ser Phe Glu Lys Asn Pro Ile Asp Phe Leu Glu Ala
                645                 650                 655

Lys Gly Tyr Lys Glu Val Lys Lys Asp Leu Ile Ile Lys Leu Pro Lys
            660                 665                 670

Tyr Ser Leu Phe Glu Leu Glu Asn Gly Arg Lys Arg Met Leu Ala Ser
        675                 680                 685

Ala Gly Glu Leu Gln Lys Gly Asn Glu Leu Ala Leu Pro Ser Lys Tyr
    690                 695                 700

Val Asn Phe Leu Tyr Leu Ala Ser His Tyr Glu Lys Leu Lys Gly Ser
705                 710                 715                 720

Pro Glu Asp Asn Glu Gln Lys Gln Leu Phe Val Glu Gln His Lys His
                725                 730                 735

Tyr Leu Asp Glu Ile Ile Glu Gln Ile Ser Glu Phe Ser Lys Arg Val
            740                 745                 750

Ile Leu Ala Asp Ala Asn Leu Asp Lys Val Leu Ser Ala Tyr Asn Lys
        755                 760                 765

His Arg Asp Lys Pro Ile Arg Glu Gln Ala Glu Asn Ile Ile His Leu
    770                 775                 780

Phe Thr Leu Thr Asn Leu Gly Ala Pro Ala Ala Phe Lys Tyr Phe Asp
785                 790                 795                 800

Thr Thr Ile Asp Arg Lys Arg Tyr Thr Ser Thr Lys Glu Val Leu Asp
                805                 810                 815

Ala Thr Leu Ile His Gln Ser Ile Thr Gly Leu Tyr Glu Thr Arg Ile
            820                 825                 830

Asp Leu Ser Gln Leu Gly Gly Asp Glu Phe Ala Ser Pro Lys Lys Lys
        835                 840                 845

Arg Lys Val Leu Glu Ser Arg Gly Pro Phe Glu Gly Lys Pro Ile Pro
    850                 855                 860

Asn Pro Leu Leu Gly Leu Asp Ser Thr Arg Thr Gly His His His His
865                 870                 875                 880

His His

<210> SEQ ID NO 6
<211> LENGTH: 1635
<212> TYPE: DNA
<213> ORGANISM: Artificial Sequence
<220> FEATURE:
<223> OTHER INFORMATION: StopFluc-1

<400> SEQUENCE: 6
atggaagatg ccaaaaacat taagaagggc ccagcgccat tctacccact cgaagacggg     60
accgccggcg agcagctgca caaagccatg aagcgctacg ccctggtgcc cggcaccatc    120

```
gcctttaccg acgcacatat cgaggtggac attacctacg ccgagtactt cgagatgagc    180
gttcggctgg cagaagctat gaagcgctat gggctgaata caaaccatcg gatcgtggtg    240
tgcagcgaga atagcttgca gttcttcatg cccgtgttgg gtgccctgtt catcggtgtg    300
gctgtggccc cagctaacga catctacaac gagcgcgagc tgctgaacag catgggcatc    360
agccagccca ccgtcgtatt cgtgagcaag aaagggctgc aaaagatcct caacgtgcaa    420
aagaagctac cgatcataca aaagatcatc atcatggata gcaagaccga ctaccagggc    480
ttccaaagca tgtacacctt cgtgacttcc catttgccac ccggcttcaa cgagtacgac    540
ttcgtgcccg agagcttcga ccgggacaaa accatcgccc tgatcatgaa cagtagtggc    600
agtaccggat tgcccaaggg cgtagcccta ccgcaccgca ccgcttgtgt ccgattcagt    660
catgcccgcg accccatctt cggcaaccag atcatccccg acaccgctat cctcagcgtg    720
gtgccatttc accacggctt cggcatgttc accacgctgg gctacttgat ctgcggcttt    780
cgggtcgtgc tcatgtaccg cttcgaggag gagctattct tgcgcagctt gcaagactat    840
aagattcaat ctgccctgct ggtgcccaca ctatttagct tcttcgctaa gagcactctc    900
atcgacaagt acgacctaag caacttgcac gagatctaaa gcggcggggc gccgctcagc    960
aaggaggtag gtgaggccgt ggccaaacgc ttccacctac caggcatccg ccagggctac    1020
ggcctgacag aaacaaccag cgccattctg atcaccccccg aaggggacga caagcctggc    1080
gcagtaggca aggtggtgcc cttcttcgag gctaaggtgg tggacttgga caccggtaag    1140
acactgggtg tgaaccagcg cggcgagctg tgcgtccgtg gccccatgat catgagcggc    1200
tacgttaaca accccgaggc tacaaacgct ctcatcgaca aggacggctg gctgcacagc    1260
ggcgacatcg cctactggga cgaggacgag cacttcttca tcgtggaccg gctgaagagc    1320
ctgatcaaat acaagggcta ccaggtagcc ccagccgaac tggagagcat cctgctgcaa    1380 cacccccaaca tcttcgacgc cggggtcgcc ggcctgcccg acgacgatgc cggcgagctg    1440
cccgccgcag tcgtcgtgct ggaacacggt aaaaccatga ccgagaagga gatcgtggac    1500
tatgtggcca gccaggttac aaccgccaag aagctgcgcg gtggtgttgt gttcgtggac    1560
gaggtgccta aggactgac cggcaagttg acgcccgca agatccgcga gattctcatt    1620
aaggccaaga agtaa    1635
```

<210> SEQ ID NO 7
<211> LENGTH: 1635
<212> TYPE: DNA
<213> ORGANISM: Artificial Sequence
<220> FEATURE:
<223> OTHER INFORMATION: StopFluc-2

<400> SEQUENCE: 7

```
atggaagatg ccaaaaacat taagaagggc ccagcgccat tctacccact cgaagacggg    60
accgccggcg agcagctgca caaagccatg aagcgctacg ccctggtgcc cggcaccatc    120
gcctttaccg acgcacatat cgaggtggac attacctacg ccgagtactt cgagatgagc    180
gttcggctgg cagaagctat gaagtaatat gggctgaata caaaccatcg gatcgtggtg    240
tgcagcgaga atagcttgca gttcttcatg cccgtgttgg gtgccctgtt catcggtgtg    300
gctgtggccc cagctaacga catctacaac gagcgcgagc tgctgaacag catgggcatc    360
agccagccca ccgtcgtatt cgtgagcaag aaagggctgc aaaagatcct caacgtgcaa    420
aagaagctac cgatcataca aaagatcatc atcatggata gcaagaccga ctaccagggc    480
```

```
ttccaaagca tgtacacctt cgtgacttcc catttgccac ccggcttcaa cgagtacgac      540
ttcgtgcccg agagcttcga ccgggacaaa accatcgccc tgatcatgaa cagtagtggc      600
agtaccggat tgcccaaggg cgtagcccta ccgcaccgca ccgcttgtgt ccgattcagt      660
catgcccgcg accccatctt cggcaaccag atcatccccg acaccgctat cctcagcgtg      720
gtgccatttc accacggctt cggcatgttc accacgctgg gctacttgat ctgcggcttt      780
cgggtcgtgc tcatgtaccg cttcgaggag gagctattct tgcgcagctt gcaagactat      840
aagattcaat ctgccctgct ggtgcccaca ctatttagct tcttcgctaa gagcactctc      900
atcgacaagt acgacctaag caacttgcac gagatcgcca gcggcggggc gccgctcagc      960
aaggaggtag gtgaggccgt ggccaaacgc ttccacctac caggcatccg ccagggctac      1020
ggcctgacag aaacaaccag cgccattctg atcaccccgg aagggacga caagcctggc      1080 gcagtaggca aggtggtgcc cttcttcgag gctaaggtgg tggacttgga caccggtaag      1140
acactgggtg tgaaccagcg cggcgagctg tgcgtccgtg gccccatgat catgagcggc      1200
tacgttaaca accccgaggc tacaaacgct ctcatcgaca aggacggctg gctgcacagc      1260
ggcgacatcg cctactggga cgaggacgag cacttcttca tcgtggaccg gctgaagagc      1320
ctgatcaaat acaagggcta ccaggtagcc ccagccgaac tggagagcat cctgctgcaa      1380 cacccccaaca tcttcgacgc cggggtcgcc ggcctgcccg acgacgatgc cggcgagctg      1440
cccgccgcag tcgtcgtgct ggaacacggt aaaaccatga ccgagaagga gatcgtggac      1500
tatgtggcca gccaggttac aaccgccaag aagctgcgcg gtggtgttgt gttcgtggac      1560
gaggtgccta aggactgac cggcaagttg acgcccgca agatccgcga gattctcatt      1620
aaggccaaga agtaa                                                      1635

<210> SEQ ID NO 8
<211> LENGTH: 1635
<212> TYPE: DNA
<213> ORGANISM: Artificial Sequence
<220> FEATURE:
<223> OTHER INFORMATION: StopFluc-3

<400> SEQUENCE: 8
atggaagatg ccaaaaacat taagaagggc ccagcgccat tctacccact cgaagacggg      60
accgccggcg agcagctgca caaagccatg aagcgctacg ccctggtgcc cggcaccatc      120
gcctttaccg acgcacatat cgaggtggac attacctacg ccgagtactt cgagatgagc      180
gttcggctgg cagaagctat gaagcgctat gggctgaata caaaccatcg gatcgtggtg      240
tgcagcgaga atagcttgca gttcttcatg cccgtgttgg gtgccctgtt catctaagtg      300
gctgtggccc cagctaacga catctacaac gagcgcgagc tgctgaacag catgggcatc      360
agccagccca ccgtcgtatt cgtgagcaag aaagggctgc aaaagatcct caacgtgcaa      420 agaagctac cgatcataca aaagatcatc atcatggata gcaagaccga ctaccagggc      480
ttccaaagca tgtacacctt cgtgacttcc catttgccac ccggcttcaa cgagtacgac      540
ttcgtgcccg agagcttcga ccgggacaaa accatcgccc tgatcatgaa cagtagtggc      600
agtaccggat tgcccaaggg cgtagcccta ccgcaccgca ccgcttgtgt ccgattcagt      660
catgcccgcg accccatctt cggcaaccag atcatccccg acaccgctat cctcagcgtg      720
gtgccatttc accacggctt cggcatgttc accacgctgg gctacttgat ctgcggcttt      780
cgggtcgtgc tcatgtaccg cttcgaggag gagctattct tgcgcagctt gcaagactat      840
aagattcaat ctgccctgct ggtgcccaca ctatttagct tcttcgctaa gagcactctc      900
```

```
atcgacaagt acgacctaag caacttgcac gagatctaaa gcggcgggc gccgctcagc     960 aaggaggtag gtgaggccgt ggccaaacgc ttccacctac caggcatccg ccagggctac    1020
ggcctgacag aaacaaccag cgccattctg atcaccccg aagggacga caagcctggc     1080 gcagtaggca aggtggtgcc cttcttcgag gctaaggtgg tggacttgga caccggtaag    1140
acactgggtg tgaaccagcg cggcgagctg tgcgtccgtg gccccatgat catgagcggc    1200
tacgttaaca accccgaggc tacaaacgct ctcatcgaca aggacggctg gctgcacagc    1260
ggcgacatcg cctactggga cgaggacgag cacttcttca tcgtggaccg gctgaagagc    1320
ctgatcaaat acaagggcta ccaggtagcc ccagccgaac tggagagcat cctgctgcaa    1380
caccccaaca tcttcgacgc cggggtcgcc ggcctgcccg acgacgatgc cggcgagctg    1440
cccgccgcag tcgtcgtgct ggaacacggt aaaaccatga ccgagaagga gatcgtggac    1500
tatgtggcca gccaggttac aaccgccaag aagctgcgcg tggtgttgt gttcgtggac    1560 gaggtgccta aaggactgac cggcaagttg gacgcccgca agatccgcga gattctcatt    1620
aaggccaaga agtaa                                                     1635
```

<210> SEQ ID NO 9
<211> LENGTH: 914
<212> TYPE: PRT
<213> ORGANISM: Artificial Sequence
<220> FEATURE:
<223> OTHER INFORMATION: NES-dN713-GS-pMag-GS-NES

<400> SEQUENCE: 9

```
Met Gly Leu Pro Pro Leu Glu Arg Leu Thr Leu Gly Ser Asp Lys Lys
1               5                   10                  15

Tyr Ser Ile Gly Leu Ala Ile Gly Thr Asn Ser Val Gly Trp Ala Val
            20                  25                  30

Ile Thr Asp Glu Tyr Lys Val Pro Ser Lys Lys Phe Lys Val Leu Gly
        35                  40                  45

Asn Thr Asp Arg His Ser Ile Lys Lys Asn Leu Ile Gly Ala Leu Leu
    50                  55                  60

Phe Asp Ser Gly Glu Thr Ala Glu Ala Thr Arg Leu Lys Arg Thr Ala
65                  70                  75                  80

Arg Arg Arg Tyr Thr Arg Arg Lys Asn Arg Ile Cys Tyr Leu Gln Glu
                85                  90                  95

Ile Phe Ser Asn Glu Met Ala Lys Val Asp Asp Ser Phe Phe His Arg
            100                 105                 110

Leu Glu Glu Ser Phe Leu Val Glu Glu Asp Lys Lys His Glu Arg His
        115                 120                 125

Pro Ile Phe Gly Asn Ile Val Asp Glu Val Ala Tyr His Glu Lys Tyr
    130                 135                 140

Pro Thr Ile Tyr His Leu Arg Lys Lys Leu Val Asp Ser Thr Asp Lys
145                 150                 155                 160

Ala Asp Leu Arg Leu Ile Tyr Leu Ala Leu Ala His Met Ile Lys Phe
                165                 170                 175

Arg Gly His Phe Leu Ile Glu Gly Asp Leu Asn Pro Asp Asn Ser Asp
            180                 185                 190

Val Asp Lys Leu Phe Ile Gln Leu Val Gln Thr Tyr Asn Gln Leu Phe
        195                 200                 205

Glu Glu Asn Pro Ile Asn Ala Ser Gly Val Asp Ala Lys Ala Ile Leu
    210                 215                 220
```

-continued

```
Ser Ala Arg Leu Ser Lys Ser Arg Arg Leu Glu Asn Leu Ile Ala Gln
225                 230                 235                 240

Leu Pro Gly Glu Lys Lys Asn Gly Leu Phe Gly Asn Leu Ile Ala Leu
                245                 250                 255

Ser Leu Gly Leu Thr Pro Asn Phe Lys Ser Asn Phe Asp Leu Ala Glu
            260                 265                 270

Asp Ala Lys Leu Gln Leu Ser Lys Asp Thr Tyr Asp Asp Asp Leu Asp
        275                 280                 285

Asn Leu Leu Ala Gln Ile Gly Asp Gln Tyr Ala Asp Leu Phe Leu Ala
    290                 295                 300

Ala Lys Asn Leu Ser Asp Ala Ile Leu Leu Ser Asp Ile Leu Arg Val
305                 310                 315                 320

Asn Thr Glu Ile Thr Lys Ala Pro Leu Ser Ala Ser Met Ile Lys Arg
                325                 330                 335

Tyr Asp Glu His His Gln Asp Leu Thr Leu Leu Lys Ala Leu Val Arg
            340                 345                 350

Gln Gln Leu Pro Glu Lys Tyr Lys Glu Ile Phe Phe Asp Gln Ser Lys
        355                 360                 365

Asn Gly Tyr Ala Gly Tyr Ile Asp Gly Gly Ala Ser Gln Glu Glu Phe
    370                 375                 380

Tyr Lys Phe Ile Lys Pro Ile Leu Glu Lys Met Asp Gly Thr Glu Glu
385                 390                 395                 400

Leu Leu Val Lys Leu Asn Arg Glu Asp Leu Leu Arg Lys Gln Arg Thr
                405                 410                 415

Phe Asp Asn Gly Ser Ile Pro His Gln Ile His Leu Gly Glu Leu His
            420                 425                 430

Ala Ile Leu Arg Arg Gln Glu Asp Phe Tyr Pro Phe Leu Lys Asp Asn
        435                 440                 445

Arg Glu Lys Ile Glu Lys Ile Leu Thr Phe Arg Ile Pro Tyr Tyr Val
    450                 455                 460

Gly Pro Leu Ala Arg Gly Asn Ser Arg Phe Ala Trp Met Thr Arg Lys
465                 470                 475                 480

Ser Glu Glu Thr Ile Thr Pro Trp Asn Phe Glu Glu Val Val Asp Lys
                485                 490                 495

Gly Ala Ser Ala Gln Ser Phe Ile Glu Arg Met Thr Asn Phe Asp Lys
            500                 505                 510

Asn Leu Pro Asn Glu Lys Val Leu Pro Lys His Ser Leu Leu Tyr Glu
        515                 520                 525

Tyr Phe Thr Val Tyr Asn Glu Leu Thr Lys Val Lys Tyr Val Thr Glu
    530                 535                 540

Gly Met Arg Lys Pro Ala Phe Leu Ser Gly Glu Gln Lys Lys Ala Ile
545                 550                 555                 560

Val Asp Leu Leu Phe Lys Thr Asn Arg Lys Val Thr Val Lys Gln Leu
                565                 570                 575

Lys Glu Asp Tyr Phe Lys Lys Ile Glu Cys Phe Asp Ser Val Glu Ile
            580                 585                 590

Ser Gly Val Glu Asp Arg Phe Asn Ala Ser Leu Gly Thr Tyr His Asp
        595                 600                 605

Leu Leu Lys Ile Ile Lys Asp Lys Asp Phe Leu Asp Asn Glu Glu Asn
    610                 615                 620

Glu Asp Ile Leu Glu Asp Ile Val Leu Thr Leu Thr Leu Phe Glu Asp
625                 630                 635                 640

Arg Glu Met Ile Glu Glu Arg Leu Lys Thr Tyr Ala His Leu Phe Asp
```

```
            645                 650                 655
Asp Lys Val Met Lys Gln Leu Lys Arg Arg Tyr Thr Gly Trp Gly
            660                 665                 670
Arg Leu Ser Arg Lys Leu Ile Asn Gly Ile Arg Asp Lys Gln Ser Gly
        675                 680                 685
Lys Thr Ile Leu Asp Phe Leu Lys Ser Asp Gly Phe Ala Asn Arg Asn
    690                 695                 700
Phe Met Gln Leu Ile His Asp Asp Ser Leu Thr Phe Lys Glu Asp Ile
705                 710                 715                 720
Gln Lys Ala Gln Val Gly Thr Gly Gly Ser Ser Ser Gly Gly Ser
            725                 730                 735
Gly His Thr Leu Tyr Ala Pro Gly Gly Tyr Asp Ile Met Gly Tyr Leu
        740                 745                 750
Arg Gln Ile Arg Asn Arg Pro Asn Pro Gln Val Glu Leu Gly Pro Val
            755                 760                 765
Asp Thr Ser Cys Ala Leu Ile Leu Cys Asp Leu Lys Gln Lys Asp Thr
770                 775                 780
Pro Ile Val Tyr Ala Ser Glu Ala Phe Leu Tyr Met Thr Gly Tyr Ser
785                 790                 795                 800
Asn Ala Glu Val Leu Gly Arg Asn Cys Arg Phe Leu Gln Ser Pro Asp
                805                 810                 815
Gly Met Val Lys Pro Lys Ser Thr Arg Lys Tyr Val Asp Ser Asn Thr
            820                 825                 830
Ile Asn Thr Met Arg Lys Ala Ile Asp Arg Asn Ala Glu Val Gln Val
        835                 840                 845
Glu Val Val Asn Phe Lys Lys Asn Gly Gln Arg Phe Val Asn Phe Leu
    850                 855                 860
Thr Met Ile Pro Val Arg Asp Glu Thr Gly Glu Tyr Arg Tyr Ser Met
865                 870                 875                 880
Gly Phe Gln Cys Glu Thr Glu Gly Gly Ser Gly Gly Ser Gly Gly Gly
                885                 890                 895
Ser Gly Ser Gly Ser Gly Gly Glu Phe Leu Pro Pro Leu Glu Arg Leu
            900                 905                 910
Thr Leu

<210> SEQ ID NO 10
<211> LENGTH: 925
<212> TYPE: PRT
<213> ORGANISM: Artificial Sequence
<220> FEATURE:
<223> OTHER INFORMATION: GS-nMagHigh1-GS-dC714-GS-NLS-VP64

<400> SEQUENCE: 10

Met Gly Gly Ser Gly Ser Ser Gly Gly Ser Gly Gly Ser Gly Gly Ser
1               5                   10                  15
Gly His Thr Leu Tyr Ala Pro Gly Gly Tyr Asp Ile Met Gly Tyr Leu
            20                  25                  30
Asp Gln Ile Gly Asn Arg Pro Asn Pro Gln Val Glu Leu Gly Pro Val
        35                  40                  45
Asp Thr Ser Cys Ala Leu Ile Leu Cys Asp Leu Lys Gln Lys Asp Thr
    50                  55                  60
Pro Ile Val Tyr Ala Ser Glu Ala Phe Leu Tyr Met Thr Gly Tyr Ser
65                  70                  75                  80
Asn Ala Glu Val Leu Gly Arg Asn Cys Arg Phe Leu Gln Ser Pro Asp
                85                  90                  95
```

-continued

```
Gly Met Val Lys Pro Lys Ser Thr Arg Lys Tyr Val Asp Ser Asn Thr
            100                 105                 110
Ile Asn Thr Ile Arg Lys Ala Ile Asp Arg Asn Ala Glu Val Gln Val
            115                 120                 125
Glu Val Val Asn Phe Lys Lys Asn Gly Gln Arg Phe Val Asn Phe Leu
130                 135                 140
Thr Ile Ile Pro Val Arg Asp Glu Thr Gly Glu Tyr Arg Tyr Ser Met
145                 150                 155                 160
Gly Phe Gln Cys Glu Thr Glu Gly Gly Ser Gly Ser Gly Gly Gly
            165                 170                 175
Ser Gly Ser Gly Ser Gly Gly Thr Ser Gly Gln Gly Asp Ser Leu
            180                 185                 190
His Glu His Ile Ala Asn Leu Ala Gly Ser Pro Ala Ile Lys Lys Gly
            195                 200                 205
Ile Leu Gln Thr Val Lys Val Val Asp Glu Leu Val Lys Val Met Gly
            210                 215                 220
Arg His Lys Pro Glu Asn Ile Val Ile Glu Met Ala Arg Glu Asn Gln
225                 230                 235                 240
Thr Thr Gln Lys Gly Gln Lys Asn Ser Arg Glu Arg Met Lys Arg Ile
            245                 250                 255
Glu Glu Gly Ile Lys Glu Leu Gly Ser Gln Ile Leu Lys Glu His Pro
            260                 265                 270
Val Glu Asn Thr Gln Leu Gln Asn Glu Lys Leu Tyr Leu Tyr Tyr Leu
            275                 280                 285
Gln Asn Gly Arg Asp Met Tyr Val Asp Gln Glu Leu Asp Ile Asn Arg
            290                 295                 300
Leu Ser Asp Tyr Asp Val Asp Ala Ile Val Pro Gln Ser Phe Leu Lys
305                 310                 315                 320
Asp Asp Ser Ile Asp Asn Lys Val Leu Thr Arg Ser Asp Lys Asn Arg
            325                 330                 335
Gly Lys Ser Asp Asn Val Pro Ser Glu Glu Val Val Lys Lys Met Lys
            340                 345                 350
Asn Tyr Trp Arg Gln Leu Leu Asn Ala Lys Leu Ile Thr Gln Arg Lys
            355                 360                 365
Phe Asp Asn Leu Thr Lys Ala Glu Arg Gly Gly Leu Ser Glu Leu Asp
370                 375                 380
Lys Ala Gly Phe Ile Lys Arg Gln Leu Val Glu Thr Arg Gln Ile Thr
385                 390                 395                 400
Lys His Val Ala Gln Ile Leu Asp Ser Arg Met Asn Thr Lys Tyr Asp
            405                 410                 415
Glu Asn Asp Lys Leu Ile Arg Glu Val Lys Val Ile Thr Leu Lys Ser
            420                 425                 430
Lys Leu Val Ser Asp Phe Arg Lys Asp Phe Gln Phe Tyr Lys Val Arg
            435                 440                 445
Glu Ile Asn Asn Tyr His His Ala His Asp Ala Tyr Leu Asn Ala Val
            450                 455                 460
Val Gly Thr Ala Leu Ile Lys Lys Tyr Pro Lys Leu Glu Ser Glu Phe
465                 470                 475                 480
Val Tyr Gly Asp Tyr Lys Val Tyr Asp Val Arg Lys Met Ile Ala Lys
            485                 490                 495
Ser Glu Gln Glu Ile Gly Lys Ala Thr Ala Lys Tyr Phe Phe Tyr Ser
            500                 505                 510
```

```
Asn Ile Met Asn Phe Phe Lys Thr Glu Ile Thr Leu Ala Asn Gly Glu
            515                 520                 525

Ile Arg Lys Arg Pro Leu Ile Glu Thr Asn Gly Glu Thr Gly Glu Ile
        530                 535                 540

Val Trp Asp Lys Gly Arg Asp Phe Ala Thr Val Arg Lys Val Leu Ser
545                 550                 555                 560

Met Pro Gln Val Asn Ile Val Lys Lys Thr Glu Val Gln Thr Gly Gly
                565                 570                 575

Phe Ser Lys Glu Ser Ile Leu Pro Lys Arg Asn Ser Asp Lys Leu Ile
            580                 585                 590

Ala Arg Lys Lys Asp Trp Asp Pro Lys Lys Tyr Gly Gly Phe Asp Ser
        595                 600                 605

Pro Thr Val Ala Tyr Ser Val Leu Val Val Ala Lys Val Glu Lys Gly
        610                 615                 620

Lys Ser Lys Lys Leu Lys Ser Val Lys Glu Leu Leu Gly Ile Thr Ile
625                 630                 635                 640

Met Glu Arg Ser Ser Phe Glu Lys Asn Pro Ile Asp Phe Leu Glu Ala
                645                 650                 655

Lys Gly Tyr Lys Glu Val Lys Lys Asp Leu Ile Ile Lys Leu Pro Lys
                660                 665                 670

Tyr Ser Leu Phe Glu Leu Glu Asn Gly Arg Lys Arg Met Leu Ala Ser
        675                 680                 685

Ala Gly Glu Leu Gln Lys Gly Asn Glu Leu Ala Leu Pro Ser Lys Tyr
        690                 695                 700

Val Asn Phe Leu Tyr Leu Ala Ser His Tyr Glu Lys Leu Lys Gly Ser
705                 710                 715                 720

Pro Glu Asp Asn Glu Gln Lys Gln Leu Phe Val Glu Gln His Lys His
                725                 730                 735

Tyr Leu Asp Glu Ile Ile Glu Gln Ile Ser Glu Phe Ser Lys Arg Val
                740                 745                 750

Ile Leu Ala Asp Ala Asn Leu Asp Lys Val Leu Ser Ala Tyr Asn Lys
            755                 760                 765

His Arg Asp Lys Pro Ile Arg Glu Gln Ala Glu Asn Ile Ile His Leu
770                 775                 780

Phe Thr Leu Thr Asn Leu Gly Ala Pro Ala Ala Phe Lys Tyr Phe Asp
785                 790                 795                 800

Thr Thr Ile Asp Arg Lys Arg Tyr Thr Ser Thr Lys Glu Val Leu Asp
                805                 810                 815

Ala Thr Leu Ile His Gln Ser Ile Thr Gly Leu Tyr Glu Thr Arg Ile
            820                 825                 830

Asp Leu Ser Gln Leu Gly Gly Asp Glu Phe Gly Gly Gly Ser Gly
            835                 840                 845

Gly Gly Gly Ser Gly Gly Gly Ser Gly Pro Lys Lys Lys Arg Lys
        850                 855                 860

Val Ala Ala Ala Gly Ser Gly Arg Ala Asp Ala Leu Asp Asp Phe Asp
865                 870                 875                 880

Leu Asp Met Leu Gly Ser Asp Ala Leu Asp Asp Phe Asp Leu Asp Met
                885                 890                 895

Leu Gly Ser Asp Ala Leu Asp Asp Phe Asp Leu Asp Met Leu Gly Ser
            900                 905                 910

Asp Ala Leu Asp Asp Phe Asp Leu Asp Met Leu Ile Asn
            915                 920                 925
```

```
<210> SEQ ID NO 11
<211> LENGTH: 473
<212> TYPE: PRT
<213> ORGANISM: Artificial Sequence
<220> FEATURE:
<223> OTHER INFORMATION: NLS-GS-MS2-GS-NLS-p65-GS-HSF1

<400> SEQUENCE: 11

Met Gly Pro Lys Lys Lys Arg Lys Val Gly Gly Ser Gly Met Ala Ser
1               5                   10                  15

Asn Phe Thr Gln Phe Val Leu Val Asp Asn Gly Gly Thr Gly Asp Val
            20                  25                  30

Thr Val Ala Pro Ser Asn Phe Ala Asn Gly Ile Ala Glu Trp Ile Ser
        35                  40                  45

Ser Asn Ser Arg Ser Gln Ala Tyr Lys Val Thr Cys Ser Val Arg Gln
    50                  55                  60

Ser Ser Ala Gln Asn Arg Lys Tyr Thr Ile Lys Val Glu Val Pro Lys
65                  70                  75                  80

Gly Ala Trp Arg Ser Tyr Leu Asn Met Glu Leu Thr Ile Pro Ile Phe
                85                  90                  95

Ala Thr Asn Ser Asp Cys Glu Leu Ile Val Lys Ala Met Gln Gly Leu
            100                 105                 110

Leu Lys Asp Gly Asn Pro Ile Pro Ser Ala Ile Ala Ala Asn Ser Gly
        115                 120                 125

Ile Tyr Ala Gly Gly Ser Gly Gly Ser Gly Gly Ser Gly Ser Gly
    130                 135                 140

Ser Gly Ser Gly Pro Lys Lys Lys Arg Lys Val Ala Ala Ala Gly Ser
145                 150                 155                 160

Pro Ser Gly Gln Ile Ser Asn Gln Ala Leu Ala Leu Ala Pro Ser Ser
                165                 170                 175

Ala Pro Val Leu Ala Gln Thr Met Val Pro Ser Ser Ala Met Val Pro
            180                 185                 190

Leu Ala Gln Pro Pro Ala Pro Ala Pro Val Leu Thr Pro Gly Pro Pro
        195                 200                 205

Gln Ser Leu Ser Ala Pro Val Pro Lys Ser Thr Gln Ala Gly Glu Gly
    210                 215                 220

Thr Leu Ser Glu Ala Leu Leu His Leu Gln Phe Asp Ala Asp Glu Asp
225                 230                 235                 240

Leu Gly Ala Leu Leu Gly Asn Ser Thr Asp Pro Gly Val Phe Thr Asp
                245                 250                 255

Leu Ala Ser Val Asp Asn Ser Glu Phe Gln Gln Leu Leu Asn Gln Gly
            260                 265                 270

Val Ser Met Ser His Ser Thr Ala Glu Pro Met Leu Met Glu Tyr Pro
        275                 280                 285

Glu Ala Ile Thr Arg Leu Val Thr Gly Ser Gln Arg Pro Pro Asp Pro
    290                 295                 300

Ala Pro Thr Pro Leu Gly Thr Ser Gly Leu Pro Asn Gly Leu Ser Gly
305                 310                 315                 320

Asp Glu Asp Phe Ser Ser Ile Ala Asp Met Asp Phe Ser Ala Leu Leu
                325                 330                 335

Ser Gln Ile Ser Ser Ser Gly Gln Gly Gly Gly Ser Gly Phe Ser
            340                 345                 350

Val Asp Thr Ser Ala Leu Leu Asp Leu Phe Ser Pro Ser Val Thr Val
        355                 360                 365

Pro Asp Met Ser Leu Pro Asp Leu Asp Ser Ser Leu Ala Ser Ile Gln
```

```
                370             375              380
Glu Leu Leu Ser Pro Gln Glu Pro Arg Pro Pro Glu Ala Glu Asn
385             390             395                 400

Ser Ser Pro Asp Ser Gly Lys Gln Leu Val His Tyr Thr Ala Gln Pro
                405             410             415

Leu Phe Leu Leu Asp Pro Gly Ser Val Asp Thr Gly Ser Asn Asp Leu
            420             425             430

Pro Val Leu Phe Glu Leu Gly Glu Gly Ser Tyr Phe Ser Glu Gly Asp
        435             440             445

Gly Phe Ala Glu Asp Pro Thr Ile Ser Leu Leu Thr Gly Ser Glu Pro
    450             455             460

Pro Lys Ala Lys Asp Pro Thr Val Ser
465             470

<210> SEQ ID NO 12
<211> LENGTH: 23
<212> TYPE: DNA
<213> ORGANISM: Artificial Sequence
<220> FEATURE:
<223> OTHER INFORMATION: StopFluc-1
<220> FEATURE:
<221> NAME/KEY: misc_feature
<222> LOCATION: (22)..(23)
<223> OTHER INFORMATION: n is a, t, g or c

<400> SEQUENCE: 12
aacttgcacg agatctaaag cnn                                              23

<210> SEQ ID NO 13
<211> LENGTH: 23
<212> TYPE: DNA
<213> ORGANISM: Artificial Sequence
<220> FEATURE:
<223> OTHER INFORMATION: StopFluc-2
<220> FEATURE:
<221> NAME/KEY: misc_feature
<222> LOCATION: (22)..(23)
<223> OTHER INFORMATION: n is a, t, g or c

<400> SEQUENCE: 13
gcagaagcta tgaagtaata tnn                                              23

<210> SEQ ID NO 14
<211> LENGTH: 21
<212> TYPE: DNA
<213> ORGANISM: Artificial Sequence
<220> FEATURE:
<223> OTHER INFORMATION: sgRNA(StopFluc-1)

<400> SEQUENCE: 14
gaacttgcac gagatctaaa g                                                21

<210> SEQ ID NO 15
<211> LENGTH: 20
<212> TYPE: DNA
<213> ORGANISM: Artificial Sequence
<220> FEATURE:
<223> OTHER INFORMATION: sgRNA(StopFluc-2)

<400> SEQUENCE: 15
gcagaagcta tgaagtaata                                                  20

<210> SEQ ID NO 16
<211> LENGTH: 20
```

```
<212> TYPE: DNA
<213> ORGANISM: Artificial Sequence
<220> FEATURE:
<223> OTHER INFORMATION: sgRNA(StopFluc-3)

<400> SEQUENCE: 16
gggtgccctg ttcatctaag                                              20

<210> SEQ ID NO 17
<211> LENGTH: 38
<212> TYPE: DNA
<213> ORGANISM: Homo sapiens

<400> SEQUENCE: 17
tatgacatca attattatac atcggagccc tgccaaaa                          38

<210> SEQ ID NO 18
<211> LENGTH: 37
<212> TYPE: DNA
<213> ORGANISM: Artificial Sequence
<220> FEATURE:
<223> OTHER INFORMATION: 1 bp deletion of human CCR5 locus

<400> SEQUENCE: 18
tatgacatca attattatca tcggagccct gccaaaa                           37

<210> SEQ ID NO 19
<211> LENGTH: 36
<212> TYPE: DNA
<213> ORGANISM: Artificial Sequence
<220> FEATURE:
<223> OTHER INFORMATION: 2bp deletion of human CCR5 locus

<400> SEQUENCE: 19
tatgacatca attattacat cggagccctg ccaaaa                            36

<210> SEQ ID NO 20
<211> LENGTH: 34
<212> TYPE: DNA
<213> ORGANISM: Artificial Sequence
<220> FEATURE:
<223> OTHER INFORMATION: 4bp deletion of human CCR5 locus

<400> SEQUENCE: 20
tatgacatca attattatcg gagccctgcc aaaa                              34

<210> SEQ ID NO 21
<211> LENGTH: 28
<212> TYPE: DNA
<213> ORGANISM: Artificial Sequence
<220> FEATURE:
<223> OTHER INFORMATION: 10bp deletion of human CCR5 locus

<400> SEQUENCE: 21
tatgacatca attattatac tgccaaaa                                     28

<210> SEQ ID NO 22
<211> LENGTH: 25
<212> TYPE: DNA
<213> ORGANISM: Artificial Sequence
<220> FEATURE:
<223> OTHER INFORMATION: 13bp deletion of human CCR5 locus

<400> SEQUENCE: 22
tatgacatca agagccctgc caaaa                                        25
```

```
<210> SEQ ID NO 23
<211> LENGTH: 24
<212> TYPE: DNA
<213> ORGANISM: Artificial Sequence
<220> FEATURE:
<223> OTHER INFORMATION: 14bp deletion of human CCR5 locus

<400> SEQUENCE: 23
tatgacatcg gagccctgcc aaaa                                             24

<210> SEQ ID NO 24
<211> LENGTH: 38
<212> TYPE: DNA
<213> ORGANISM: Homo sapiens

<400> SEQUENCE: 24
gaagggcctg agtccgagca gaagaagaag ggctccca                              38

<210> SEQ ID NO 25
<211> LENGTH: 38
<212> TYPE: DNA
<213> ORGANISM: Homo sapiens

<400> SEQUENCE: 25
cttcccggac tcaggctcgt cttcttcttc ccgagggt                              38

<210> SEQ ID NO 26
<211> LENGTH: 30
<212> TYPE: DNA
<213> ORGANISM: Artificial Sequence
<220> FEATURE:
<223> OTHER INFORMATION: ssODN 96 mer

<400> SEQUENCE: 26
tgagtccgag cagaagaagc ttaagggctc                                       30

<210> SEQ ID NO 27
<211> LENGTH: 77
<212> TYPE: DNA
<213> ORGANISM: Homo sapiens

<400> SEQUENCE: 27
agaaccggag gacaaagtac aaacggcaga agctggagga ggaagggcct gagtccgagc      60
agaagaagaa gggctcc                                                     77

<210> SEQ ID NO 28
<211> LENGTH: 77
<212> TYPE: DNA
<213> ORGANISM: Homo sapiens

<400> SEQUENCE: 28
tcttggcctc ctgtttcatg tttgccgtct tcgacctcct ccttcccgga ctcaggctcg      60
tcttcttctt cccgagg                                                     77

<210> SEQ ID NO 29
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 29
gaacttgcac gagatctaaa g                                                21
```

<210> SEQ ID NO 30
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 30
gaacttgcac gagatctaaa c                                             21

<210> SEQ ID NO 31
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 31
gaacttgcac gagatctaat g                                             21

<210> SEQ ID NO 32
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 32
gaacttgcac gagatctata g                                             21

<210> SEQ ID NO 33
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 33
gaacttgcac gagatcttaa g                                             21

<210> SEQ ID NO 34
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 34
gaacttgcac gagatcaaaa g                                             21

<210> SEQ ID NO 35
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 35
gaacttgcac gagatgtaaa g                                             21

<210> SEQ ID NO 36
<211> LENGTH: 21
<212> TYPE: DNA
<213> ORGANISM: Artificial Sequence
<220> FEATURE:

```
-continued

<223> OTHER INFORMATION: Guide sequence of sgRNA

<400> SEQUENCE: 36
gaacttgcac gagaactaaa g                                              21

<210> SEQ ID NO 37
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 37
gaacttgcac gagttctaaa g                                              21

<210> SEQ ID NO 38
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 38
gaacttgcac gacatctaaa g                                              21

<210> SEQ ID NO 39
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 39
gaacttgcac gtgatctaaa g                                              21

<210> SEQ ID NO 40
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 40
gaacttgcac cagatctaaa g                                              21

<210> SEQ ID NO 41
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 41
gaacttgcag gagatctaaa g                                              21

<210> SEQ ID NO 42
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 42
gaacttgctc gagatctaaa g                                              21
```

<210> SEQ ID NO 43
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 43
gaacttggac gagatctaaa g                                            21

<210> SEQ ID NO 44
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 44
gaacttccac gagatctaaa g                                            21

<210> SEQ ID NO 45
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 45
gaactagcac gagatctaaa g                                            21

<210> SEQ ID NO 46
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 46
gaacatgcac gagatctaaa g                                            21

<210> SEQ ID NO 47
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 47
gaagttgcac gagatctaaa g                                            21

<210> SEQ ID NO 48
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 48
gatcttgcac gagatctaaa g                                            21

<210> SEQ ID NO 49
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 49
gtacttgcac gagatctaaa g                                              21

<210> SEQ ID NO 50
<211> LENGTH: 25
<212> TYPE: DNA
<213> ORGANISM: Artificial Sequence
<220> FEATURE:
<223> OTHER INFORMATION: Oligonucleotide for top strand

<400> SEQUENCE: 50
caccgaactt gcacgagatc taaag                                          25

<210> SEQ ID NO 51
<211> LENGTH: 25
<212> TYPE: DNA
<213> ORGANISM: Artificial Sequence
<220> FEATURE:
<223> OTHER INFORMATION: Oligonucleotide for top strand

<400> SEQUENCE: 51
caccgaactt gcacgagatc taaac                                          25

<210> SEQ ID NO 52
<211> LENGTH: 25
<212> TYPE: DNA
<213> ORGANISM: Artificial Sequence
<220> FEATURE:
<223> OTHER INFORMATION: Oligonucleotide for top strand

<400> SEQUENCE: 52
caccgaactt gcacgagatc taatg                                          25

<210> SEQ ID NO 53
<211> LENGTH: 25
<212> TYPE: DNA
<213> ORGANISM: Artificial Sequence
<220> FEATURE:
<223> OTHER INFORMATION: Oligonucleotide for top strand

<400> SEQUENCE: 53
caccgaactt gcacgagatc tatag                                          25

<210> SEQ ID NO 54
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 54
caccgaactt gcacgagatc ttaag                                          25

<210> SEQ ID NO 55
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 55
caccgaactt gcacgagatc aaaag                                          25

<210> SEQ ID NO 56
<211> LENGTH: 25

```
<212> TYPE: DNA
<213> ORGANISM: Artificial Sequence
<220> FEATURE:
<223> OTHER INFORMATION: Guide sequence of sgRNA

<400> SEQUENCE: 56
caccgaactt gcacgagatg taaag                                              25

<210> SEQ ID NO 57
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 57
caccgaactt gcacgagaac taaag                                              25

<210> SEQ ID NO 58
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 58
caccgaactt gcacgagttc taaag                                              25

<210> SEQ ID NO 59
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 59
caccgaactt gcacgacatc taaag                                              25

<210> SEQ ID NO 60
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 60
caccgaactt gcacgtgatc taaag                                              25

<210> SEQ ID NO 61
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 61
caccgaactt gcaccagatc taaag                                              25

<210> SEQ ID NO 62
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 62
```
caccgaactt gcaggagatc taaag                                    25

<210> SEQ ID NO 63
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 63
caccgaactt gctcgagatc taaag                                    25

<210> SEQ ID NO 64
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 64
caccgaactt ggacgagatc taaag                                    25

<210> SEQ ID NO 65
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 65
caccgaactt ccacgagatc taaag                                    25

<210> SEQ ID NO 66
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 66
caccgaacta gcacgagatc taaag                                    25

<210> SEQ ID NO 67
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 67
caccgaacat gcacgagatc taaag                                    25

<210> SEQ ID NO 68
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 68
caccgaagtt gcacgagatc taaag                                    25

<210> SEQ ID NO 69
<211> LENGTH: 25
<212> TYPE: DNA
<213> ORGANISM: Artificial Sequence

```
<220> FEATURE:
<223> OTHER INFORMATION: Guide sequence of sgRNA

<400> SEQUENCE: 69
caccgatctt gcacgagatc taaag                                              25

<210> SEQ ID NO 70
<211> LENGTH: 25
<212> TYPE: DNA
<213> ORGANISM: Artificial Sequence
<220> FEATURE:
<223> OTHER INFORMATION: Guide sequence of sgRNA

<400> SEQUENCE: 70
caccgtactt gcacgagatc taaag                                              25

<210> SEQ ID NO 71
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 71 aaaccttttag atctcgtgca agttc                                             25

<210> SEQ ID NO 72
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 72
aaacgtttag atctcgtgca agttc                                              25

<210> SEQ ID NO 73
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 73
aaaccattag atctcgtgca agttc                                              25

<210> SEQ ID NO 74
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 74
aaacctatag atctcgtgca agttc                                              25

<210> SEQ ID NO 75
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 75
aaaccttaag atctcgtgca agttc                                              25
```

```
<210> SEQ ID NO 76
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 76
aaacctttTg atctcgtgca agttc                                              25

<210> SEQ ID NO 77
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 77
aaaccTttac atctcgtgca agttc                                              25

<210> SEQ ID NO 78
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 78
aaaccTttag ttctcgtgca agttc                                              25

<210> SEQ ID NO 79
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 79
aaaccTttag aactcgtgca agttc                                              25

<210> SEQ ID NO 80
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 80
aaaccTttag atgtcgtgca agttc                                              25

<210> SEQ ID NO 81
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 81
aaaccTttag atcacgtgca agttc                                              25

<210> SEQ ID NO 82
<211> LENGTH: 25
<212> TYPE: DNA
<213> ORGANISM: Artificial Sequence
<220> FEATURE:
<223> OTHER INFORMATION: Oligonucleotide for bottom strand
```

```
<400> SEQUENCE: 82
aaacctttag atctggtgca agttc                                          25

<210> SEQ ID NO 83
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 83
aaacctttag atctcctgca agttc                                          25

<210> SEQ ID NO 84
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 84
aaacctttag atctcgagca agttc                                          25

<210> SEQ ID NO 85
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 85
aaacctttag atctcgtcca agttc                                          25

<210> SEQ ID NO 86
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 86
aaacctttag atctcgtgga agttc                                          25

<210> SEQ ID NO 87
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 87
aaacctttag atctcgtgct agttc                                          25

<210> SEQ ID NO 88
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 88
aaacctttag atctcgtgca tgttc                                          25

<210> SEQ ID NO 89
```

```
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 89
aaacctttag atctcgtgca acttc                                     25

<210> SEQ ID NO 90
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 90
aaacctttag atctcgtgca agatc                                     25

<210> SEQ ID NO 91
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 91
aaacctttag atctcgtgca agtac                                     25

<210> SEQ ID NO 92
<211> LENGTH: 20
<212> TYPE: DNA
<213> ORGANISM: Artificial Sequence
<220> FEATURE:
<223> OTHER INFORMATION: Oligonucleotide for bottom strand

<400> SEQUENCE: 92
gcagaagcta tgaagtaata                                           20

<210> SEQ ID NO 93
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 93
gcagaagcta tgaagtaatt                                           20

<210> SEQ ID NO 94
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 94
gcagaagcta tgaagtaaaa                                           20

<210> SEQ ID NO 95
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 95
```
gcagaagcta tgaagtatta                                           20

<210> SEQ ID NO 96
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 96
gcagaagcta tgaagttata                                           20

<210> SEQ ID NO 97
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 97
gcagaagcta tgaagaaata                                           20

<210> SEQ ID NO 98
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 98
gcagaagcta tgaactaata                                           20

<210> SEQ ID NO 99
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 99
gcagaagcta tgatgtaata                                           20

<210> SEQ ID NO 100
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 100
gcagaagcta tgtagtaata                                           20

<210> SEQ ID NO 101
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 101
gcagaagcta tcaagtaata                                           20

<210> SEQ ID NO 102
<211> LENGTH: 20
<212> TYPE: DNA

```
<213> ORGANISM: Artificial Sequence
<220> FEATURE:
<223> OTHER INFORMATION: Guide sequence of sgRNA

<400> SEQUENCE: 102
gcagaagcta agaagtaata                                                  20

<210> SEQ ID NO 103
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 103
gcagaagctt tgaagtaata                                                  20

<210> SEQ ID NO 104
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 104
gcagaagcaa tgaagtaata                                                  20

<210> SEQ ID NO 105
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 105
gcagaaggta tgaagtaata                                                  20

<210> SEQ ID NO 106
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 106
gcagaaccta tgaagtaata                                                  20

<210> SEQ ID NO 107
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 107
gcagatgcta tgaagtaata                                                  20

<210> SEQ ID NO 108
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 108
gcagtagcta tgaagtaata                                                  20
```

```
<210> SEQ ID NO 109
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 109
gcacaagcta tgaagtaata                                              20

<210> SEQ ID NO 110
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 110
gctgaagcta tgaagtaata                                              20

<210> SEQ ID NO 111
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 111
ggagaagcta tgaagtaata                                              20

<210> SEQ ID NO 112
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 112
caccgcagaa gctatgaagt aata                                         24

<210> SEQ ID NO 113
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 113
caccgcagaa gctatgaagt aatt                                         24

<210> SEQ ID NO 114
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 114
caccgcagaa gctatgaagt aaaa                                         24

<210> SEQ ID NO 115
<211> LENGTH: 24
<212> TYPE: DNA
<213> ORGANISM: Artificial Sequence
<220> FEATURE:
```

```
<223> OTHER INFORMATION: Oligonucleotide for top strand

<400> SEQUENCE: 115
caccgcagaa gctatgaagt atta                                    24

<210> SEQ ID NO 116
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 116
caccgcagaa gctatgaagt tata                                    24

<210> SEQ ID NO 117
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 117
caccgcagaa gctatgaaga aata                                    24

<210> SEQ ID NO 118
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 118
caccgcagaa gctatgaact aata                                    24

<210> SEQ ID NO 119
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 119
caccgcagaa gctatgatgt aata                                    24

<210> SEQ ID NO 120
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 120
caccgcagaa gctatgtagt aata                                    24

<210> SEQ ID NO 121
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 121
caccgcagaa gctatcaagt aata                                    24
```

-continued

```
<210> SEQ ID NO 122
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 122
caccgcagaa gctaagaagt aata                                              24

<210> SEQ ID NO 123
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 123
caccgcagaa gctttgaagt aata                                              24

<210> SEQ ID NO 124
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 124
caccgcagaa gcaatgaagt aata                                              24

<210> SEQ ID NO 125
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 125
caccgcagaa ggtatgaagt aata                                              24

<210> SEQ ID NO 126
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 126
caccgcagaa cctatgaagt aata                                              24

<210> SEQ ID NO 127
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 127
caccgcagat gctatgaagt aata                                              24

<210> SEQ ID NO 128
<211> LENGTH: 24
<212> TYPE: DNA
<213> ORGANISM: Artificial Sequence
<220> FEATURE:
<223> OTHER INFORMATION: Oligonucleotide for top strand
```

```
<400> SEQUENCE: 128
caccgcagta gctatgaagt aata                                              24

<210> SEQ ID NO 129
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 129
caccgcacaa gctatgaagt aata                                              24

<210> SEQ ID NO 130
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 130
caccgctgaa gctatgaagt aata                                              24

<210> SEQ ID NO 131
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 131
caccggagaa gctatgaagt aata                                              24

<210> SEQ ID NO 132
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 132
aaactattac ttcatagctt ctgc                                              24

<210> SEQ ID NO 133
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 133
aaacaattac ttcatagctt ctgc                                              24

<210> SEQ ID NO 134
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 134 aaactttttac ttcatagctt ctgc                                             24

<210> SEQ ID NO 135
<211> LENGTH: 24
```

```
<212> TYPE: DNA
<213> ORGANISM: Artificial Sequence
<220> FEATURE:
<223> OTHER INFORMATION: Oligonucleotide for bottom strand

<400> SEQUENCE: 135
aaactaatac ttcatagctt ctgc                                              24

<210> SEQ ID NO 136
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 136
aaactataac ttcatagctt ctgc                                              24

<210> SEQ ID NO 137
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 137
aaactatttc ttcatagctt ctgc                                              24

<210> SEQ ID NO 138
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 138
aaactattag ttcatagctt ctgc                                              24

<210> SEQ ID NO 139
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 139
aaactattac atcatagctt ctgc                                              24

<210> SEQ ID NO 140
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 140
aaactattac tacatagctt ctgc                                              24

<210> SEQ ID NO 141
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 141
```
aaactattac ttgatagctt ctgc                                              24

<210> SEQ ID NO 142
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 142
aaactattac ttcttagctt ctgc                                              24

<210> SEQ ID NO 143
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 143
aaactattac ttcaaagctt ctgc                                              24

<210> SEQ ID NO 144
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 144
aaactattac ttcattgctt ctgc                                              24

<210> SEQ ID NO 145
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 145
aaactattac ttcatacctt ctgc                                              24

<210> SEQ ID NO 146
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 146
aaactattac ttcataggtt ctgc                                              24

<210> SEQ ID NO 147
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 147
aaactattac ttcatagcat ctgc                                              24

<210> SEQ ID NO 148
<211> LENGTH: 24
<212> TYPE: DNA
<213> ORGANISM: Artificial Sequence

```
<220> FEATURE:
<223> OTHER INFORMATION: Oligonucleotide for bottom strand

<400> SEQUENCE: 148
aaactattac ttcatagcta ctgc                                          24

<210> SEQ ID NO 149
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 149
aaactattac ttcatagctt gtgc                                          24

<210> SEQ ID NO 150
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 150
aaactattac ttcatagctt cagc                                          24

<210> SEQ ID NO 151
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 151
aaactattac ttcatagctt ctcc                                          24

<210> SEQ ID NO 152
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 152
gggtgccctg ttcatctaag                                               20

<210> SEQ ID NO 153
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 153
gggtgccctg ttcatctaac                                               20

<210> SEQ ID NO 154
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 154
gggtgccctg ttcatctatg                                               20
```

```
<210> SEQ ID NO 155
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 155
gggtgccctg ttcatcttag                                               20

<210> SEQ ID NO 156
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 156
gggtgccctg ttcatcaaag                                               20

<210> SEQ ID NO 157
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 157
gggtgccctg ttcatgtaag                                               20

<210> SEQ ID NO 158
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 158
gggtgccctg ttcaactaag                                               20

<210> SEQ ID NO 159
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 159
gggtgccctg ttcttctaag                                               20

<210> SEQ ID NO 160
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 160
gggtgccctg ttgatctaag                                               20

<210> SEQ ID NO 161
<211> LENGTH: 20
<212> TYPE: DNA
<213> ORGANISM: Artificial Sequence
<220> FEATURE:
<223> OTHER INFORMATION: Guide sequence of sgRNA
```

<400> SEQUENCE: 161
gggtgccctg tacatctaag                                          20

<210> SEQ ID NO 162
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 162
gggtgccctg atcatctaag                                          20

<210> SEQ ID NO 163
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 163
gggtgccctc ttcatctaag                                          20

<210> SEQ ID NO 164
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 164
gggtgcccag ttcatctaag                                          20

<210> SEQ ID NO 165
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 165
gggtgccgtg ttcatctaag                                          20

<210> SEQ ID NO 166
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 166
gggtgcgctg ttcatctaag                                          20

<210> SEQ ID NO 167
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 167
gggtggcctg ttcatctaag                                          20

<210> SEQ ID NO 168

```
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 168
gggtcccctg ttcatctaag                                              20

<210> SEQ ID NO 169
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 169
gggagccctg ttcatctaag                                              20

<210> SEQ ID NO 170
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 170
ggctgccctg ttcatctaag                                              20

<210> SEQ ID NO 171
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 171
gcgtgccctg ttcatctaag                                              20

<210> SEQ ID NO 172
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 172
caccgggtgc cctgttcatc taag                                         24

<210> SEQ ID NO 173
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 173
caccgggtgc cctgttcatc taac                                         24

<210> SEQ ID NO 174
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 174
```

```
caccgggtgc cctgttcatc tatg                                              24
```

<210> SEQ ID NO 175
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 175

```
caccgggtgc cctgttcatc ttag                                              24
```

<210> SEQ ID NO 176
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 176

```
caccgggtgc cctgttcatc aaag                                              24
```

<210> SEQ ID NO 177
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 177

```
caccgggtgc cctgttcatg taag                                              24
```

<210> SEQ ID NO 178
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 178

```
caccgggtgc cctgttcaac taag                                              24
```

<210> SEQ ID NO 179
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 179

```
caccgggtgc cctgttcttc taag                                              24
```

<210> SEQ ID NO 180
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 180

```
caccgggtgc cctgttgatc taag                                              24
```

<210> SEQ ID NO 181
<211> LENGTH: 24
<212> TYPE: DNA

<213> ORGANISM: Artificial Sequence
<220> FEATURE:
<223> OTHER INFORMATION: Oligonucleotide for top strand

<400> SEQUENCE: 181
caccgggtgc cctgtacatc taag                                    24

<210> SEQ ID NO 182
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 182
caccgggtgc cctgatcatc taag                                    24

<210> SEQ ID NO 183
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 183
caccgggtgc cctcttcatc taag                                    24

<210> SEQ ID NO 184
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 184
caccgggtgc ccagttcatc taag                                    24

<210> SEQ ID NO 185
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 185
caccgggtgc cgtgttcatc taag                                    24

<210> SEQ ID NO 186
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 186
caccgggtgc gctgttcatc taag                                    24

<210> SEQ ID NO 187
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 187
caccgggtgg cctgttcatc taag                                    24

```
<210> SEQ ID NO 188
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 188
caccgggtcc cctgttcatc taag                                    24

<210> SEQ ID NO 189
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 189
caccgggagc cctgttcatc taag                                    24

<210> SEQ ID NO 190
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 190
caccggctgc cctgttcatc taag                                    24

<210> SEQ ID NO 191
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 191
caccgcgtgc cctgttcatc taag                                    24

<210> SEQ ID NO 192
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 192
aaaccttaga tgaacagggc accc                                    24

<210> SEQ ID NO 193
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 193
aaacgttaga tgaacagggc accc                                    24

<210> SEQ ID NO 194
<211> LENGTH: 24
<212> TYPE: DNA
<213> ORGANISM: Artificial Sequence
<220> FEATURE:
```

<223> OTHER INFORMATION: Oligonucleotide for bottom strand

<400> SEQUENCE: 194
aaaccataga tgaacagggc accc                                24

<210> SEQ ID NO 195
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 195
aaacctaaga tgaacagggc accc                                24

<210> SEQ ID NO 196
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 196
aaacctttga tgaacagggc accc                                24

<210> SEQ ID NO 197
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 197
aaaccttaca tgaacagggc accc                                24

<210> SEQ ID NO 198
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 198
aaaccttagt tgaacagggc accc                                24

<210> SEQ ID NO 199
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 199
aaaccttaga agaacagggc accc                                24

<210> SEQ ID NO 200
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 200
aaaccttaga tcaacagggc accc                                24

```
<210> SEQ ID NO 201
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 201
aaaccttaga tgtacagggc accc                                          24

<210> SEQ ID NO 202
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 202
aaaccttaga tgatcagggc accc                                          24

<210> SEQ ID NO 203
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 203
aaaccttaga tgaagagggc accc                                          24

<210> SEQ ID NO 204
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 204
aaaccttaga tgaactgggc accc                                          24

<210> SEQ ID NO 205
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 205
aaaccttaga tgaacacggc accc                                          24

<210> SEQ ID NO 206
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 206
aaaccttaga tgaacagcgc accc                                          24

<210> SEQ ID NO 207
<211> LENGTH: 24
<212> TYPE: DNA
<213> ORGANISM: Artificial Sequence
<220> FEATURE:
<223> OTHER INFORMATION: Oligonucleotide for bottom strand
```

<400> SEQUENCE: 207
aaaccttaga tgaacaggcc accc                                        24

<210> SEQ ID NO 208
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 208
aaaccttaga tgaacagggg accc                                        24

<210> SEQ ID NO 209
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 209
aaaccttaga tgaacagggc tccc                                        24

<210> SEQ ID NO 210
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 210
aaaccttaga tgaacagggc agcc                                        24

<210> SEQ ID NO 211
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 211
aaaccttaga tgaacagggc acgc                                        24

<210> SEQ ID NO 212
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 212
gtgacatcaa ttattataca t                                           21

<210> SEQ ID NO 213
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 213
gagtccgagc agaagaagaa                                             20

<210> SEQ ID NO 214
<211> LENGTH: 20

```
<212> TYPE: DNA
<213> ORGANISM: Artificial Sequence
<220> FEATURE:
<223> OTHER INFORMATION: Guide sequence of sgRNA

<400> SEQUENCE: 214
gccgtttgta ctttgtcctc                                              20

<210> SEQ ID NO 215
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 215
ggtgagtgag tgtgtgcgtg                                              20

<210> SEQ ID NO 216
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 216
gctccctccc aggatcctct c                                            21

<210> SEQ ID NO 217
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 217
gtttgtgcag ctgctcgccg                                              20

<210> SEQ ID NO 218
<211> LENGTH: 20
<212> TYPE: DNA
<213> ORGANISM: Artificial Sequence
<220> FEATURE:
<223> OTHER INFORMATION: Guide sequence of sgRNA

<400> SEQUENCE: 218
gtccacctcg atatgtgcgt                                              20

<210> SEQ ID NO 219
<211> LENGTH: 21
<212> TYPE: DNA
<213> ORGANISM: Artificial Sequence
<220> FEATURE:
<223> OTHER INFORMATION: Guide sequence of sgRNA

<400> SEQUENCE: 219
gcgctgcaca ccacgatccg a                                            21

<210> SEQ ID NO 220
<211> LENGTH: 18
<212> TYPE: DNA
<213> ORGANISM: Artificial Sequence
<220> FEATURE:
<223> OTHER INFORMATION: Guide sequence of sgRNA

<400> SEQUENCE: 220
```

```
gggtcttcga gaagacct                                           18
```

<210> SEQ ID NO 221
<211> LENGTH: 25
<212> TYPE: DNA
<213> ORGANISM: Artificial Sequence
<220> FEATURE:
<223> OTHER INFORMATION: Oligonucleotide for top strand

<400> SEQUENCE: 221

```
caccgtgaca tcaattatta tacat                                   25
```

<210> SEQ ID NO 222
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 222

```
caccgagtcc gagcagaaga agaa                                    24
```

<210> SEQ ID NO 223
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 223

```
caccgccgtt tgtactttgt cctc                                    24
```

<210> SEQ ID NO 224
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 224

```
caccggtgag tgagtgtgtg cgtg                                    24
```

<210> SEQ ID NO 225
<211> LENGTH: 25
<212> TYPE: DNA
<213> ORGANISM: Artificial Sequence
<220> FEATURE:
<223> OTHER INFORMATION: Oligonucleotide for top strand

<400> SEQUENCE: 225

```
caccgctccc tcccaggatc ctctc                                   25
```

<210> SEQ ID NO 226
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 226

```
caccgggagg gagagcttgg cagg                                    24
```

<210> SEQ ID NO 227
<211> LENGTH: 25
<212> TYPE: DNA
<213> ORGANISM: Artificial Sequence

```
<220> FEATURE:
<223> OTHER INFORMATION: Oligonucleotide for top strand

<400> SEQUENCE: 227
caccgtttgt gcagctgctc gccgg                                    25

<210> SEQ ID NO 228
<211> LENGTH: 24
<212> TYPE: DNA
<213> ORGANISM: Artificial Sequence
<220> FEATURE:
<223> OTHER INFORMATION: Oligonucleotide for top strand

<400> SEQUENCE: 228
caccgtccac ctcgatatgt gcgt                                     24

<210> SEQ ID NO 229
<211> LENGTH: 25
<212> TYPE: DNA
<213> ORGANISM: Artificial Sequence
<220> FEATURE:
<223> OTHER INFORMATION: Oligonucleotide for top strand

<400> SEQUENCE: 229
caccgcgctg cacaccacga tccga                                    25

<210> SEQ ID NO 230
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 230
aaacatgtat aataattgat gtcac                                    25

<210> SEQ ID NO 231
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 231
aaacttcttc ttctgctcgg actc                                     24

<210> SEQ ID NO 232
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 232
aaacgaggac aaagtacaaa cggc                                     24

<210> SEQ ID NO 233
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 233
aaaccacgca cacactcact cacc                                     24
```

<210> SEQ ID NO 234
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 234
aaacgagagg atcctgggag ggagc                                            25

<210> SEQ ID NO 235
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 235
aaaccctgcc aagctctccc tccc                                             24

<210> SEQ ID NO 236
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 236
aaacccggcg agcagctgca caaac                                            25

<210> SEQ ID NO 237
<211> LENGTH: 24
<212> TYPE: DNA
<213> ORGANISM: Artificial Sequence
<220> FEATURE:
<223> OTHER INFORMATION: Oligonucleotide for bottom strand

<400> SEQUENCE: 237
aaacacgcac atatcgaggt ggac                                             24

<210> SEQ ID NO 238
<211> LENGTH: 25
<212> TYPE: DNA
<213> ORGANISM: Artificial Sequence
<220> FEATURE:
<223> OTHER INFORMATION: Oligonucleotide for bottom strand

<400> SEQUENCE: 238
aaactcggat cgtggtgtgc agcgc                                            25

<210> SEQ ID NO 239
<211> LENGTH: 33
<212> TYPE: DNA
<213> ORGANISM: Artificial Sequence
<220> FEATURE:
<223> OTHER INFORMATION: Guide sequence of sgRNA

<400> SEQUENCE: 239
aacttgcacg agatctaaag cggcggggcg ccg                                   33

<210> SEQ ID NO 240
<211> LENGTH: 33
<212> TYPE: DNA
<213> ORGANISM: Artificial Sequence
<220> FEATURE:
<223> OTHER INFORMATION: Primer sequence

<400> SEQUENCE: 240
gcagaagcta tgaagtaata tgggctgaat aca 33

<210> SEQ ID NO 241
<211> LENGTH: 33
<212> TYPE: DNA
<213> ORGANISM: Artificial Sequence
<220> FEATURE:
<223> OTHER INFORMATION: Primer sequence

<400> SEQUENCE: 241
ggtgccctgt tcatctaagt ggctgtggcc cca 33

<210> SEQ ID NO 242
<211> LENGTH: 33
<212> TYPE: DNA
<213> ORGANISM: Artificial Sequence
<220> FEATURE:
<223> OTHER INFORMATION: Primer sequence

<400> SEQUENCE: 242
gcacgagatc taaagcagcg gggcgccgct cag 33

<210> SEQ ID NO 243
<211> LENGTH: 33
<212> TYPE: DNA
<213> ORGANISM: Artificial Sequence
<220> FEATURE:
<223> OTHER INFORMATION: Primer sequence

<400> SEQUENCE: 243
gcacgagatc taaagctgcg gggcgccgct cag 33

<210> SEQ ID NO 244
<211> LENGTH: 33
<212> TYPE: DNA
<213> ORGANISM: Artificial Sequence
<220> FEATURE:
<223> OTHER INFORMATION: Primer sequence

<400> SEQUENCE: 244
gcacgagatc taaagccgcg gggcgccgct cag 33

<210> SEQ ID NO 245
<211> LENGTH: 33
<212> TYPE: DNA
<213> ORGANISM: Artificial Sequence
<220> FEATURE:
<223> OTHER INFORMATION: Primer sequence

<400> SEQUENCE: 245
gcacgagatc taaagcgacg gggcgccgct cag 33

<210> SEQ ID NO 246
<211> LENGTH: 33
<212> TYPE: DNA
<213> ORGANISM: Artificial Sequence
<220> FEATURE:
<223> OTHER INFORMATION: Primer sequence

<400> SEQUENCE: 246
gcacgagatc taaagcgtcg gggcgccgct cag 33

<210> SEQ ID NO 247

<211> LENGTH: 33
<212> TYPE: DNA
<213> ORGANISM: Artificial Sequence
<220> FEATURE:
<223> OTHER INFORMATION: Primer sequence

<400> SEQUENCE: 247
gcacgagatc taaagcgccg gggcgccgct cag                             33

<210> SEQ ID NO 248
<211> LENGTH: 33
<212> TYPE: DNA
<213> ORGANISM: Artificial Sequence
<220> FEATURE:
<223> OTHER INFORMATION: Primer sequence

<400> SEQUENCE: 248
agctatgaag taatataggc tgaatacaaa cca                             33

<210> SEQ ID NO 249
<211> LENGTH: 33
<212> TYPE: DNA
<213> ORGANISM: Artificial Sequence
<220> FEATURE:
<223> OTHER INFORMATION: Primer sequence

<400> SEQUENCE: 249
agctatgaag taatatcggc tgaatacaaa cca                             33

<210> SEQ ID NO 250
<211> LENGTH: 33
<212> TYPE: DNA
<213> ORGANISM: Artificial Sequence
<220> FEATURE:
<223> OTHER INFORMATION: Primer sequence

<400> SEQUENCE: 250
agctatgaag taatattggc tgaatacaaa cca                             33

<210> SEQ ID NO 251
<211> LENGTH: 33
<212> TYPE: DNA
<213> ORGANISM: Artificial Sequence
<220> FEATURE:
<223> OTHER INFORMATION: Primer sequence

<400> SEQUENCE: 251
agctatgaag taatatgagc tgaatacaaa cca                             33

<210> SEQ ID NO 252
<211> LENGTH: 33
<212> TYPE: DNA
<213> ORGANISM: Artificial Sequence
<220> FEATURE:
<223> OTHER INFORMATION: Primer sequence

<400> SEQUENCE: 252
agctatgaag taatatgcgc tgaatacaaa cca                             33

<210> SEQ ID NO 253
<211> LENGTH: 33
<212> TYPE: DNA
<213> ORGANISM: Artificial Sequence
<220> FEATURE:
<223> OTHER INFORMATION: Primer sequence

<400> SEQUENCE: 253
agctatgaag taatatgtgc tgaatacaaa cca                     33

<210> SEQ ID NO 254
<211> LENGTH: 20
<212> TYPE: DNA
<213> ORGANISM: Artificial Sequence
<220> FEATURE:
<223> OTHER INFORMATION: Primer sequence

<400> SEQUENCE: 254
ctccatggtg ctatagagca                                    20

<210> SEQ ID NO 255
<211> LENGTH: 21
<212> TYPE: DNA
<213> ORGANISM: Artificial Sequence
<220> FEATURE:
<223> OTHER INFORMATION: Primer sequence

<400> SEQUENCE: 255
gagccaagct ctccatctag t                                  21

<210> SEQ ID NO 256
<211> LENGTH: 20
<212> TYPE: DNA
<213> ORGANISM: Artificial Sequence
<220> FEATURE:
<223> OTHER INFORMATION: Primer sequence

<400> SEQUENCE: 256
gccctgtcaa gagttgacac                                    20

<210> SEQ ID NO 257
<211> LENGTH: 20
<212> TYPE: DNA
<213> ORGANISM: Artificial Sequence
<220> FEATURE:
<223> OTHER INFORMATION: Primer sequence

<400> SEQUENCE: 257
ggagttttcc acacggacac                                    20

<210> SEQ ID NO 258
<211> LENGTH: 20
<212> TYPE: DNA
<213> ORGANISM: Artificial Sequence
<220> FEATURE:
<223> OTHER INFORMATION: Primer sequence

<400> SEQUENCE: 258
tgcttctcct cttgggaagt                                    20

<210> SEQ ID NO 259
<211> LENGTH: 20
<212> TYPE: DNA
<213> ORGANISM: Artificial Sequence
<220> FEATURE:
<223> OTHER INFORMATION: Primer sequence

<400> SEQUENCE: 259
cccctatgtc cacttcagga                                    20

<210> SEQ ID NO 260
<211> LENGTH: 20
<212> TYPE: DNA

```
<213> ORGANISM: Artificial Sequence
<220> FEATURE:
<223> OTHER INFORMATION: Primer sequence

<400> SEQUENCE: 260
cggttaatgt ggctctggtt                                               20

<210> SEQ ID NO 261
<211> LENGTH: 20
<212> TYPE: DNA
<213> ORGANISM: Artificial Sequence
<220> FEATURE:
<223> OTHER INFORMATION: Primer sequence

<400> SEQUENCE: 261
ggagcagctg gtcagagggg                                               20

<210> SEQ ID NO 262
<211> LENGTH: 20
<212> TYPE: DNA
<213> ORGANISM: Artificial Sequence
<220> FEATURE:
<223> OTHER INFORMATION: Primer sequence

<400> SEQUENCE: 262
gggaaggggg acactgggga                                               20

<210> SEQ ID NO 263
<211> LENGTH: 20
<212> TYPE: DNA
<213> ORGANISM: Artificial Sequence
<220> FEATURE:
<223> OTHER INFORMATION: Primer sequence

<400> SEQUENCE: 263
tccagatggc acattgtcag                                               20

<210> SEQ ID NO 264
<211> LENGTH: 20
<212> TYPE: DNA
<213> ORGANISM: Artificial Sequence
<220> FEATURE:
<223> OTHER INFORMATION: Primer sequence

<400> SEQUENCE: 264
agggagcagg aaagtgaggt                                               20

<210> SEQ ID NO 265
<211> LENGTH: 48
<212> TYPE: DNA
<213> ORGANISM: Artificial Sequence
<220> FEATURE:
<223> OTHER INFORMATION: EMX1

<400> SEQUENCE: 265
aaacggcaga agctggagga ggaagggcct gagtccgagc agaagaag                48

<210> SEQ ID NO 266
<211> LENGTH: 48
<212> TYPE: DNA
<213> ORGANISM: Artificial Sequence
<220> FEATURE:
<223> OTHER INFORMATION: ssODN

<400> SEQUENCE: 266
cttaagggct cccatcacat caaccggtgg cgcattgcca cgaagcag                48
```

```
<210> SEQ ID NO 267
<211> LENGTH: 20
<212> TYPE: DNA
<213> ORGANISM: Artificial Sequence
<220> FEATURE:
<223> OTHER INFORMATION: ASCL1

<400> SEQUENCE: 267
gcagccgctc gctgcagcag                                               20

<210> SEQ ID NO 268
<211> LENGTH: 20
<212> TYPE: DNA
<213> ORGANISM: Artificial Sequence
<220> FEATURE:
<223> OTHER INFORMATION: IL1R2

<400> SEQUENCE: 268
gacccagcac tgcagcctgg                                               20

<210> SEQ ID NO 269
<211> LENGTH: 20
<212> TYPE: DNA
<213> ORGANISM: Artificial Sequence
<220> FEATURE:
<223> OTHER INFORMATION: NEUROD1

<400> SEQUENCE: 269
ggggagcggt tgtcggagga                                               20
```

SET OF POLYPEPTIDES EXHIBITING NUCLEASE ACTIVITY OR NICKASE ACTIVITY WITH DEPENDENCE ON LIGHT OR IN PRESENCE OF DRUG OR SUPPRESSING OR ACTIVATING EXPRESSION OF TARGET GENE

REFERENCE TO A SEQUENCE LISTING SUBMITTED VIA EFS-WEB

The content of the ASCII text file of the sequence listing named "20190327_034574_012US1_subseqST25" which is 116,023 bytes in size was created on Mar. 27, 2019 and electronically submitted via EFS-Web on Apr. 21, 2019 is incorporated herein by reference in its entirety.

TECHNICAL FIELD

The present invention relates to a set of polypeptides exhibiting the nuclease activity or the nickase activity, or suppressing or activating expression of a target gene with dependence on light or in the presence of a drug.

BACKGROUND ART

In recent years, as a genome editing tool which can cut a desired target DNA sequence in a genome, the CRISPR (clustered regularly interspaced palindromic repeats)-Cas9 system has been developed (Non-Patent Documents 1-3). In this system, a guide RNA which guides *Streptococcus pyogenes*-derived Cas9 nuclease (hereinafter, referred to as "Cas9" or "Cas9 protein") and Cas9 to a target DNA sequence is used. A PAM (protospacer-adjacent motif) region which is complementary to first 20 bases of the guide RNA, and a C-terminal side thereof is represented by NGG (N represents any base of A, T, C and G) becomes a target DNA sequence, and is cut with Cas9.

The CRISPR-Cas9 system is a powerful tool which can simply and precisely cut an arbitrary sequence by designing an appropriate guide RNA, and can perform genome editing by introducing an arbitrary indel mutation (insertion/deletion mutation) into a cutting site when non-homologous end-joining (NHEJ) and homology-directed repair (HDR) are combined. However, a versatile method of controlling the activity of Cas9 spatially, temporally and reversibly has not been completed yet.

Meanwhile, in recent years, a molecule controlling approach utilizing photoactivation of a protein has appeared, and is called optogenetics (Non-Patent Documents 4, 5).

The present inventors altered the *Neurospora Crassa*-derived Vivid protein which forms a homodimer with dependence on light, and developed a pair of proteins "Magnet", which can precisely control formation and dissociation of a dimer by irradiation of light (Non-Patent Document 6).

CITATION LIST

Non-Patent Document

Non-Patent Document 1: Cong, L. et al. Science 339, 819-823 (2013)
Non-Patent Document 2: Mali, P. et al. Science 339, 823-826 (2013)
Non-Patent Document 3: Jinek, M. et al. Elife 2, e00471 (2013)
Non-Patent Document 4: Toettcher, J. E. et al., Nat. Methods 8, 35-38 (2011)
Non-Patent Document 5: Mueller, K. et al., Mol. BioSyst. 9, 596-608 (2013)
Non-Patent Document 6: Kawano, F. et al., Nat. Commun. 6, 6256 (2015)

SUMMARY

Technical Problem

A technical problem of the present invention is to provide a method of controlling the activity of Cas9 or a mutant thereof spatially, temporally and reversibly.

Solution to Problem

In order to solve the problem, the present inventors made fragments obtained by dividing Cas9 into two at a variety of positions, and fused each fragment to each of two polypeptides which form a dimer with dependence on light, and found out that when irradiated with light, as two polypeptides form a dimer, Cas9 is rearranged to recover the activity, and when irradiation with light is stopped, as a dimer is dissociated, Cas9 loses the activity. Then, we found out that when this photoactivatable Cas9 (hereinafter, referred to as "paCas9") is used, a desired target sequence can be precisely cut by using a guide RNA which is complementary to a target sequence.

Additionally, we found out that a target double-stranded nucleic acid can also be precisely cut by using a paCas9 nickase in which mutation has been introduced into an N-terminal side fragment of paCas9, and a pair of guide RNAs complementary to each of a target double-stranded nucleic acid, and at the same time, found out that when paCas9 or a paCas9 nickase and NHEJ or HDR are combined, desired indel mutation can be introduced into a target sequence.

Furthermore, we found out that expression of a target gene can be suppressed or activated, by introducing mutation into each of an N-terminal side fragment and a C-terminal side fragment of paCas9 to cause the loss of the nuclease/nickase activity, and using, for example, a guide RNA having a sequence complementary to a target gene.

In addition, we found out that, by using two polypeptides which form a dimer in the presence of a drug, in place of two polypeptides which form a dimer with dependence on light, the activity of Cas9 or a mutant thereof can be controlled spatially, temporally and reversibly.

Based on these findings, we completed the present invention.

That is, the present invention is as follows:

[1]

A set of two polypeptides exhibiting the nuclease activity with dependence on light or in the presence of a drug, in which an N-terminal side fragment and a C-terminal side fragment of a Cas9 protein are bound to each of two polypeptides which form a dimer with dependence on light or in the presence of a drug.

[2]

The set of polypeptides according to [1], wherein the N-terminal side fragment of a Cas9 protein includes a region of position 1 to position 60 of an amino acid sequence of SEQ ID No.: 2, and the C-terminal side fragment of a Cas9 protein includes a region of position 718 to position 1099 of an amino acid sequence of SEQ ID No.: 2.

[3]
The set of polypeptides according to [1],
wherein the N-terminal side fragment and the C-terminal side fragment of a Cas9 protein are such that:
(i) a region in which the N-terminal side fragment or the C-terminal side fragment, and an amino acid sequence of SEQ ID No.: 2 are overlapped is 70% or more of an amino acid sequence of SEQ ID No.: 2, and
(ii) the N-terminal side fragment or the C-terminal side fragment is a fragment comprising 100 or more amino acids of an amino acid sequence of SEQ ID No.: 2.

[4]
The set of polypeptides according to [1],
wherein the N-terminal side fragment and the C-terminal side fragment of a Cas9 protein are:
(1) a fragment comprising a sequence of 100 to 1300 amino acids including an N-terminus in an amino acid sequence of SEQ ID No.: 2, (2) a fragment comprising an amino acid sequence including addition, substitution, or deletion of one to several amino acids, in a sequence of 100 to 1300 amino acids including an N-terminus in an amino acid sequence of SEQ ID No.: 2, or (3) a fragment comprising an amino acid sequence having 80% or more sequence identity with a sequence of 100 to 1300 amino acids including an N-terminus in an amino acid sequence of SEQ ID No.: 2; and
(4) a fragment comprising a sequence of 100 to 1300 amino acids including a C-terminus in an amino acid sequence of SEQ ID No.: 2, (5) a fragment comprising an amino acid sequence including addition, substitution, or deletion of one to several amino acids, in a sequence of 100 to 1300 amino acids including a C-terminus in an amino acid sequence of SEQ ID No.: 2, or (6) a fragment comprising an amino acid sequence having 80% or more sequence identity with a sequence of 100 to 1300 amino acids including a C-terminus in an amino acid sequence of SEQ ID No.: 2.

[5]
The set of polypeptides according to [1], wherein the N-terminal side fragment and the C-terminal side fragment of a Cas9 protein are any of the following combinations:
a combination of an N-terminal fragment comprising amino acids at position 1 to position 189 in an amino acid sequence of SEQ ID No.: 2, and a C-terminal fragment comprising amino acids at position 190 to position 1368;
a combination of an N-terminal fragment comprising amino acids at position 1 to position 230 in an amino acid sequence of SEQ ID No.: 2, and a C-terminal fragment comprising amino acids at position 231 to position 1368;
a combination of an N-terminal fragment comprising amino acids at position 1 to position 257 in an amino acid sequence of SEQ ID No.: 2, and a C-terminal fragment comprising amino acids at position 258 to position 1368;
a combination of an N-terminal fragment comprising amino acids at position 1 to position 384 in an amino acid sequence of SEQ ID No.: 2, and a C-terminal fragment comprising amino acids at position 385 to position 1368;
a combination of an N-terminal fragment comprising amino acids at position 1 to position 532 in an amino acid sequence of SEQ ID No.: 2, and a C-terminal fragment comprising amino acids at position 533 to position 1368;
a combination of an N-terminal fragment comprising amino acids at position 1 to position 556 in an amino acid sequence of SEQ ID No.: 2, and a C-terminal fragment comprising amino acids at position 557 to position 1368;
a combination of an N-terminal fragment comprising amino acids at position 1 to position 574 in an amino acid sequence of SEQ ID No.: 2, and a C-terminal fragment comprising amino acids at position 575 to position 1368;
a combination of an N-terminal fragment comprising amino acids at position 1 to position 611 in an amino acid sequence of SEQ ID No.: 2, and a C-terminal fragment comprising amino acids at position 612 to position 1368;
a combination of an N-terminal fragment comprising amino acids at position 1 to position 640 in an amino acid sequence of SEQ ID No.: 2, and a C-terminal fragment comprising amino acids at position 641 to position 1368;
a combination of an N-terminal fragment comprising amino acids at position 1 to position 672 in an amino acid sequence of SEQ ID No.: 2, and a C-terminal fragment comprising amino acids at position 673 to position 1368;
a combination of an N-terminal fragment comprising amino acids at position 1 to position 687 in an amino acid sequence of SEQ ID No.: 2, and a C-terminal fragment comprising amino acids at position 688 to position 1368;
a combination of an N-terminal fragment comprising amino acids at position 1 to position 713 in an amino acid sequence of SEQ ID No.: 2, and a C-terminal fragment comprising amino acids at position 714 to position 1368;
a combination of an N-terminal fragment comprising amino acids at position 1 to position 754 in an amino acid sequence of SEQ ID No.: 2, and a C-terminal fragment comprising amino acids at position 755 to position 1368;
a combination of an N-terminal fragment comprising amino acids at position 1 to position 834 in an amino acid sequence of SEQ ID No.: 2, and a C-terminal fragment comprising amino acids at position 835 to position 1368;
a combination of an N-terminal fragment comprising amino acids at position 1 to position 867 in an amino acid sequence of SEQ ID No.: 2, and a C-terminal fragment comprising amino acids at position 868 to position 1368;
a combination of an N-terminal fragment comprising amino acids at position 1 to position 908 in an amino acid sequence of SEQ ID No.: 2, and a C-terminal fragment comprising amino acids at position 909 to position 1368;
a combination of an N-terminal fragment comprising amino acids at position 1 to position 940 in an amino acid sequence of SEQ ID No.: 2, and a C-terminal fragment comprising amino acids at position 941 to position 1368;
a combination of an N-terminal fragment comprising amino acids at position 1 to position 1048 in an amino acid sequence of SEQ ID No.: 2, and a C-terminal fragment comprising amino acids at position 1049 to position 1368; and a combination including addition, substitution, or deletion of one to several amino acids in a sequence of at least one fragment, in any of the above combinations; as well as a combination in which a sequence of at least one fragment is a fragment having 80% or more sequence identity with the above sequence, in any of the above combinations.

[6]
The set of two polypeptides according to any one of [1] to [5], wherein the set has mutation of D10A in the N-terminal side fragment of a Cas9 protein, and exhibits the nickase activity with dependence on light or in the presence of a drug.

[7]
The set of two polypeptides according to any one of [1] to [5], wherein the set has mutation of D10A in the N-terminal side fragment of a Cas9 protein, has mutation of H840A in the C-terminal side fragment, and suppresses expression of a target gene with dependence on light or in the presence of a drug.

[8]
The set of two polypeptides according to any one of [1] to [5], wherein the set has mutation of D10A in the N-terminal side fragment of a Cas9 protein, and has mutation of H840A in the C-terminal side fragment, a transcription activation domain binds to the C-terminal side fragment of a Cas9 protein through a linker or without through a linker, and the set activates expression of a target gene with dependence on light or in the presence of a drug.

[9] The set of polypeptides according to any one of [1] to [8], wherein the two polypeptides which form a dimer with dependence on light, each, are a polypeptide comprising an amino acid sequence of SEQ ID No.: 1 or a sequence having 80% or more sequence identity with this, or a mutant thereof.

[10]
The set of polypeptides according to [9], wherein one of the two polypeptides which form a dimer with dependence on light has a sequence in which Ile at a position 52 and Met at a position 55 are substituted with an amino acid having a positive charge on a side chain, in an amino acid sequence of SEQ ID No.: 1 or a sequence having 80% or more sequence identity with this, and the other of the two polypeptides which form a dimer with dependence on light has a sequence in which Ile at a position 52 and Met at a position 55 are substituted with an amino acid having a negative charge on a side chain, in an amino acid sequence of SEQ ID No.: 1 or a sequence having 80% or more sequence identity with this.

[11]
The set of polypeptides according to [10], wherein the two polypeptides which form a dimer with dependence on light are a polypeptide having mutations of I52R and M55R in an amino acid sequence of SEQ ID No.: 1 or a sequence having 80% or more sequence identity with this, and a polypeptide having mutations of I52D and M55G in an amino acid sequence of SEQ ID No.: 1 or a sequence having 80% or more sequence identity with this.

[12]
The set of polypeptides according to [11], wherein the polypeptide having mutations of I52R and M55R in an amino acid sequence of SEQ ID No.: 1 or a sequence having 80% or more sequence identity with this, and/or the polypeptide having mutations of I52D and M55G in an amino acid sequence of SEQ ID No.: 1 or a sequence having 80% or more sequence identity with this further have mutations of M135I and M165I.

[13]
The set of polypeptides according to any one of [1] to [8], wherein the two polypeptides which form a dimer in the presence of a drug are FKBP and FRB which form a dimer in the present of rapamycin.

[14]
A nucleic acid encoding the set of polypeptides according to any one of [1] to [13].

[15]
An expression vector including the nucleic acid according to [14].

[16]
A method of cutting a target double-stranded nucleic acid, the method including:
a step of incubating the target double-stranded nucleic acid, the set of polypeptides according to any one of [1] to [5], and a guide RNA including a sequence complementary to one sequence of the target double-stranded nucleic acid, by irradiating light, or in the presence of a drug.

[17]
A method of cutting a target double-stranded nucleic acid, the method including:
a step of incubating the target double-stranded nucleic acid, a set of polypeptides according to [6], and a pair of guide RNAs including a sequence complementary to each sequence of the target double-stranded nucleic acid, by irradiating light, or in the presence of a drug.

[18]
A method of suppressing expression of a target gene, the method including:
a step of incubating a target gene, the set of polypeptides according to [7], and a guide RNA including a sequence complementary to a partial sequence of the target gene, by irradiating light, or in the presence of a drug.

[19]
A method of activating expression of the gene, the method including:
a step of incubating a target gene, a set of polypeptides according to [8], a guide RNA including a sequence complementary to a partial sequence of the target gene, in which an aptamer is introduced therein, and an aptamer-binding protein ligated with a transcription activation domain, by irradiating light, or in the presence of a drug.

[20]
A kit for cutting a target double-stranded nucleic acid, including:
the set of polypeptides according to any one of [1] to [5], a nucleic acid encoding the set of polypeptides, or an expression vector including the nucleic acid, and
a guide RNA including a sequence complementary to one sequence of the target double-stranded nucleic acid or a nucleic acid encoding the same.

[21]
A kit for cutting a target double-stranded nucleic acid, including:
the set of polypeptides according to [6], a nucleic acid encoding the set of polypeptides, or an expression vector including the nucleic acid, and
a pair of guide RNAs including a sequence complementary to each sequence of the target double-stranded nucleic acid or nucleic acids encoding the same.

[22]
A kit for suppressing expression of a target gene, including:
the set of polypeptides according to [7], a nucleic acid encoding the set of polypeptides, or an expression vector including the nucleic acid, and a guide RNA including a sequence complementary to a partial sequence of the target gene, or a nucleic acid encoding the same.

[23]
A kit for activating expression of a target gene, including:
the set of polypeptides according to [8], a nucleic acid encoding the set of polypeptides, or an expression vector including the nucleic acid,
a guide RNA including a sequence complementary to a partial sequence of the target gene, in which an aptamer is introduced therein, or a nucleic acid encoding the same, and
an aptamer-binding protein ligated with a transcription activation domain, or a nucleic acid encoding the same.

Advantageous Effects of Invention

According to the present invention, the activity of Cas9 or a mutant thereof can be precisely controlled, by turning on/off light irradiation or the presence of a drug. Accordingly, since Cas9 or a mutant thereof which can be controlled spatially, temporally and reversibly can generate loss or alteration of the function of a variety of genes in in vivo, ex vivo gene therapy or the like, it is also suitable for application to medical care.

Inter alia, by applying Cas9 or a mutant thereof which can turn on/off light irradiation or the presence of a drug of the present invention, to the CRISPR-Cas9 system combined with a guide RNA, a target sequence can be precisely cut, and by using NHEJ or HDR concurrently, indel mutation can be precisely introduced into a target sequence.

BRIEF DESCRIPTION OF DRAWINGS

FIG. 1 exhibits design of photoactivatable Cas9 and property assessment: FIG. 1(a) exhibits an outline of photoactivatable Cas9 (paCas9): Cas9 was divided into two fragments having no nuclease activity, and the two fragments were fused with a positive Magnet (pMag) and a negative Magnet (nMag) which are dimerized with dependence on light, respectively: As pMag and nMag form a heterodimer by blue light irradiation, the divided Cas9 fragments were rearranged, and exhibited the guide RNA-dependent nuclease activity: FIG. 1(b) exhibits an outline of the luciferase reporter plasmid HDR assay: When Cas9 cuts the CMV-driving luciferase reporter (StopFluc-1) having an in-frame stop codon, the luciferase reporter was repaired by homologous recombination with a luciferase donor vector without a promoter, and the bioluminescence activity was recovered: FIG. 1(c) exhibits the light-dependent reporter activity in HEK293T cells, with N713 and C714 fragments of Cas9 fused with a depicted light-dependent dimerized domain: FIGS. 1(d) and 1(e) exhibits the result of investigation of the activities of paCas9-1 and full length Cas9 targeting StopFluc-1 and StopFluc-2 having mutation depicted in a PAM region, respectively: Numerical values were normalized using, as a positive control, a luciferase reporter having standard PAM (NGG): FIGS. 1(f) to 1(h) are the result of investigation of the activities Cas9 and paCas9 using Cas9 and paCas9, and a sgRNA having Watson-Crick transversion mutation of one base, targeting StopFluc-1, StopFluc-2, and StopFluc-3, respectively: Since G at a 5'-terminus of a sgRNA is necessary for expression from a U6 promoter, an experiment of mutating G at a 5'-terminus into C was not performed: A position of point mutation of each sgRNA is exhibited below each panel: Numerical values were normalized using completely matched sgRNAs as a positive control: and in FIGS. 1(c) to 1(h), data are exhibited as average ±s.e.m (n=6. Two independent experiments with biological triplicate). The sequence identifiers for the sequences are as follows: FIG. 1(d)=SEQ ID NO: 12, FIG. 1(e)=SEQ ID NO: 13, FIG. 1(f)=SEQ ID NO: 14, FIG. 1(g)=SEQ ID NO: 15, and FIG. 1(h)=SEQ ID NO: 16.

FIG. 2 exhibits optogenetic genome editing of an endogenous gene of a mammal with paCas9: FIG. 2(a) exhibits introduction of light-mediated indel mutation of a human CCR5 locus with paCas9: The frequency of indel mutation was assessed by the missmatch-sensitive T7E1 assay (T7E1 assay): FIG. 2(b) is an example of a sequence of a human CCR5 locus targeted by paCas9: The sequence identifiers from top to bottom are: SEQ ID NO: 17, SEQ ID NO: 18, SEQ ID NO: 19, SEQ ID NO: 20, SEQ ID NO: 21, SEQ ID NO: 22, and SEQ ID NO: 23: FIG. 2(c) exhibits that paCas9 can target a variety of endogenous genes: Cells were transfected with paCas9-1, and sgRNAs targeting an EMX1 site, a VEGFA site, and two sites of AAVS1: FIG. 2(d) exhibits light-dependent multiple genome editing with paCas9: HEK293T cells were transfected with paCas9-1 and a depicted sgRNA: FIG. 2(e) exhibits an outline of precise genome editing with paCas9: An arrow exhibits a supposed cutting site with paCas9: A 96-mer single-stranded oligonucleotide (ssODN) donor template was designed so as to be inserted into a HindIII site of an EMX1 locus: A target sequence is exhibited with a bold small letter, and an insertion sequence of 3 bases pairs is exhibited with a capital letter: The sequence identifiers from top to bottom are: SEQ ID NO: 24, SEQ ID NO: 25, and SEQ ID NO: 26: FIG. 2(f) exhibits precise genome editing using a single-stranded oligonucleotide template in which paCas9 and HDR are combined: The success frequency of HDR was measured by restriction enzyme fragment length polymorphism (RFLP), and calculated as the ratio of the HindIII digestion product to a substrate: The ratios of NHEJ and HDR are exhibited as an average (FIG. 2(a) is an average in n=3 independent experiments, FIGS. 2(c), 2(d) and 2(f) are an average in n=2 independent experiments): and in FIGS. 2(a), 2(c), 2(d) and 2(f), 20 hours after transfection, a sample was irradiated with 1.2 W/m$^2$ blue light, or placed in a dark place for 24 hours (FIG. 2(a), 2(c), and 2(d)) or 48 hours (FIG. 2(f)) until genome extraction.

FIG. 3 exhibits spatial and temporal control of the optimized Cas9 nuclease activity of paCas9-2: FIG. 3(a); in paCas9-2, the background of indel mutation of a human VEGFA locus was remarkably reduced while maintaining the light depending ability: FIG. 3(b) is the result of quantitation of the result of FIG. 3(a): Data are exhibits as average ±s.d. (n=3 of independent experiments): FIG. 3(c) exhibits spatial activation of paCas9: HEK293T cells were transfected with paCas9-2, a NHEJ-dependent EGFP-expressing surrogate reporter, and a sgRNA targeting a surrogate reporter: Twenty hours after transfection, a sample was irradiated with blue light of a slit pattern for 24 hours using a photomask: The width of the slit was 2 mm: A scale bar indicates 3 mm: A lower row is an image obtained by enlarging a part surrounded with a white frame at an upper row: FIG. 3(d) exhibits the result of line scanning of an intensity profile of EGFP and mCherry in FIG. 3(c): FIG. 3(e) exhibits an outline of an experiment for examining whether activation of paCas9 is reversible or not: First, HEK293T cells were transfected with paCas9-2 and a sgRNA targeting VEGFA: After twenty hours, the cells were irradiated with blue light for 6 hours, subsequently, the cells were divided into two groups, and each group was incubated in a bright place or a dark place: After 6 hours, the cells which were placed in a bright place and a dark place were transfected with only a sgRNA targeting EMX1, returned to a bright place and a dark place again and incubated: After 30 hours, a genomic DNA was extracted: If the paCas9 activity is reversible, in the cells which were transferred to a dark place before second transfection with a sgRNA targeting EMX1, indel mutation should have been generated in only a VEGFA locus: FIG. 3(f) exhibits a representative gel in the T7E1 assay of FIG. 3(e): and the frequency of indel mutation of EMX1 and VEGFA is exhibited below the gel (n=4. Two independent experiments with biological duplicate).

FIG. 4 exhibits optogenetic control of transcription interference with padCas9 using a guide RNA: FIG. 4(a) exhibits an outline of photoactivatable CRISPR interference using paCas9-2 having D10A and H840A mutations (padCas9): In a dark place, N713(D10A)-pMag and nMag-C714(H840A) did not exhibit the activity: When blue light was irradiated, pMag and nMag formed a heterodimer, subsequently, N713 (D10A) and C714 (H840A) were rearranged to become functional dCas9, and transcription interference guided with a sgRNA became possible: FIG. 4(b) exhibits that padCas9 can suppress gene expression with dependence on light:

HEK293T cells were transfected with N713 (D10A)-pMag and nMag-C714 (H840A), a luciferase reporter, and depicted sgRNAs targeting luciferase (sgFluc-1, -2, and -3): Twenty hours after transfection, the sample was irradiated with 1.2 W/m$^2$ blue light, or the sample was placed in a dark place, until 30 hours before measurement of bioluminescence of luciferase: In this experiment, a luciferase reporter having PEST and an mRNA-destabilization sequence was used: Data are exhibited as average±s.e.m (n=6. Two independent experiments with biological triplicate.): Student's two-sided t test was conducted: N.S. exhibits no significant difference: ***p<0.005 (for a dark place sample): FIG. 4(c) exhibits change with time of recovery of the luciferase activity after blue light irradiation: HEK293T cells were transfected with N713 (D10A)-pMag and nMag-C714 (H840A), a luciferase reporter, and a depicted sgRNA: A sample was irradiated with 1.2 W/m$^2$ blue light from immediately after transfection until 30 hours before bioluminescence measurement (time 0): After measurement at time 0, the sample was irradiated with 1.2 W/m$^2$ blue light (solid line), or the sample was placed in dark place (broken line), and bioluminescence was measured every 6 hours: and data are exhibited as average±s.e.m (n=6. Two independent experiments with biological triplicate.), and normalized with respect to negative control cells at time 0 (under continuous light irradiation).

FIG. 5 exhibits construction of a rapamycin-dependent Cas9 fragment: FIG. 5(a) exhibits divided site candidates of 18 places of the *Streptococcus pyogenes* Cas9 protein: FIG. 5(b) exhibits a construct of rapamycin-dependent Cas9: and an N-terminal side fragment or a C-terminal side fragment of Cas9 was fused with FRB and FKBP, respectively.

FIG. 6 exhibits screening of a Cas9 fragment: FIG. 6(a) exhibits the ligand-induced Cas9 activity which was measured by the luciferase reporter plasmid HDR assay: HEK293T cells were transfected with an N-terminal side fragment of Cas9 fused with FRB, a C-terminal side fragment of Cas9 fused with FKBP, a luciferase reporter with a stop codon inserted therein, and a luciferase donor vector without a promoter: and FIG. 6(b) exhibits screening of Cas9 which has been divided at a variety of sites in the vicinity of residues at a 713 position and a 714 position of Cas9.

FIG. 7 is a conceptual diagram of paCas9 which was made based on respective crystal structures of Cas9 (PDB ID: 4UN3), and the Vivid protein (PDB ID: 3RH8) in the light-irradiated state: and a position surrounded with a circle is a site at which each fragment of Cas9 and a Magnet are bound.

FIG. 8 exhibits analysis of change with time of indel mutation at an EMX1 locus with paCas9: HEK293T cells were transfected with paCas9-1 targeting EMX1, and incubated for 20 hours, thereafter, the cells were irradiated with 1.2 W/m$^2$ blue light, and a DNA was extracted at the depicted time: The frequency of indel mutation was assessed by the mismatch-sensitive T7E1 assay: Data are exhibited as average±s.e.m. (n=4. Two independent experiments with biological duplicate.): and the indel frequencies at 0, 1, 3, and 6 hours were less than a detection limit (1%).

FIG. 9 exhibits introduction of indel mutation with paCas9 into a human EMX1 locus in HeLa cells: and the frequency of indel mutation was assessed by the mismatch-sensitive T7E1 assay.

FIG. 10 exhibits that a paCas9 nickase can be effectively genome-edited using a pair of sgRNAs: FIG. 10(a) exhibits appearance that a double-stranded DNA is cut with dependence on light using one pair of sgRNAs and a paCas9 D10A nickase: When D10A mutation is introduced into an N-terminal side fragment of Cas9, a paCas9 nuclease is converted into a paCas9 nickase: Using a pair of sgRNAs targeting each strand of a target gene, a paCas9 nickase cuts a DNA double strand of a target site with dependence on light: FIG. 10(b) exhibits a human EMX1 locus: A black underlined portion exhibits a target region of a pair of sgRNAs: A grey underlined portion exhibits a PAM region: An arrow exhibits a supposed cutting site: The sequence identifiers from top to bottom are: SEQ ID NO: 27 and SEQ ID NO: 28: and FIG. 10(c) exhibits the representative result of the T7E1 assay used for calculating the frequency of indel mutation which was induced by a paCas9 nickase (average. n=2 of independent experiments).

FIG. 11 exhibits activation of a spatial surrogate reporter with paCas9: FIG. 11(a) exhibits an outline of the surrogate EGFP reporter system: A surrogate reporter is composed of mCherry, a target sequence of paCas9 (herein, EMX1 target site), and EGFP: In a dark place, mCherry is structurally expressed by a CMV promoter, and since when there is no Cas9 activity, an EGFP gene becomes out of frame, EGFP fluorescence is not observed: When blue light is irradiated, paCas9 is activated, and a double strand at an EMX1 target site of a reporter is cut: By the NHEJ route, this cut site is repaired while generating frame shift mutation: By this frame shift mutation, an EGFP gene becomes in frame, and a mCherry-EGFP-fused polypeptide is expressed: FIG. 11(b) exhibits activation with a slit pattern of paCas9: HEK293T cells were transfected with paCas9-2, a surrogate EGFP reporter, and a sgRNA targeting a surrogate reporter: and twenty hours after transfection, the sample was placed in a dark place, the entirety was irradiated with blue light, or the sample was irradiated with blue light of a slit pattern using a photomask, and allowed to stand for 24 hours.

FIG. 12 exhibits an amino acid sequence of one example of a fused polypeptide of an N-terminal side fragment of Cas9 and pMag (N713-pMag) (SEQ ID NO: 3).

FIG. 13 exhibits an amino acid sequence of one example of a fused polypeptide of nMagHigh1 and a C-terminal side fragment of Cas9 (nMagHigh1-C714) (SEQ ID NO: 4).

FIG. 14 exhibits an amino acid sequence of one example of a fused polypeptide of nMag and a C-terminal side fragment of Cas9 (nMag-C714) (SEQ ID NO: 5).

FIG. 15 exhibits a DNA sequence of StopFluc-1 (SEQ ID NO: 6): A target sequence is exhibited with a bold letter, and a PAM sequence is exhibited with an underline: and TAA upstream by 5 to 3 bases of a PAM sequence is a stop codon.

FIG. 16 exhibits a DNA sequence of StopFluc-2 (SEQ ID NO: 7): A target sequence is exhibited with a bold letter, and a PAM sequence is exhibited with an underline: and TAA upstream by 5 to 3 bases of a PAM sequence is a stop codon.

FIG. 17 exhibits a DNA sequence of StopFluc-3 (SEQ ID NO: 8): A target sequence is exhibited with a bold letter, and a PAM sequence is exhibited with an underline: and TAA upstream by 4 to 2 bases of a PAM sequence is a stop codon.

FIG. 18 exhibits optogenic control of expression of an arbitrary genome gene using padCas9: nMag-CdCas9 and NdCas9-pMag, ligated with VP64 of a transcription activation domain, are dissociated in a dark place, but by irradiating light, they form a complex, and at the same time, an MS2-binding sequence is introduced, and this binds to a sgRNA designed so that a nucleotide sequence on a 5'-terminal side becomes complementary to a nucleotide sequence in the vicinity of a target gene, and MS2 of an aptamer-binding protein ligated with p65 and HSF1 of a transcription activation domain: Thereby, transcription active domains (VP64, p65, HSF1) accumulate in the vicinity of a target gene in a light irradiation-dependent manner, and transcription of a target gene is activated: and when light is shielded, since the complex is dissociated, transcription activation domains (VP64, p65, HSF1) disappear from the vicinity of a target gene, and transcription of a target gene is stopped.

FIG. 19 exhibits the result of that expression of a genome gene (FIG. 19(a) is ASCL1, FIG. 19(b) is IL1R2, FIG. 19(c) is NEUROD1) of HEK293T cells was activated with light using the technique of FIG. 18.

FIG. 20 exhibits the result of responsiveness of the case where an aptamer (PP7-binding sequence) is introduced into a 3'-terminus of a sgRNA (upper), and the case where an aptamer (PP7-binding sequence) is introduced into a stem loop of a sgRNA (lower).

FIG. 21 exhibits that, by activating expression of a genome gene (NEUROD1) of human iPS cells with light, the relevant cells can be differentiated into nerve cells (majenda): and FIG. 21(a) exhibits fluorescent images of five different visual fields in a dark place, FIG. 21(b) exhibits fluorescent images of five different visual fields under light irradiation, respectively.

FIG. 22 exhibits an amino acid sequence of one example of a fused polypeptide of an N-terminal side fragment of dCas9 and pMag (dN713-pMag) (SEQ ID NO: 9).

FIG. 23 exhibits an amino acid sequence of one example of a fused polypeptide of nMagHigh1, VP64 and a C-terminal side fragment of dCas9 (nMagHigh1-dC714-VP64) (SEQ ID NO: 10).

FIG. 24 exhibits an amino acid sequence of one example of a fused polypeptide of MS2, p65 and HSF1 (MS2-p65-HSF1) (SEQ ID NO: 11).

DESCRIPTION OF EMBODIMENTS

The present invention will be explained more specifically by Description of Embodiments, but the present invention is not limited to the following Description of Embodiments, and can be carried out by various modifications.

(Set of Polypeptides Exhibiting the Nuclease Activity)

A first aspect of a set of polypeptides of the present invention is a set of two polypeptides, in which an N-terminal side fragment and a C-terminal side fragment of a Cas9 protein are bound to each of two polypeptides which form a dimer with dependence on light or in the presence of a drug, and the set exhibits the nuclease activity with dependence on light or in the presence of a drug.

In the present specification, the nuclease activity means the activity of hydrolyzing and cutting a phosphodiester bond between bases of a double-stranded nucleic acid, which is the original function of Cas9.

In the present aspect, the "set of two polypeptides exhibiting the nuclease activity" has a configuration that an N-terminal side fragment and a C-terminal side fragment of a Cas9 protein are bound to each of two polypeptides which form a dimer with dependence on light or in the presence of a drug.

The N-terminal side fragment and the C-terminal side fragment of the Cas9 protein refers to a fragment comprising a partial sequence of the Cas9 protein or a sequence containing mutation in the partial sequence, respectively, and an N-terminal amino acid of the N-terminal side fragment is an amino acid which is more on a side of N-terminal than an N-terminal amino acid of the C-terminal side fragment, in a sequence of SEQ ID No.: 2. A C-terminal amino acid of the N-terminal side fragment may be an amino acid which is more N-terminal, or more C-terminal than an N-terminal amino acid of the C-terminal side fragment, in the sequence of SEQ ID No.: 2.

The N-terminal side fragment and the C-terminal side fragment may be designed so that they contain regions of position 1 to position 60 and position 718 to position 1099 of an amino acid sequence of SEQ ID No.: 2, respectively. These regions are RuvC and HNH regions which are a nuclease activity domain of the Cas9 protein, as exhibited in FIG. 5.

The N-terminal side fragment and the C-terminal side fragment may be designed that a region in which the N-terminal side fragment or the C-terminal side fragment and an amino acid sequence of SEQ ID No.: 2 are overlapped becomes 70% or more, 80% or more, 90% or more, 95% or more, 98% or more, 100%, or 100% or more of an amino acid sequence of SEQ ID No.: 2. Herein, the "region in which the N-terminal side fragment or the C-terminal side fragment and an amino acid sequence of SEQ ID No.: 2 are overlapped" means, for example, 990 amino acids of from a 11-positional amino acid to a 1000-positional amino acid, when the N-terminal side fragment is composed of from a 11-positional amino acid to a 400-positional amino acid of SEQ ID No.: 2, and the C-terminal side fragment is composed of from a 390-positional amino acid to a 1000-positional amino acid. Accordingly, the relevant region is about 72% of an amino acid sequence (1368 amino acids) of SEQ ID No.: 2. Additionally, for example, the "region in which the N-terminal side fragment or the C-terminal side fragment and an amino acid sequence of SEQ ID No.: 2 are overlapped" is composed of 1180 amino acids which is a total of 590 amino acids of from 11-positional to 600-positional amino acids, and 590 amino acids of from position 611 to position 1200, and is about 86% of an amino acid sequence of SEQ ID No.: 2, when the N-terminal side fragment is composed of from a 11-positional amino acid to a 600-positional amino acid of SEQ ID No.: 2, and the C-terminal side fragment is composed of from a 611-positional amino acid to a 1200-positional amino acid.

The N-terminal side fragment or the C-terminal side fragment obtained by designing so that a region, in which the N-terminal side fragment or the C-terminal side fragment of Cas9, and an amino acid sequence of SEQ ID No.: 2 are overlapped, becomes 70% or more, 80% or more, 90% or more, 95% or more, 98% or more, 100%, or 100% or more of an amino acid sequence of SEQ ID No.: 2 can become an N-terminal side fragment or a C-terminal side fragment in Cas9 or a Cas9 protein derived from other species other than derived from *Streptococcus pyogenes*. In the present specification, the same applies in the case of a fragment comprising an amino acid sequence containing addition, substitution or deletion of one to several amino acids, or a fragment comprising an amino acid sequence having 80% or more sequence identity with an amino acid sequence of a fragment.

In the present invention, in place of Cas9 derived from *Streptococcus pyogenes*, for example, Cas9 disclosed in Nature (2015) 520, 186-191 and BMC Genomics (2015) 16:863 as well as WO 2014/144288, among them, SaCas9 derived from *Staphylococcus aureus* may be used.

The N-terminal side fragment and the C-terminal side fragment may be designed as a fragment comprising 100 or more amino acids, 200 or more amino acids, 300 or more amino acids, 400 or more amino acids, 500 or more amino acids, 600 or more amino acids, or 700 or more amino acids of an amino acid sequence of SEQ ID No.: 2, respectively.

The N-terminal side fragment may contain a sequence of position 1 to position 200 of an amino acid sequence of SEQ ID No.: 2.

Additionally, it is preferable that the N-terminal side fragment and the C-terminal side fragment are cut at a domain other than nuclease domains (RuvC, HNH) involved in DNA cutting, in an amino acid sequence of SEQ ID No.: 2, and for example, may be a fragment obtained by cutting an amino acid sequence of SEQ ID No.: 2 at any position of position 180 to position 200, position 220 to position 240, position 247 to position 267, position 374 to position 394, position 522 to position 542, position 564 to position 584, position 630 to position 650, position 662 to position 682, position 677 to position 697, and position 693 to position 718. Alternatively, the N-terminal side fragment and the C-terminal fragment may be a fragment obtained by cutting an amino acid sequence of SEQ ID No.: 2 at any position of position 186 to position 193, position 227 to position 234, position 254 to position 261, position 381 to position 388, position 529 to position 536, position 553 to position 560, position 571 to position 578, position 608 to position 615, position 637 to position 644, position 669 to position 676, position 684 to position 691, and position 710 to position 717.

The N-terminal side fragment and the C-terminal fragment may be a fragment comprising an amino acid sequence containing addition, substitution, or deletion of one to several amino acids, in an amino acid sequence of the thus obtained fragment, or a fragment comprising an amino acid sequence having 80% or more sequence identity with an amino acid sequence of the thus obtained fragment.

The N-terminal side fragment and the C-terminal side fragment of the Cas9 protein may be a fragment comprising a sequence of 100 to 1300 amino acids containing an N-terminus in an amino acid sequence of SEQ ID No.: 2, and a fragment comprising a sequence of 100 to 1300 amino acids containing a C-terminus in an amino acid sequence of SEQ ID No.: 2, respectively.

The N-terminal side fragment and the C-terminal side fragment may be a fragment comprising an amino acid sequence containing addition, substitution, or deletion of one to several amino acids, in an amino acid sequence of such a fragment, or a fragment comprising an amino acid sequence having 80% or more sequence identity with an amino acid sequence of such a fragment.

The N-terminal side fragment and the C-terminal side fragment of the Cas9 protein may be any of the following combinations:

a combination of an N-terminal fragment comprising amino acids at position 1 to position 189 in an amino acid sequence of SEQ ID No.: 2, and a C-terminal fragment comprising amino acids at position 190 to position 1368;

a combination of an N-terminal fragment comprising amino acids at position 1 to position 230 in an amino acid sequence of SEQ ID No.: 2, and a C-terminal fragment comprising amino acids at position 231 to position 1368;

a combination of an N-terminal fragment comprising amino acids at position 1 to position 257 in an amino acid sequence of SEQ ID No.: 2, and a C-terminal fragment comprising amino acids at position 258 to position 1368;

a combination of an N-terminal fragment comprising amino acids at position 1 to position 384 in an amino acid sequence of SEQ ID No.: 2, and a C-terminal fragment comprising amino acids at position 385 to position 1368;

a combination of an N-terminal fragment comprising amino acids at position 1 to position 532 in an amino acid sequence of SEQ ID No.: 2, and a C-terminal fragment comprising amino acids at position 533 to position 1368;

a combination of an N-terminal fragment comprising amino acids at position 1 to position 556 in an amino acid sequence of SEQ ID No.: 2, and a C-terminal fragment comprising amino acids at position 557 to position 1368;

a combination of an N-terminal fragment comprising amino acids at position 1 to position 574 in an amino acid sequence of SEQ ID No.: 2, and a C-terminal fragment comprising amino acids at position 575 to position 1368;

a combination of an N-terminal fragment comprising amino acids at position 1 to position 611 in an amino acid sequence of SEQ ID No.: 2, and a C-terminal fragment comprising amino acids at position 612 to position 1368;

a combination of an N-terminal fragment comprising amino acids at position 1 to position 640 in an amino acid sequence of SEQ ID No.: 2, and a C-terminal fragment comprising amino acids at position 641 to position 1368;

a combination of an N-terminal fragment comprising amino acids at position 1 to position 672 in an amino acid sequence of SEQ ID No.: 2, and a C-terminal fragment comprising amino acids at position 673 to position 1368;

a combination of an N-terminal fragment comprising amino acids at position 1 to position 687 in an amino acid sequence of SEQ ID No.: 2, and a C-terminal fragment comprising amino acids at position 688 to position 1368;

a combination of an N-terminal fragment comprising amino acids at position 1 to position 713 in an amino acid sequence of SEQ ID No.: 2, and a C-terminal fragment comprising amino acids at position 714 to position 1368;

a combination of an N-terminal fragment comprising amino acids at position 1 to position 754 in an amino acid sequence of SEQ ID No.: 2, and a C-terminal fragment comprising amino acids at position 755 to position 1368;

a combination of an N-terminal fragment comprising amino acids at position 1 to position 834 in an amino acid sequence of SEQ ID No.: 2, and a C-terminal fragment comprising amino acids at position 835 to position 1368;

a combination of an N-terminal fragment comprising amino acids at position 1 to position 867 in an amino acid sequence of SEQ ID No.: 2, and a C-terminal fragment comprising amino acids at position 868 to position 1368;

a combination of an N-terminal fragment comprising amino acids at position 1 to position 908 in an amino acid sequence of SEQ ID No.: 2, and a C-terminal fragment comprising amino acids at position 909 to position 1368;

a combination of an N-terminal fragment comprising amino acids at position 1 to position 940 in an amino acid sequence of SEQ ID No.: 2, and a C-terminal fragment comprising amino acids at position 941 to position 1368;

a combination of an N-terminal fragment comprising amino acids at position 1 to position 1048 in an amino acid sequence of SEQ ID No.: 2, and a C-terminal fragment comprising amino acids at position 1049 to position 1368; and a combination containing addition, substitution, or deletion of one to several amino acids in a sequence of at least one fragment, in any of the aforementioned combinations; as well as a combination in which a sequence of at least one fragment is a fragment having 80% or more sequence identity with the above sequence, in any of the aforementioned combinations.

The N-terminal side fragment and the C-terminal side fragment of the Cas9 protein are not particularly limited, but may be, for example, a combination of an N-terminal fragment comprising amino acids at position 1 to position 713 in an amino acid sequence of SEQ ID No.: 2, and a C-terminal fragment comprising amino acids at position 714 to position 1368;

a combination containing addition, substitution, or deletion of one to several amino acids in a sequence of at least one fragment, in the relevant combination;

a combination containing addition, substitution, or deletion of one to several amino acids in each sequence of two fragments, in the relevant combination;

a combination in which a sequence of at least one fragment has 80% or more sequence identity with the above sequence, in the relevant combination; as well as a combination in which each sequence of two fragments has 80% or more sequence identity with the above sequence, in the relevant combination.

In the present specification, an amino acid, an "amino acid" is used in its broadest sense, and includes, in addition to a natural amino acid, a derivative thereof or an artificial amino acid. In the present specification, examples of an amino acid include a natural proteinaceous L-amino acid; a non-natural amino acid; a chemically synthesized compound having the properties known in the art, which are the characteristics of an amino acid. Examples of the non-natural amino acid are not limited to, but include an α,α-disubstituted amino acid (a-methylalanine etc.), an N-alkyl-α-amino acid, a D-amino acid, a β-amino acid, and a a-hydroxyacid, in which a structure of a main chain is different from a natural type, an amino acid in which a structure of a side chain is different from a natural type (norleucine, homohistidine etc.), an amino acid in which a side chain has extra methylene ("homo" amino acid, homophenylalanine, homohistidine etc.), and an amino acid in which a carboxylic acid functional group amino acid in a side chain is substituted with a sulfonic acid group (cysteic acid etc.).

In the present specification, an amino acid is represented by conventional one letter code or three letter code, in some cases. An amino acid represented by one letter code or three letter code includes a mutant and a derivative of each of them, in some cases.

In the present specification, when a certain amino acid sequence contains addition, substitution, or deletion of one to several amino acids, this means that 1, 2, 3, 4, 5, 6, 7, 8 or 9 amino acids are added (inserted), substituted, or deleted at a terminus or a non-terminus of the sequence. The number of amino acids to be added, substituted, or deleted is not particularly limited, as far as the resultant polypeptide exerts the effect in the present invention. Additionally, a site to be added, substituted, or deleted may be at one place or two or more places.

In the present specification, when sequence identity with a certain amino acid sequence is 80% or more, the sequence identity may be 85% or more, 90% or more, 95% or more, 98% or more, or 99% or more. The sequence identity can be obtained by a person skilled in the art according to the known method.

The "set of two polypeptides exhibiting the nuclease activity with dependence on light or in the presence of a drug" of the present invention can precisely cut a target double-stranded nucleic acid sequence with dependence on light or in the presence of a drug, by using by combining it with a guide RNA designed based on the target double-stranded nucleic acid sequence. Herein, the guide RNA is also called sgRNA or gRNA, and plays a role in inducing Cas9 to a target sequence. The guide RNA used in the present invention may be designed like a guide RNA used in the standard CRISPR-Cas9 system. For example, it can be designed so as to include a sequence complementary to about 20 bases upstream of the target sequence having "NGG" (N indicates any base of A, G, C and T) on a terminus. By preparing a plurality of guide RNAs, a plurality of target sequences can also be cut at the same time.

Such a method of cutting a double-stranded nucleic acid is also included in the present invention.

Furthermore, when the "set of two polypeptides exhibiting the nuclease activity with dependence on light or in the presence of a drug" of the present invention and NHEJ or HDR are combined, desired indel mutation can also be introduced into the target sequence. Multiple gene modification may be performed using a plurality of guide RNAs.

(Set of Polypeptides Exhibiting the Nickase Activity)

A second aspect of the set of polypeptides of the present invention is a set of two polypeptides, in which an N-terminal side fragment and a C-terminal side fragment of a Cas9 protein are bound to each of two polypeptides which form a dimer with dependence on light or in the presence of a drug, and the set exhibits the nickase activity with dependence on light or in the presence of a drug.

In the present specification, the nickase activity means the activity of forming a nick in a single strand among a double-stranded nucleic acid.

In the present aspect, the "set of two polypeptides exhibiting the nickase activity with dependence on light or in the presence of a drug" has a configuration that an N-terminal side fragment and a C-terminal side fragment of a Cas9 protein are bound to each of two polypeptides which form a dimer with dependence on light or in the presence of a drug, like the aforementioned set of two polypeptides exhibiting the nuclease activity, and the N-terminal side fragment contains mutation of D10A. Except for this mutation, the N-terminal side fragment and the C-terminal side fragment in the present aspect can be designed like the N-terminal side fragment and the C-terminal side fragment used in the set of two polypeptides exhibiting the nuclease activity.

In the present specification, when mutation is contained at a Y position of an amino acid sequence of SEQ ID No.: X, and addition or deletion is generated from a natural sequence in SEQ ID No.: X, which amino acid corresponds to a Y position can be determined by a person skilled in the art, subsequent to sequences before and after etc. Accordingly, in the case of D10A, an amino acid which is 10th when counted from an N-terminus is not necessarily substituted with A, and it is meant that an amino acid which corresponds to 10th D when counted from an N-terminus in a natural sequence is substituted with A.

The set of two polypeptides exhibiting the nickase activity can cut a target double-stranded nucleic acid, with dependence on light or in the presence of a drug, by combining it with a pair of guide RNAs targeting each strand of the target double-stranded nucleic acid. In this case, since the target double-stranded nucleic acid is cut at a region sandwiched by a pair of guide RNAs as exhibited in FIG. 9 described later, sequence specificity can be enhanced more than the case where a single guide RNA is used.

Each guide RNA can be designed like the polypeptide set exhibiting the nuclease activity. Alternatively, by preparing a plurality of pairs of guide RNAs, a plurality of target sequences can also be cut at the same time.

Such a method of cutting a double-stranded nucleic acid is also included in the present invention.

Additionally, when the "set of two polypeptides exhibiting the nickase activity" of the present invention is combined with NHEJ or HDR, desired indel mutation can also be introduced into the target sequence. Multiple gene modification may be performed using a plurality of guide RNAs.

(Set of Two Polypeptides Suppressing Expression of a Target Gene)

A third aspect of a set of polypeptides of the present invention is a set of two polypeptides, in which an N-terminal side fragment and a C-terminal side fragment of a Cas9 protein are bound to each of two polypeptides which form a dimer with dependence on light or in the presence of a drug, and the set suppresses expression of a target gene with dependence on light or in the presence of a drug.

In the present specification, "expression of a gene" is used as the concept including both of transcription by which an RNA is synthesized employing a DNA as a template, and translation by which a polypeptide is synthesized based on an RNA sequence.

In the present aspect, the "set of two polypeptides suppressing expression of a target gene" has a configuration that an N-terminal side fragment and a C-terminal side fragment of a Cas9 protein are bound to each of two polypeptides which form a dimer with dependence on light or in the presence of a drug, like the aforementioned set of two polypeptides exhibiting the nuclease activity, and the N-terminal fragment contains mutation of D10A, and the C-terminal side fragment contains mutation of H840A. The Cas9 protein with these mutations introduced therein (also called "dCas9") loses the nuclease activity and the nickase activity. Except for these mutations, the N-terminal side fragment and the C-terminal side fragment in the present aspect can be designed like the N-terminal side fragment and the C-terminal side fragment used in the set of two polypeptides exhibiting the nuclease activity.

The set of two polypeptides suppressing expression of a target gene can suppress expression of the target gene, with dependence on light or in the presence of a drug, by combining it with a guide RNA having a sequence complementary to a part of a sequence of the target gene. In this case, the guide RNA can have, for example, a sequence complementary to a part (e.g. about 20 nucleotides) of a promoter sequence or an exon sequence of a sense strand or an antisense strand of the target gene, thereby, initiation of transcription or elongation of a mRNA is inhibited.

Such a method of suppressing gene expression is also included in the present invention.

(Set of Two Polypeptides Activating Expression of a Target Gene)

A fourth aspect of a set of polypeptides of the present invention is a set of two polypeptides, in which an N-terminal side fragment and a C-terminal side fragment of a Cas9 protein are bound to each of two polypeptides which form a dimer with dependence on light or in the presence of a drug, and the set activates expression of a target gene with dependence on light or in the presence of a drug.

In the present aspect, the "set of two polypeptides activating expression of a target gene" has a configuration that an N-terminal side fragment and a C-terminal side fragment of a Cas9 protein are bound to each of two polypeptides which form a dimer with dependence on light or in the presence of a drug, like the aforementioned set of two polypeptides exhibiting the nuclease activity, and the N-terminal side fragment contains mutation of D10A, the C-terminal side fragment contains mutation of H840A, and a transcription activation domain is bound to the C-terminal side fragment of the Cas9 protein, preferably, to a C-terminal side of the C-terminal side fragment, through a linker or without through a linker. Except for these mutations, the N-terminal side fragment and the C-terminal side fragment in the present aspect can be designed like the N-terminal side fragment and the C-terminal side fragment used in the set of two polypeptides exhibiting the nuclease activity.

The transcription activation domain is a domain also called transactivation domain or transactivator, and is a transcription activation domain for a target gene. In the present invention, as the transcription activation domain, VP64 is suitably used.

The linker which is used when the transcription activation domain binds to the C-terminal side fragment of the Cas9 protein is not particularly limited, but a flexible linker comprising glycine and serine can be used.

The set of two polypeptides activating expression of a target gene can activate expression of the target gene, with dependence on light or in the presence of a drug, by combining it with a guide RNA having a sequence complementary to a part of a sequence of the target gene. In this case, the guide RNA can have a sequence complementary to a part (e.g. about 20 bases) of a promoter sequence or an exon sequence of a sense strand or an antisense strand of the target gene, thereby, initiation of transcription or elongation of a mRNA is activated.

Such a method of activating gene expression is also included in the present invention.

In the present invention, as the transcription activation domain, a set of two polypeptides activating gene expression of the target gene, containing a polypeptide in which VP64 is bound to the C-terminal side fragment of the Cas9 protein is preferable, and it is suitable that as an aptamer-binding protein, MS2 is used, and as the transcription activation domain binding to the aptamer-binding protein, p65 and HSF1 are used.

As a factor corresponding to VP64, MS2, p65 and HSF1, the known transcription activation domain and aptamer-binding protein can also be used, and for example, a transcription activation domain and an aptamer-binding protein such as those disclosed in Nature (2015) 517, 583-588 and nature protocols (2012) 7 (10), 1797-1807 can be used.

(Set of Two Polypeptides Forming a Dimer with Dependence on Light)

In the present specification, the "set of two polypeptides forming a dimer with dependence on light" (hereinafter, referred to as "light switch") refers to a pair of natural proteins forming a homodimer or a heterodimer by irradiation of light, or one obtained by artificially modifying this. Non-limiting examples of the light switch include the following:

[Pair Forming a Heterodimer]

PhyB and PIF (Levskaya, A., et al., Nature, 461, 997-1001 (2009).)

FKF1 and GI (Yazawa, M. et al., Nat. Biotechnol. 27, 941-5 (2009).)

CRY2 and CIB1 (Kennedy, M. J., et al., Nat. methods 7, 12-16 (2010).)

UVR8-COP1 (Crefcoeur, R P. et al., Nat. Commun. 4:1779 doi: 10. 1038/ncomms2800 (2013).)

VVD-WC1 (Malzahn, E. et al., Cell, 142, 762-772 (2010).)

PhyB-CRY1 (Hughes, R. M. et al., J. Biol. Chem. 287, 22165-22172 (2012).)

RpBphP1-RpPpsR2 (Bellini, D. et al., Structure, 20, 1436-1446 (2012).)

[Pair Forming a Homodimer]

UVR8 (Chen, D. A. et al., J. Cell Biol. 201, 631-640 (2013).)

EL222 (Motta-Mena, L. B. et al., Nat. Chem. Biol., 10, 196-202 (2014).)

bPac (Stierl, M. et al., Beggiatoa, J. Biol. Chem., 286, 1181-1188 (2001).)

RsLOV (Conrad, K. S. et al., Biochemistry, 52, 378-391 (2013).)

PYP (Fan, H. Y. et al., Biochemistry, 50, 1226-1237 (2011).)

H-NOXA (Zoltowski, B. D. et al., Biochemistry, 47, 7012-7019 (2008).)

YtvA (Zoltowski, B. D. et al., Biochemistry, 47, 7012-7019 (2008).)

NifL (Zoltowski, B. D. et al., Biochemistry, 47, 7012-7019 (2008).)

FixL (Zoltowski, B. D. et al., Biochemistry, 47, 7012-7019 (2008).)

RpBphP1 (Bellini, D. et al., Structure, 20, 1436-1446 (2012).)

CRY2 (Multimer formation) (Zoltowski, B. D. et al., Biochemistry, 47, 7012-7019 (2008).)

In the light switch, the amino acid number of each of the pair may be about 200 or less, about 180 or less, or about 160 or less.

As the light switch, a Magnet which was developed by the present inventors based on the Vivid protein may be used. The Magnet is a set of two different polypeptides which are independently selected from a polypeptide comprising an amino acid sequence of SEQ ID No.: 1, and a mutant polypeptide thereof. Particularly, there is mentioned one having a sequence where one of polypeptides of the set has a sequence in which Ile at a position 52 and Met at a position 55 are substituted with an amino acid having a positive charge on a side chain, in an amino acid sequence of SEQ ID No.: 1 or a sequence having 80% or more, 85% or more, 90% or more, 95% or more, 98% or more, or 99% or more sequence identity with this, and the other polypeptide has a sequence in which Ile at a position 52 and Met at a position 55 are substituted with an amino acid having a negative charge on a side chain, in an amino acid sequence of SEQ ID No.: 1 or a sequence having 80% or more, 85% or more, 90% or more, 95% or more, 98% or more, or 99% or more sequence identity with this.

Herein, the amino acid having a positive charge on a side chain may be a natural amino acid or a non-natural amino acid, and examples of the natural amino acid include lysine, arginine, and histidine. The amino acid having a negative charge on a side chain may be also a natural amino acid or a non-natural amino acid, and examples of the natural amino acid include aspartic acid and glutamic acid.

Specific examples of the Magnet include the following:
pMag and nMag
pMag and nMagHigh1
pMagHigh1 and nMag
pMagHigh1 and nMagHigh1.

Herein, pMag refers to a polypeptide having mutations of I52R and M55R, in an amino acid sequence of SEQ ID No.: 1 or a sequence having 80% or more, 85% or more, 90% or more, 95% or more, 98% or more, or 99% or more sequence identity with this, and pMagHigh1 refers to a polypeptide further containing mutations of M135I and M165I, in the amino acid sequence of pMag.

Additionally, nMag refers to a polypeptide having mutations of I52D and M55G, in an amino acid sequence of SEQ ID NO.: 1 or a sequence having 80% or more, 85% or more, 90% or more, 95% or more, 98% or more, or 99% or more sequence identity with this, and nMagHigh1 refers to a polypeptide further containing mutations of M135I and M165I, in the amino acid sequence of nMag.

The Magnet forms a heterodimer by irradiating blue light, and the heterodimer is rapidly dissociated by stopping light irradiation.

Each polypeptide of the light switch, and the N-terminal side fragment and the C-terminal side fragment of the Cas9 protein can be bound by the known method. Examples thereof include a method of appropriately ligating nucleic acids encoding each of them, and expressing the ligated nucleic acids as a fused polypeptide. In this case, a polypeptide being a linker may intervene between any polypeptide of the light switch, and the N-terminal side fragment or the C-terminal side fragment.

(Set of Two Polypeptides Forming a Dimer in the Presence of a Drug)

The "set of two polypeptides forming a dimer in the presence of a drug" used in the present invention may be the known one. Examples thereof are not limited to, but include a set of FKBP (FK506-binding protein) and FRB (FKBP12-rapamycin associated protein 1 fragment) forming a heterodimer in the presence of rapamycin, a system using gibberellin (compound) and its binding protein (GAI/GID1) (Nat. Chem. Biol. 8, 465-470 (2012) doi: 10.1038/nchembio.922), a system using fusicoccin (compound) and its binding protein (CT52M1/T14-3-3cΔC-M2) (PNAS 110, E377-386 (2013) doi: 10.1073/pnas. 1212990110), a system using abscisic acid (compound) and its binding protein (PYL/ABI) (Science Signaling 4(164), rs2 (2011) DOI: 10.1126/scisignal.2001449), and a system using rCD1/FK506 (compound) and its binding protein (FKBP/SNAP) (Angew. Chem. Int. Ed. 53, 1-5 (2014) DOI: 10.1002/anie.201402294).

Each of the polypeptides forming a dimer in the presence of a drug, and the N-terminal side fragment and the C-terminal side fragment of the Cas9 protein can be bound as in the case of the light switch.

(Nucleic Acid)

The present invention also provides a nucleic acid encoding a polypeptide constituting the set of two polypeptides in accordance with first to fourth aspects.

A term "nucleic acid" in the present specification includes a DNA, an RNA, a chimera of DNA/RNA, and an artificial nucleic acid such as a locked nucleic acid (LNA) and a peptide nucleic acid (PNA), unless particularly described.

Examples of such a nucleic acid include a nucleic acid encoding a fused polypeptide of one polypeptide of the light switch, and the N-terminal side fragment of the Cas9 protein, and a nucleic acid encoding a fused polypeptide of the other polypeptide of the light switch, and the C-terminal side fragment of the Cas9 protein. The nucleic acid may be a nucleic acid encoding a linker polypeptide between any one polypeptide of the light switch, and a fused polypeptide of the N-terminal side fragment or the C-terminal side fragment of the Cas9 protein. When the N-terminal side fragment of the Cas9 protein contains mutation of D10A, and/or when the C-terminal side fragment contains H840A, the nucleic acid is a nucleic acid encoding a sequence containing such mutation.

Additionally, other examples of the nucleic acid of the present invention include a nucleic acid encoding a fused polypeptide of one of polypeptides forming a dimer in the presence of a drug and the N-terminal side fragment of the Cas9 protein, and a nucleic acid encoding a fused polypeptide of the other of polypeptides forming a dimer in the presence of a drug and the C-terminal side fragment of the Cas9 protein. The nucleic acid may be a nucleic acid encoding a linker polypeptide between any one of the set of polypeptides forming a dimer in the presence of a drug, and the fused polypeptide of the N-terminal side fragment or the C-terminal side fragment of the Cas9 protein. When the N-terminal side fragment of the Cas9 protein contains mutation of D10A, and/or, when the C-terminal side fragment contains H840A, the nucleic acid is a nucleic acid encoding a sequence containing such mutation.

The nucleic acid of the present invention can be synthesized according to the known method by a person skilled in the art.

The present invention also includes an expression vector including the nucleic acid of the present invention. In the expression vector of the present invention, any one of nucleic acids encoding each of the set of two polypeptides of the present invention may be inserted, or both of the nucleic acids may be inserted into one vector. Additionally, such a vector may contain a nucleic acid encoding a guide RNA.

The nucleic acid of the present invention as it is, or after digestion with a restriction enzyme, or addition of a linker, can be inserted downstream of a promoter of the expression vector. Examples of the vector are not limited to, but include an *Escherichia coli*-derived plasmid (pBR322, pBR325, pUC12, pUC13, pUC18, pUC19, pUC118, pBluescript II etc.), a *Bacillus subtilis*-derived plasmid (pUB110, pTP5, pC1912, pTP4, pE194, pC194 etc.), a yeast-derived plasmid (pSH19, pSH15, YEp, YRp, YIp, YAC etc.), a bacteriophage phage, M13 phage etc.), a virus (retrovirus, vaccinia virus, adenovirus, adeno-associated virus (AAV), cauliflower mosaic virus, tobacco mosaic virus, baculovirus etc.), a cosmid and the like.

The promoter can be appropriately selected depending on a kind of a host. When the host is an animal cell, for example, a SV40 (simian virus 40)-derived promoter, and a CMV (cytomegalovirus)-derived promoter can be used. When the host is *Escherichia coli*, a trp promoter, a T7 promoter, a lac promoter and the like can be used.

In the expression vector, a DNA replication origin (ori), a selection marker (antibiotic resistance, auxotrophy etc.), an enhancer, a splicing signal, a polyA addition signal, a nucleic acid encoding a tag (FLAG, HA, GST, GFP etc.) and the like may be integrated.

By transforming an appropriate host cell with the aforementioned expression vector, a transformant can be obtained. The host can be appropriately selected in relation with the vector, and for example, *Escherichia coli*, *Bacillus subtilis*, a bacterium of genus *Bacillus*, yeast, an insect, insect cells, animal cells and the like are used. As the animal cells, for example, HEK293T cells, CHO cells, COS cells, myeloma cells, HeLa cells, and Vero cells may be used. Transformation can be performed according to the known method such as a lipofection method, a calcium phosphate method, an electroporation method, a microinjection method, a particle gun method and the like, depending on a kind of the host.

By culturing the transformant according to the conventional method, an objective polypeptide is expressed.

For purifying a protein from the culture of the transformant, cultured cells are recovered, and suspended in an appropriate buffer, and the cells are destructed by a method such as ultrasound treatment, and freezing and thawing, and subjected to centrifugation or filtration to obtain a crude abstract. When the polypeptide is secreted into the culturing liquid, the supernatant is recovered.

Purification from the crude extract or the culturing supernatant can be performed by the known method or another equivalent method (e.g. salting out, dialysis method, ultrafiltration method, gel filtration method, SDS-PAGE method, ion exchange chromatography, affinity chromatography, reversed phase high performance liquid chromatography etc.).

(Kit)

A first aspect of a kit of the present invention is a kit for cutting a target double-stranded nucleic acid, including the "set of two polypeptides exhibiting the nuclease activity" of the present invention, nucleic acids encoding the set of polypeptides, or a vector including the nucleic acids, and a guide RNA including a sequence complementary to one sequence of a target double-stranded nucleic acid or a nucleic acid encoding it.

For example, the kit can be a kit including a total of 3 kinds of nucleic acids of nucleic acids encoding each of the set of two polypeptides exhibiting the nuclease activity, and a nucleic acid encoding the guide RNA, and in the kit, 3 kinds of nucleic acids may be introduced into 1, 2, or 3 vector(s). The guide RNA may be of two or more kinds.

A second aspect of a kit of the present invention is a kit for cutting a target double-stranded nucleic acid, including the "set of two polypeptides exhibiting the nickase activity" of the present invention, or nucleic acids encoding the set of polypeptides, or a vector including the nucleic acids, and a pair of guide RNAs including a sequence complementary to each sequence of the target double-stranded nucleic acid or nucleic acids encoding them.

For example, the kit can be a kit including 4 kinds of nucleic acids of nucleic acids encoding each of the set of two polypeptides exhibiting the nickase activity, and nucleic acids encoding a pair of guide RNAs, and in the kit, 4 kinds of nucleic acids may be inserted into 1, 2, 3 or 4 vector(s). The pair of the guide RNAs may be of two or more.

The first aspect and the second aspect of the kit of the present invention can also be used in genome editing following cutting, and in that case, the kit may be provided with a reagent necessary for NHEJ or HDR.

A third aspect of a kit of the present invention is a kit for suppressing expression of a target gene, including the "set of two polypeptides suppressing gene expression of a target gene" of the present invention, or nucleic acids encoding the set of polypeptides, or a vector including the nucleic acids, and a guide RNA complementary to a partial sequence of a target gene or a nucleic acid encoding it.

For example, the kit can be a kit including a total of 3 kinds of nucleic acids of nucleic acids encoding each of the set of two polypeptides suppressing gene expression of a target gene, and a nucleic acid encoding a guide RNA, and in the kit, 3 kinds of nucleic acids may be inserted into 1, 2, or 3 vector(s). The guide RNA may be two or more kinds.

A fourth aspect of a kit of the present invention is a kit for activating expression of a target gene, including the "set of two polypeptides activating gene expression of a target gene" of the present invention, or nucleic acids encoding the set of polypeptides, or a vector including the nucleic acids, a guide RNA including a sequence complementary to a partial sequence of the target gene with an aptamer introduced therein or a nucleic acid encoding it, and an aptamer-binding protein ligated to a transcription activation domain or a nucleic acid encoding it.

For example, the kit can be a kit including a total of 4 kinds of nucleic acids of nucleic acids encoding each of a set of two polypeptides suppressing gene expression of a target gene, a nucleic acid encoding an aptamer and a guide RNA, as well as a nucleic acid encoding a transcription activation domain and an aptamer-binding protein, and in the kit, 4 kinds of nucleic acids may be introduced into 1, 2, 3, or 4 vector(s). The guide RNA may be of two or more kinds.

In the present invention, a set of two polypeptides activating gene expression of a target gene including a polypeptide, in which VP64 as a transcription activation domain is bound to the C-terminal side fragment of the Cas9 protein; a nucleic acid encoding a guide RNA bound with a MS2-binding sequence, in which an aptamer-binding protein is MS2, and a transcription activation domain is p65 and HSF1; as well as nucleic acids encoding p65, HSF1 and MS2 are suitably used, and as a factor corresponding to VP64, MS2, p65 and HSF1, a transcription activation domain and an aptamer-binding protein such as those disclosed in Nature (2015) 517, 583-588 and nature protocols (2012) 7 (10), 1797-1807 can also be used.

In any of the first, second, third and fourth aspects, the kit of the present invention may be provided with other necessary reagents and instruments, and examples thereof are not limited to, but include various buffers, and a necessary primer, enzyme, manual and the like.

The disclosure of all patent documents and non-patent documents cited in the present specification are incorporated herein by reference as a whole.

EXAMPLES

The present invention will be specifically illustrated based on Examples below, but the present invention is not limited to them. A person skilled in the art can modify the present invention into a variety of aspects without departing from the significance of the present invention, and such modification is also included in the scope of the present invention.
<Methods>
Construction of Inducible Cas9

An N-terminal side and a C-terminal side fragments of *Streptococcus pyogenes*-derived Cas9, in which codons were optimized, and a cDNA encoding a fused polypeptide of NLS derived from SV40 were amplified from the Addgene plasmid 42230 (by Addgene). cDNAs encoding FKBP and FRB were amplified from a human cDNA library. A cDNA encoding CRY2 PHR was amplified from the Addgene plasmid 26871 (by Addgene). A plasmid including CIB1 was obtained from RIKEN Bio Resource Center (Resource Number: pda10875). cDNAs encoding pMag, nMagHigh1, and nMag were prepared according to the previous method (Kawano, F., et al. Nat. Commun. 6, 6256 (2015). Hereinafter, referred to as "Kawano, 2015"). These dimerization domains were amplified by a standard PCR method using a primer, which adds a glycine-serine linker to 5' and 3'-terminuses. A light or drug-dependent Cas9 construct based on an N-terminal side or C-terminal side fragment of Cas9 fused to a dimerization domain was cloned into a HindIII/EcoRI site and a HindIII/XhoI site of pcDNA3.1 V5/His-A (by Invitrogen), respectively. In order to construct a paCas9 nickase and padCas9, D10A mutation was introduced into an N-terminal side fragment of Cas9, and H840A mutation was introduced into a C-terminal side fragment using the Multi Site-Directed Mutagenesis Kit (by MBL) according to a manual, respectively. Full length amino acid sequences of paCas9-1 and paCas9-2 are exhibited in FIGS. 12 to 14.

sgRNA Construction sgRNAs targeting a StopFluc reporter, CCR5, EMX1, VEGFA, AAVS1 and a destabilized luciferase reporter were prepared by annealed oligo cloning using a BbsI site of the Addgene plasmid 47108. Target sequences, and oligonucleotides used for constructing sgRNAs are exhibited in the following Table.

Table 1 exhibits a series of guide RNAs containing one base mismatch to StopFluc-1 used in FIG. 1*f*, and oligonucleotides utilized for construing them. The sequence identifiers for the guide sequences from top to bottom are SEQ ID NOs: 29 to 49; the sequence identifiers for the top strand oligonucleotides from top to bottom are SEQ ID NOs: 50 to 70; and the sequence identifiers for the bottom strand oligonucleotides from top to bottom are SEQ ID NOs: 71 to 91.

Table 2 exhibits a series of guide RNAs containing one base mismatch to StopFluc-2 used in FIG. 1*g*, and oligonucleotides used for constructing them. The sequence identifiers for the guide sequences from top to bottom are SEQ ID NOs: 92 to 111; the sequence identifiers for the top strand oligonucleotides from top to bottom are SEQ ID NOs: 112 to 131; and the sequence identifiers for the bottom strand oligonucleotides from top to bottom are SEQ ID NOs: 132 to 151.

Table 3 exhibits a series of guide RNAs containing one base mismatch to StopFluc-3 used in FIG. 1*h*, and oligonucleotides utilized for construing them. The sequence identifiers for the guide sequences from top to bottom are SEQ ID NOs: 152 to 171; the sequence identifiers for the top strand oligonucleotides from top to bottom are SEQ ID NOs: 172 to 191; and the sequence identifiers for the bottom strand oligonucleotides from top to bottom are SEQ ID NOs: 192 to 211.

Table 4 exhibits nucleotide sequences of guide RNAs targeting CCR5, EMX1, VEGFA, AAVS1, and destabilized luciferase, respectively, and oligonucleotides utilized for constructing them. The sequence identifiers for the guide sequences from top to bottom are SEQ ID NOs: 212 to 220; the sequence identifiers for the top strand oligonucleotides from top to bottom are SEQ ID NOs: 221 to 229; and the sequence identifiers for the bottom strand oligonucleotides from top to bottom are SEQ ID NOs: 230 to 238.

TABLE 1

Stop codon-inserted luciferase reporter - 1(StopFluc-1)

Guide sequence of sgRNA

| Name | 21 | 20 | 19 | 18 | 17 | 16 | 15 | 14 | 13 | 12 | 11 | 10 | 9 | 8 | 7 | 6 | 5 | 4 | 3 | 2 | 1 |
|---|---|---|---|---|---|---|---|---|---|---|---|---|---|---|---|---|---|---|---|---|---|
| original sgRNA | G | A | A | C | T | T | G | C | A | C | G | A | G | A | T | C | T | A | A | A | G |
| m1  | G | A | A | C | T | T | G | C | A | C | G | A | G | A | T | C | T | A | A | A | c |
| m2  | G | A | A | C | T | T | G | C | A | C | G | A | G | A | T | C | T | A | A | t | G |
| m3  | G | A | A | C | T | T | G | C | A | C | G | A | G | A | T | C | T | A | t | A | G |
| m4  | G | A | A | C | T | T | G | C | A | C | G | A | G | A | T | C | T | t | A | A | G |
| m5  | G | A | A | C | T | T | G | C | A | C | G | A | G | A | T | C | a | A | A | A | G |
| m6  | G | A | A | C | T | T | G | C | A | C | G | A | G | A | T | g | T | A | A | A | G |
| m7  | G | A | A | C | T | T | G | C | A | C | G | A | G | A | a | C | T | A | A | A | G |
| m8  | G | A | A | C | T | T | G | C | A | C | G | A | G | t | T | C | T | A | A | A | G |
| m9  | G | A | A | C | T | T | G | C | A | C | G | A | c | A | T | C | T | A | A | A | G |
| m10 | G | A | A | C | T | T | G | C | A | C | G | t | G | A | T | C | T | A | A | A | G |
| m11 | G | A | A | C | T | T | G | C | A | C | c | A | G | A | T | C | T | A | A | A | G |
| m12 | G | A | A | C | T | T | G | C | A | g | G | A | G | A | T | C | T | A | A | A | G |
| m13 | G | A | A | C | T | T | G | C | t | C | G | A | G | A | T | C | T | A | A | A | G |
| m14 | G | A | A | C | T | T | G | g | A | C | G | A | G | A | T | C | T | A | A | A | G |
| m15 | G | A | A | C | T | T | c | C | A | C | G | A | G | A | T | C | T | A | A | A | G |
| m16 | G | A | A | C | T | a | G | C | A | C | G | A | G | A | T | C | T | A | A | A | G |
| m17 | G | A | A | C | a | T | G | C | A | C | G | A | G | A | T | C | T | A | A | A | G |
| m18 | G | A | A | g | T | T | G | C | A | C | G | A | G | A | T | C | T | A | A | A | G |
| m19 | G | A | t | C | T | T | G | C | A | C | G | A | G | A | T | C | T | A | A | A | G |
| m20 | G | t | A | C | T | T | G | C | A | C | G | A | G | A | T | C | T | A | A | A | G |

| Name | oligonucleotide (for top strand) | oligonucleotide (for bottom strand) |
|---|---|---|
| original sgRNA | CACCGAACTTGCACGAGATCTAAAG | AAACCTTTAGATCTCGTGCAAGTTC |
| m1  | CACCGAACTTGCACGAGATCTAAAC | AAACGTTTAGATCTCGTGCAAGTTC |
| m2  | CACCGAACTTGCACGAGATCTAATG | AAACCATTAGATCTCGTGCAAGTTC |
| m3  | CACCGAACTTGCACGAGATCTATAG | AAACCTATAGATCTCGTGCAAGTTC |
| m4  | CACCGAACTTGCACGAGATCTTAAG | AAACCTTAAGATCTCGTGCAAGTTC |
| m5  | CACCGAACTTGCACGAGATCAAAAG | AAACCTTTTGATCTCGTGCAAGTTC |
| m6  | CACCGAACTTGCACGAGATGTAAAG | AAACCTTTACATCTCGTGCAAGTTC |
| m7  | CACCGAACTTGCACGAGAACTAAAG | AAACCTTTAGTTCTCGTGCAAGTTC |
| m8  | CACCGAACTTGCACGAGTTCTAAAG | AAACCTTTAGAACTCGTGCAAGTTC |
| m9  | CACCGAACTTGCACGACATCTAAAG | AAACCTTTAGATGTCGTGCAAGTTC |
| m10 | CACCGAACTTGCACGTGATCTAAAG | AAACCTTTAGATCACGTGCAAGTTC |
| m11 | CACCGAACTTGCACCAGATCTAAAG | AAACCTTTAGATCTGGTGCAAGTTC |
| m12 | CACCGAACTTGCAGGAGATCTAAAG | AAACCTTTAGATCTCCTGCAAGTTC |
| m13 | CACCGAACTTGCTCGAGATCTAAAG | AAACCTTTAGATCTCGAGCAAGTTC |
| m14 | CACCGAACTTGGACGAGATCTAAAG | AAACCTTTAGATCTCGTCCAAGTTC |
| m15 | CACCGAACTTCCACGAGATCTAAAG | AAACCTTTAGATCTCGTGGAAGTTC |
| m16 | CACCGAACTAGCACGAGATCTAAAG | AAACCTTTAGATCTCGTGCTAGTTC |

TABLE 1-continued

Stop codon-inserted luciferase reporter - 1(StopFluc-1)

| | | |
|---|---|---|
| m17 | CACCGAACATGCACGAGATCTAAAG | AAACCTTTAGATCTCGTGCATGTTC |
| m18 | CACCGAAGTTGCACGAGATCTAAAG | AAACCTTTAGATCTCGTGCAACTTC |
| m19 | CACCGATCTTGCACGAGATCTAAAG | AAACCTTTAGATCTCGTGCAAGATC |
| m20 | CACCGTACTTGCACGAGATCTAAAG | AAACCTTTAGATCTCGTGCAAGTAC |

TABLE 2

Stop codon-inserted luciferase reporter - 2(StopFluc-2)

| Name | \multicolumn{20}{c}{Guide sequence of sgRNA} |
|---|---|---|---|---|---|---|---|---|---|---|---|---|---|---|---|---|---|---|---|---|
| | 20 | 19 | 18 | 17 | 16 | 15 | 14 | 13 | 12 | 11 | 10 | 9 | 8 | 7 | 6 | 5 | 4 | 3 | 2 | 1 |
| original sgRNA | G | C | A | G | A | A | G | C | T | A | T | G | A | A | G | T | A | A | T | A |
| m1 | G | C | A | G | A | A | G | C | T | A | T | G | A | A | G | T | A | A | T | T |
| m2 | G | C | A | G | A | A | G | C | T | A | T | G | A | A | G | T | A | A | A | A |
| m3 | G | C | A | G | A | A | G | C | T | A | T | G | A | A | G | T | A | T | T | A |
| m4 | G | C | A | G | A | A | G | C | T | A | T | G | A | A | G | T | T | A | T | A |
| m5 | G | C | A | G | A | A | G | C | T | A | T | G | A | A | G | A | A | A | T | A |
| m6 | G | C | A | G | A | A | G | C | T | A | T | G | A | A | C | T | A | A | T | A |
| m7 | G | C | A | G | A | A | G | C | T | A | T | G | A | T | G | T | A | A | T | A |
| m8 | G | C | A | G | A | A | G | C | T | A | T | G | T | A | G | T | A | A | T | A |
| m9 | G | C | A | G | A | A | G | C | T | A | T | ? | A | A | G | T | A | A | T | A |
| m10 | G | C | A | G | A | A | G | C | T | A | ? | G | A | A | G | T | A | A | T | A |
| m11 | G | C | A | G | A | A | G | C | T | ? | T | G | A | A | G | T | A | A | T | A |
| m12 | G | C | A | G | A | A | G | C | ? | A | T | G | A | A | G | T | A | A | T | A |
| m13 | G | C | A | G | A | A | G | ? | T | A | T | G | A | A | G | T | A | A | T | A |
| m14 | G | C | A | G | A | A | ? | C | T | A | T | G | A | A | G | T | A | A | T | A |
| m15 | G | C | A | G | A | ? | G | C | T | A | T | G | A | A | G | T | A | A | T | A |
| m16 | G | C | A | G | ? | A | G | C | T | A | T | G | A | A | G | T | A | A | T | A |
| m17 | G | C | A | ? | A | A | G | C | T | A | T | G | A | A | G | T | A | A | T | A |
| m18 | G | C | ? | G | A | A | G | C | T | A | T | G | A | A | G | T | A | A | T | A |
| m19 | G | ? | A | G | A | A | G | C | T | A | T | G | A | A | G | T | A | A | T | A |

| Name | oligonucleotide (for top strand) | oligonucleotide (for bottom strand) |
|---|---|---|
| original sgRNA | CACCGCAGAAGCTATGAAGTAATA | AAACTATTACTTCATAGCTTCTGC |
| m1 | CACCGCAGAAGCTATGAAGTAATT | AAACAATTACTTCATAGCTTCTGC |
| m2 | CACCGCAGAAGCTATGAAGTAAAA | AAACTTTTACTTCATAGCTTCTGC |
| m3 | CACCGCAGAAGCTATGAAGTATTA | AAACTAATACTTCATAGCTTCTGC |
| m4 | CACCGCAGAAGCTATGAAGTTATA | AAACTATAACTTCATAGCTTCTGC |
| m5 | CACCGCAGAAGCTATGAAGAAATA | AAACTATTTCTTCATAGCTTCTGC |
| m6 | CACCGCAGAAGCTATGAACTAATA | AAACTATTAGTTCATAGCTTCTGC |
| m7 | CACCGCAGAAGCTATGATGTAATA | AAACTATTACATCATAGCTTCTGC |
| m8 | CACCGCAGAAGCTATGTAGTAATA | AAACTATTACTACATAGCTTCTGC |

TABLE 2-continued

Stop codon-inserted luciferase reporter - 2(StopFluc-2)

| | | |
|---|---|---|
| m9 | CACCGCAGAAGCTATCAAGTAATA | AAACTATTACTTGATAGCTTCTGC |
| m10 | CACCGCAGAAGCTAAGAAGTAATA | AAACTATTACTTCTTAGCTTCTGC |
| m11 | CACCGCAGAAGCTTTGAAGTAATA | AAACTATTACTTCAAAGCTTCTGC |
| m12 | CACCGCAGAAGCAATGAAGTAATA | AAACTATTACTTCATTGCTTCTGC |
| m13 | CACCGCAGAAGGTATGAAGTAATA | AAACTATTACTTCATACCTTCTGC |
| m14 | CACCGCAGAACCTATGAAGTAATA | AAACTATTACTTCATAGGTTCTGC |
| m15 | CACCGCAGATGCTATGAAGTAATA | AAACTATTACTTCATAGCATCTGC |
| m16 | CACCGCAGTAGCTATGAAGTAATA | AAACTATTACTTCATAGCTACTGC |
| m17 | CACCGCACAAGCTATGAAGTAATA | AAACTATTACTTCATAGCTTGTGC |
| m18 | CACCGCTGAAGCTATGAAGTAATA | AAACTATTACTTCATAGCTTCAGC |
| m19 | CACCGGAGAAGCTATGAAGTAATA | AAACTATTACTTCATAGCTTCTCC |

TABLE 3

Stop codon-inserted luciferase reporter - 3(StopFluc-3)

| Name | \multicolumn{20}{c}{Guide sequence of sgRNA} | | | | | | | | | | | | | | | | | | | |
|---|---|---|---|---|---|---|---|---|---|---|---|---|---|---|---|---|---|---|---|---|
| | 20 | 19 | 18 | 17 | 16 | 15 | 14 | 13 | 12 | 11 | 10 | 9 | 8 | 7 | 6 | 5 | 4 | 3 | 2 | 1 |
| original sgRNA | G | G | T | G | C | C | C | T | G | T | T | C | A | T | C | T | A | A | G | |
| m1 | G | G | G | T | G | C | C | C | T | G | T | T | C | A | T | C | T | A | A | C |
| m2 | G | G | G | T | G | C | C | C | T | G | T | T | C | A | T | C | T | A | T | G |
| m3 | G | G | G | T | G | C | C | C | T | G | T | T | C | A | T | C | T | T | A | G |
| m4 | G | G | G | T | G | C | C | C | T | G | T | T | C | A | T | C | G | A | A | G |
| m5 | G | G | G | T | G | C | C | C | T | G | T | T | C | A | T | G | T | A | A | G |
| m6 | G | G | G | T | G | C | C | C | T | G | T | T | C | A | G | C | T | A | A | G |
| m7 | G | G | G | T | G | C | C | C | T | G | T | T | C | G | T | C | T | A | A | G |
| m8 | G | G | G | T | G | C | C | C | T | G | T | T | G | A | T | C | T | A | A | G |
| m9 | G | G | G | T | G | C | C | C | T | G | T | G | C | A | T | C | T | A | A | G |
| m10 | G | G | G | T | G | C | C | C | T | G | G | T | C | A | T | C | T | A | A | G |
| m11 | G | G | G | T | G | C | C | C | T | G | T | T | C | A | T | C | T | A | A | G |
| m12 | G | G | G | T | G | C | C | C | G | G | T | T | C | A | T | C | T | A | A | G |
| m13 | G | G | G | T | G | C | C | G | T | G | T | T | C | A | T | C | T | A | A | G |
| m14 | G | G | G | T | G | C | G | C | T | G | T | T | C | A | T | C | T | A | A | G |
| m15 | G | G | G | T | G | G | C | C | T | G | T | T | C | A | T | C | T | A | A | G |
| m16 | G | G | G | T | G | C | C | C | T | G | T | T | C | A | T | C | T | A | A | G |
| m17 | G | G | G | G | G | C | C | C | T | G | T | T | C | A | T | C | T | A | A | G |
| m18 | G | G | G | T | G | C | C | C | T | G | T | T | C | A | T | C | T | A | A | G |
| m19 | G | G | G | T | G | C | C | C | T | G | T | T | C | A | T | C | T | A | A | G |

| Name | oligonucleotide (for top strand) | oligonucleotide (for bottom strand) |
|---|---|---|
| original sgRNA | CACCGGGTGCCCTGTTCATCTAAG | AAACCTTAGATGAACAGGGCACCC |
| m1 | CACCGGGTGCCCTGTTCATCTAAC | AAACGTTAGATGAACAGGGCACCC |

TABLE 3-continued

Stop codon-inserted luciferase reporter - 3(StopFluc-3)

| m2 | CACCGGGTGCCCTGTTCATCTATG | AAACCATAGATGAACAGGGCACCC |
| --- | --- | --- |
| m3 | CACCGGGTGCCCTGTTCATCTTAG | AAACCTAAGATGAACAGGGCACCC |
| m4 | CACCGGGTGCCCTGTTCATCAAAG | AAACCTTTGATGAACAGGGCACCC |
| m5 | CACCGGGTGCCCTGTTCATGTAAG | AAACCTTACATGAACAGGGCACCC |
| m6 | CACCGGGTGCCCTGTTCAACTAAG | AAACCTTAGTTGAACAGGGCACCC |
| m7 | CACCGGGTGCCCTGTTCTTCTAAG | AAACCTTAGAAGAACAGGGCACCC |
| m8 | CACCGGGTGCCCTGTTGATCTAAG | AAACCTTAGATCAACAGGGCACCC |
| m9 | CACCGGGTGCCCTGTACATCTAAG | AAACCTTAGATGTACAGGGCACCC |
| m10 | CACCGGGTGCCCTGATCATCTAAG | AAACCTTAGATGATCAGGGCACCC |
| m11 | CACCGGGTGCCCTCTTCATCTAAG | AAACCTTAGATGAAGAGGGCACCC |
| m12 | CACCGGGTGCCCAGTTCATCTAAG | AAACCTTAGATGAACTGGGCACCC |
| m13 | CACCGGGTGCCGTGTTCATCTAAG | AAACCTTAGATGAACACGGCACCC |
| m14 | CACCGGGTGCGCTGTTCATCTAAG | AAACCTTAGATGAACAGCGCACCC |
| m15 | CACCGGGTGGCCTGTTCATCTAAG | AAACCTTAGATGAACAGGCCACCC |
| m16 | CACCGGGTCCCCTGTTCATCTAAG | AAACCTTAGATGAACAGGGACCC |
| m17 | CACCGGGAGCCCTGTTCATCTAAG | AAACCTTAGATGAACAGGGCTCCC |
| m18 | CACCGGCTGCCCTGTTCATCTAAG | AAACCTTAGATGAACAGGGCAGCC |
| m19 | CACCGCGTGCCCTGTTCATCTAAG | AAACCTTAGATGAACAGGGCACGC |

| Name | | | | | | | | | | | | | | | | | | | | | | Guide sequence of sgRNA | Oligonucleotide | |
|---|---|---|---|---|---|---|---|---|---|---|---|---|---|---|---|---|---|---|---|---|---|---|---|---|
| | | | | | | | | | | | | | | | | | | | | | | human CCR5 locus | | |
| | 21 | 20 | 19 | 18 | 17 | 16 | 15 | 14 | 13 | 12 | 11 | 10 | 9 | 8 | 7 | 6 | 5 | 4 | 3 | 2 | 1 | (for top strand) | (for bottom strand) | |
| sgRNA_CCR5 | G | T | G | A | C | A | T | C | A | A | T | T | A | T | T | A | T | A | C | A | T | CACCGTGACATCAATTATTATACAT | AAACATGTATAATAATTGATGTCAC |

| Name | | | | | | | | | | | | | | | | | | | | | Guide sequence of sgRNA | Oligonucleotide | |
|---|---|---|---|---|---|---|---|---|---|---|---|---|---|---|---|---|---|---|---|---|---|---|---|---|
| | | | | | | | | | | | | | | | | | | | | | | human EMX1 locus | | |
| | | 20 | 19 | 18 | 17 | 16 | 15 | 14 | 13 | 12 | 11 | 10 | 9 | 8 | 7 | 6 | 5 | 4 | 3 | 2 | 1 | (for top strand) | (for bottom strand) | |
| sgRNA_EMX1 | | G | A | G | T | C | C | G | A | G | C | A | G | A | A | G | A | A | G | A | A | CACCGAGTCCGAGCAGAAGAAGAA | AAACTTCTTCTGCTCGGACTC |
| sgRNA_E2 (for nickase) | | G | C | C | T | G | T | T | T | G | C | A | C | T | T | T | G | T | C | T | C | CACCGCGTTTGTACTTTGTCTC | AAACGAGACAAAGTACAAACGGC |

| Name | | | | | | | | | | | | | | | | | | | | | Guide sequence of sgRNA | Oligonucleotide | |
|---|---|---|---|---|---|---|---|---|---|---|---|---|---|---|---|---|---|---|---|---|---|---|---|---|
| | | | | | | | | | | | | | | | | | | | | | | human VEGFA locus | | |
| | | 20 | 19 | 18 | 17 | 16 | 15 | 14 | 13 | 12 | 11 | 10 | 9 | 8 | 7 | 6 | 5 | 4 | 3 | 2 | 1 | (for top strand) | (for bottom strand) | |
| sgRNA_VEGFA | | G | G | T | G | A | G | T | G | A | G | T | G | T | G | T | G | C | G | T | G | CACCGGTGAGTGAGTGTGTGCGTG | AAACCACGCACACACTCACTCACC |

| Name | | | | | | | | | | | | | | | | | | | | | Guide sequence of sgRNA | Oligonucleotide | |
|---|---|---|---|---|---|---|---|---|---|---|---|---|---|---|---|---|---|---|---|---|---|---|---|---|
| | | | | | | | | | | | | | | | | | | | | | | human AAVS1 locus | | |
| | 21 | 20 | 19 | 18 | 17 | 16 | 15 | 14 | 13 | 12 | 11 | 10 | 9 | 8 | 7 | 6 | 5 | 4 | 3 | 2 | 1 | (for top strand) | (for bottom strand) | |
| sgRNA_AAVS1 (site1) | G | C | T | C | C | C | T | C | C | C | A | G | G | A | T | C | C | T | C | T | C | CACCGCTCCCTCCCCAGGATCCTCTC | AAACGAGAGGTCCTGGGAGGGAGC |
| sgRNA_AAVS1 (site2) | G | G | G | A | A | G | G | A | G | G | A | G | G | C | T | T | G | G | C | A | G | CACCGGGAGGAGAGCTTGGCAGG | AAACCCTGCCAAGCTCTCCCTCCC |

| Name | | | | | | | | | | | | | | | | | | | | | Guide sequence of sgRNA | Oligonucleotide | |
|---|---|---|---|---|---|---|---|---|---|---|---|---|---|---|---|---|---|---|---|---|---|---|---|---|
| | | | | | | | | | | | | | | | | | | | | | | destabilized luciferase reporter | | |
| | 21 | 20 | 19 | 18 | 17 | 16 | 15 | 14 | 13 | 12 | 11 | 10 | 9 | 8 | 7 | 6 | 5 | 4 | 3 | 2 | 1 | (for top strand) | (for bottom strand) | |
| sgFluc-1 | G | T | T | T | G | T | G | C | A | G | C | T | G | C | T | C | G | C | C | G | G | CACCGTTTGTGCAGCTGCTCGCCGG | AAACCCGGCGAGCAGCTGCACAAAC |
| sgFluc-2 | G | G | T | C | C | A | C | C | T | C | G | A | T | A | T | G | T | G | C | G | T | CACCGGTCCACCTCGATATGTGCGT | AAACACGCACATATCGAGGTGGAC |
| sgFluc-3 | G | C | C | G | C | T | G | G | A | T | C | C | G | T | G | G | T | G | C | A | A | CACCGCCGCTGGATCCGTGGTGCAA | AAACTTGCACCACGGATCCAGCGGC |
| sgNeg. | G | | | | | | | | | | | | | | | | | | | | | | |

Reporter Construction

A StopFluc reporter for the plasmid HDR assay was constructed by inserting a firefly luciferase sequence which had been amplified from the pGL4.31 vector (by Promega) into a HindIII site and a XhoI site of pcDNA3.1/V5-HisA, and introducing a stop codon and/or mutated PAM by the Multi Site-Directed Mutagenesis Kit. Site-directed mutagenesis primers used for preparing a series of StopFluc reporters are exhibited in the following Table.

TABLE 5

| Primer name | Primer sequence (5 to 3') |
| --- | --- |
| StopFluc-1 | AACTTGCACGAGATCTAAAGCGGCGGGGCGCCG |
| StopFluc-2 | GCAGAAGCTATGAAGTAATATGGGCTGAATACA |
| StopFluc-3 | GGTGCCCTGTTCATCTAAGTGGCTGTGGCCCCA |
| StopFluc-1 (CAG PAM) | GCACGAGATCTAAAGCAGCGGGGCGCCGCTCAG |
| StopFluc-1 (CTG PAM) | GCACGAGATCTAAAGCTGCGGGGCGCCGCTCAG |
| StopFluc-1 (CCG PAM) | GCACGAGATCTAAAGCCGCGGGGCGCCGCTCAG |
| StopFluc-1 (CGA PAM) | GCACGAGATCTAAAGCGACGGGGCGCCGCTCAG |
| StopFluc-1 (CGT PAM) | GCACGAGATCTAAAGCGTCGGGGCGCCGCTCAG |
| StopFluc-1 (CGC PAM) | GCACGAGATCTAAAGCGCCGGGGCGCCGCTCAG |
| StopFluc-2 (TAG PAM) | AGCTATGAAGTWATAGGCTGAATACAAACCA |
| StopFluc-2 (TCG PAM) | AGCTATGAAGTAATATCGGCTGAATACAAACCA |
| StopFluc-2 (TTG PAM) | AGCTATGAAGTAATATTGGCTGAATACAAACCA |
| StopFluc-2 (TGA PAM) | AGCTATGAAGTAATATGAGCTGAATACAAACCA |
| StopFluc-2 (TGC PAM) | AGCTATGAAGTAATATGCGCTGWACAAACCA |
| StopFluc-2 (TGT PAM) | AGCTATGAAGTAATATGTGCTGAATACAAACCA |

The sequence identifiers for the sequences in Table 5 from top to bottom are SEQ ID NOs: 239 to 253.

DNA sequences of StopFluc reporters are exhibited in FIGS. 15 to 17. A luciferase donor vector was constructed by inserting an inverted sequence of firefly luciferase into XhoI and HindIII sites of the bacterium expression pColdI vector (by Clontech). A destabilized luciferase reporter was constructed by inserting firefly luciferase and PEST sequences which had been amplified from the pGL4.31 vector into KpnI and XbaI sites of pcDNA3.1N5-HisA, and introducing 5 copies of a mRNA destabilized nonamer sequence (5'-TTATTTATT-3') (Voon, D. C. et al. Nucleic Acids Res. 33, e27 (2005).) into XbaI and ApaI sites by annealed oligo cloning. A surrogate EGFP reporter was constructed by inserting mCherry and out-of-frame EGFP into HindIII and XhoI sites of pcDNA 3.1N5-HisA, and introducing an EMX1 target site between mCherry and EGFP using EcoRI and BamHI sites, by annealed oligo cloning.

Cell Culturing

HEK293T cells and HeLa cells were cultured under the condition of 37° C. and 5% $CO_2$ in the Dulbecco's Modified Eagle Medium (DMEM, by Sigma Aldrich) with 10% FBS (HyClone), 100 unit/ml penicillin, and 100 µg/mL streptomycin (GIBCO) added thereto.

Luciferase Plasmid HDR Assay

HEK293T cells were seeded on the 96-well black-walled plate (by Thermo Fisher Scientific) at about $2.0 \times 10^4$ cells/well, and cultured under the condition of 37° C. and 5% $CO_2$ for 24 hours. The cells were transfected with Lipofectamine 2000 (by Invitrogen) according to a manual. The cells were transfected with an N-terminal side fragment of Cas9 fused with a dimerization domain, a C-terminal side fragment of Cas9 fused with a dimerization domain, a sgRNA, a StopFluc reporter, and a plasmid encoding a luciferase donor at the ratio of 2.5:2.5:5:1:4. A total amount of a DNA was 0.2 µg/well. Twenty four hours after transfection, the sample was placed in a dark place, continuously irradiated with blue light, and incubated under the condition of 37° C. and 5% $CO_2$. Blue light irradiation was performed using a LED light source at 470 nm±20 nm (by CCS Inc.). The intensity of blue light was 1.2 $W/m^2$. For rearrangement of drug dependency of divided Cas9, in place of light irradiation, the medium was changed to 100 µL of DMEM containing 10 nM rapamycin. After incubation for 48 hours, the medium was changed to 100 µL of a DMEM medium (by Sigma Aldrich) containing 500 µM D-luciferin (by Wako Pure Chemical Industries) as a substrate, and not containing phenol red. After incubation was performed for 30 minutes, bioluminescence was measured using the Centro XS3 LB 960 plate-reading luminometer (by Berthold Technologies). In order to compare the DNA recognizing abilities of paCas9 and full length Cas9, the cells were transfected with full length Cas9, a sgRNA, a StopFluc reporter, and a plasmid encoding a luciferase donor at the ratio of 5:5:1:4. A total amount of a DNA was 0.2 µg/well. After incubation for 48 hours, the medium was exchanged with a DMEM medium containing D-luciferin and not containing phenol red, and bioluminescence was measured by the aforementioned method.

Optogenetic Genome Editing Experiment

For an indel mutation introduction experiment by NHEJ, HEK293T cells were seeded on a 24-well plate (by Thermo Fisher Scientific) at about $1.0 \times 10^5$ cells/well, and cultured under the condition of 38° C. and 5% $CO_2$ for 24 hours. The cells were transfected using Lipofectamine 2000 according to a manual. The cells were transfected with N713-pMag, nMagHigh1-C714 (FIGS. 12 and 13), and a plasmid encoding a sgRNA at the ratio of 1:1:1. The cells were transfected with plasmids encoding full length Cas9 and a sgRNA, as a positive control, at the ratio of 2:1. A total amount of a DNA was 0.9 µg/well. Twenty four hours after transfection, the cells were incubated under the condition of 37° C. and 5% $CO_2$, by the aforementioned method, while the sample was placed in a dark place, and continuous blue light irradiation was performed. Twenty four hours after incubation, a genomic DNA was isolated by the Blood Cultured Cell Genomic DNA Extraction Mini11 Kit (by Favorgen) according to a manual. For a genome editing experiment by HDR, $6.0 \times 10^5$ HEK293T cells were nucleofected with 125 ng of N713-pMag, 125 ng of MagHigh1C-714, 250 ng of a sgRNA targeting EMX1, and a 10 µM single-stranded oligonucleotide donor, using the SF Cell line 4D-Nucleofector X kit S (by Lonza) and the CA-189 program. The transfected cells were seeded on a 24-well plate at $2.0 \times 10^5$ cells/well. Twenty hours after Nucleofection, the sample was incubated under the condition of 37° C. and 5% $CO_2$, while it was placed in a dark place, and continuous blue light irradiation was performed. Forty eight hours after incubation, a genomic DNA was isolated by the aforementioned method.

In an experiment of FIG. 3F, cells were seeded and cultured by the aforementioned method, and subjected to an indel mutation experiment by NHEJ. The cells were then transfected with Lipofectamine 3000 (by Invitrogen). The cells were transfected with N713-pMag, nMagHigh1-C714, and a plasmid encoding a sgRNA at the ratio of 1:1:1. A total amount of a DNA was 0.5 µg/well. From immediately after transfection, the sample was continuously irradiated with blue light, and incubated under the condition of 37° C. and 5% $CO_2$. After 6 hours, the incubated cells were classified into a group to be placed in a dark place and a group to be placed in a bright place, and second transfection with a sgRNA targeting EMX1 was performed using Lipofectamine 3000. A DNA amount was 0.5 µg/well. The sample which had been placed in a dark place or a bright place until immediate before second transfection was placed in a dark place and a bright place again, respectively. After incubation for 30 hours, a genomic DNA was isolated by the aforementioned method.

Mismatch-Sensitive T7E1 Assay for Quantitating Indel Mutation of an Endogenous Gene A genome region containing a paCas9 target site was PCR-amplified with the Pyrobest DNA polymerase (by TaKaRa) using nested PCR to CCR5 and AAVS1 (first PCR: 98° C., 3 minutes; (98° C., 10 seconds; 55° C., 30 seconds; 72° C., 1 minute)×20 cycles; 72° C., 3 minutes. second PCR: 98° C., 3 minutes; (98° C., 10 seconds; 55° C., 30 seconds; 72° C., 1 minute)×35 cycles; 72° C., 3 minutes). Two-stage PCR using 5% DMSO to EMX1 (98° C., 3 minutes; (98° C., 10 seconds; 72° C., 30 seconds)×35 cycles; 72° C., 5 minutes), or touchdown PCR to VEGFA (98° C., 3 minutes; (98° C., 10 seconds; 72-62° C., -1° C./cycle, 30 seconds; 72° C., 30 seconds)×10 cycles; (98° C., 10 seconds; 62° C., 30 seconds; 72° C., 30 seconds)×25 cycles; 72° C., 3 minutes). Primers for each gene are exhibited in the following Table.

TABLE 6

List of primers used for PCR amplification.

| Target | Primer name | Sequence |
|---|---|---|
| CCR5 | 1st PCR-Forward | CTCCATGGTGCTATAGAGCA |
|  | 2nd PCR-Forward | GAGCCAAGCTCTCCATCTAGT |
|  | Reverse | GCCCTGTCAAGAGTTGACAC |
| AAVS1 | 1st PCR-Forward | GGAGTTTTCCACACGGACAC |
|  | 2nd PCR-Forward | TGCTTCTCCTCTTGGGAAGT |
|  | 1st PCR-Reverse | CCCCTATGTCCACTTCAGGA |
|  | 2nd PCR-reverse | CGGTTAATGTGGCTCTGGIT |
| EMX1 | Forward | GGAGCAGCTGGTCAGAGGGG |
|  | Reverse | GGGAAGGGGACACTGGGGA |
| VEGFA | Forward | TCCAGATGGCACATTGTCAG |
|  | Reverse | AGGGAGCAGGAAAGTGAGGT |

Single-stranded oligonucleotide used in light-induced NOR experiment.

| Name | Sequence |
|---|---|
| EMX1 ssODN | AAACGGCAGAAGCTGGAGGAGGAAGGGCCTGAGTCCGAGCAG CAAGAAGTTAAGGGCTCCCATCACATCAACCGGTGGCGCATT GCCACGAAGCAG |

The sequence identifiers for the primers of Table 6 from top to bottom are SEQ ID NOs: 254 to 264, and the sequence identifiers for EMX1 and ssODN are SEQ ID NOs: 265 and 266, respectively.

The PCR product was purified using the FastGene Gel/PCR Extraction Kits (by Nippon Genetics) according to a manual. The purified PCR product was mixed with 24 of the 10×M buffer (by TaKaRa) for a restriction enzyme, ultrapure water was added to 20 µL, and a hetero double-stranded DNA was formed by re-annealing (95° C., 10 minutes; 90-15° C., -1° C./1 minute). After re-annealing, the hetero double-stranded DNA was treated with 5 units of the T7 endonuclease I (by New England Biolabs) at 37° C. for 30 minutes, and subsequently, analyzed by agarose gel electrophoresis. A gel was stained with GRR-500 (BIO CRAFT), and imaged by the E-shot II gel imaging system (by ATTO). Quantitation was performed based on the relative size of bands. Percentage of indel mutation with paCas9 was calculated according to the following expression.

$$100 \times (1-(1-(b+c)/(a+b+c))^{1/2})$$

In the expression, a is the intensity of the undigested PCR product, and b and c are the intensity of the PCR product which was digested with T7E1, respectively.

Sequence Analysis

The purified PCR product used in the T7E1 assay was inserted into an EcoRV site of the DNA3.1/V5-HisA vector. A plasmid DNA was isolated with standard alkaline lysis miniprep, and a sequence was analyzed by the Sanger method using a T7 forward primer.

RFLP Assay for Detecting Modification with HDR of an Endogenous Human Gene

Genome PCR and purification were performed by the aforementioned method. Ultrapure water was added to 24 of the 10×M buffer for 30 units of HindIII (by TaKaRa), a restriction enzyme to a total amount of 20 µL, and mixed with the purified PCR product, and the mixture was incubated at 37° C. for 30 minutes. The digested products were analyzed by agarose gel electrophoresis. Staining and imaging of the gel were performed by the aforementioned method. Quantitation was performed based on the relative size of bands. Percentage of HDR by paCas9 was calculated according to the following expression.

$$100 \times (b+c)/(a+b+c)$$

In the expression, a is the intensity of the undigested PCR product, and b and c are the intensity of the product which was digested with HindIII, respectively.

Spatial Activation of a Surrogate Reporter

HEK293T cells were seeded on a 35 mm dish (by Iwaki Glass) coated with fibronectin (by BD Biosciences) at $8.0 \times 10^5$ cells/dish, and cultured under the condition of 37° C. and 5% $CO_2$ for 24 hours. The cells were transfected using Lipfectamin 2000 according to a manual. The cells were transfected with sgRNAs targeting N713-pMag, nMag-Cas9, and EMX1, and a plasmid encoding an NHEJ-mediated surrogate EGFP reporter containing an EMX1 target site at the ratio of 1:1:2:6. A total amount of a DNA was 4.0 µg/dish. Twenty hours after transfection, the sample was irradiated with blue light of a slit pattern using a photomask under the condition of 24 hours, 37° C. and 5% $CO_2$. The width of a slit was 2 mm. The cells were fixed with 4% paraformaldehyde (in PBS) for 15 minutes. An image was obtained with the Axio Zoom.V16 stereo zoom microscope (by Zeiss), and analyzed with the Metamorph (by Molecular Devices).

Light Inducible CRISPR Interference

HEK293T cells were seeded on a 96-well black wall plate at $2.0 \times 10^4$ cells/well, and cultured under the condition of 37° C. and 5% $CO_2$ for 24 hours. The cells were transfected with Lipfectamin 2000 according to a manual. The cells were transfected with depicted sgRNAs targeting N713 (D10A)-pMag, nMag-Cas9 (H840A), a mRNA destabilized luciferase-PEST reporter, and a luciferase reporter at 2.5:2.5:1:4. When transfected with three sgRNAs, each sgRNA was 1:1:1. A total amount of a DNA was 0.1 μg/well. In an experiment of FIG. 4b, twenty hours after transfection, the sample was placed in a dark place, and incubated under the condition of 37° C. and 5% $CO_2$ while blue light was continuously irradiated by the aforementioned method. After 30 hours, a medium was exchanged with a DMEM medium containing 100 μl of 500 μM D-luciferin and not containing phenol red. After incubation for 1 hour, bioluminescence was measured. In an experiment in FIG. 4c, from immediately after transfection, the sample was incubated under the condition of 37° C. and 5% $CO_2$ while blue light was continuously irradiated. After one hour, bioluminescence was measured at the depicted time point, while the sample was continuously irradiated with blue light, or the sample was placed in a dark place.

<Result>

Development of paCas9

First, Cas9 which is cut at a variety of sites was designed, and each of an N-terminal side fragment and a C-terminal side fragment of each pair was fused with FKBP or FRB of the heterodimerization-inducing system FKBP-FRB (DeRose, R. et al. Pflugers Arch. 465, 409-417 (2013).) using rapamycin (FIG. 5). Any cutting sites were positioned at a loop region to be exposed to a solution. The nuclease activity was measured by the luciferase reporter plasmid HDR assay, in the presence of rapamycin (FIG. 1b). In this assay, when a luciferase reporter which is driven with a CMV promoter having an in frame stop codon (StopFluc-1) is cut with divided Cas9, homologous recombination with a luciferase donor vector without a promoter is generated, and expression of full length luciferase is recovered. In HEK293T cells, the reporter activity was observed in almost all of N-terminal fragments and C-terminal fragments, and significant increase in the rapamycin-inducing reporter activity was exhibited in 8 pairs of the N-terminal fragment and the C-terminal fragment (FIG. 6). In a later experiment, an N-terminal fragment comprising 2 to 713 residues of Cas9 (hereinafter, referred to as "N713") and a C-terminal fragment comprising 714 to 1368 residues (hereinafter, referred to as "C714") were used.

Then, N713 and C714 were fused to each of light-dependent dimer forming domains (FIG. 1c). As the light-dependent dimer forming domain, first, the CRY2-CIB1 system was used. CRY2-CIB1 is based on blue light-dependent protein interaction between cryptochrome 2 (CRY2) of *Arabidopsis thaliana* and its binding partner CIB1 (Kennedy, M. J. et al. Nat. Methods 7, 973-975 (2010).). This system is widely used in optogenetic control of protein-protein interaction in a mammal cell. Then, N713 and C714 were fused with a photolyase homology region of CRY2 (CRY2 PHR) and CIB1, and the Cas9 activity inducing ability thereof was investigated by the luciferase plasmid HDR assay. However, in this system, light-dependent induction of the Cas9 activity was not seen. The reason thereof is thought that divided Cas9 was not rearranged well due to steric hindrance of large molecules of CRY2 PHR (498 amino acids) and CIB1 (335 amino acids). Another reason is thought that oligomer formation property of CRY2 PHR inhibited 1:1 interaction between N713 and C714 (Bugaj, L. J. et al. Nat. Methods 10, 249-252 (2013).).

Accordingly, then, the light-dependent dimer formation system "Magnet" (Kawano, 2015) which has been recently developed by the present inventors was used. The Magnet system is composed of a pair of light switch proteins named positive Magnet (pMag) and negative Magnet (nMag). When blue light is irradiated, pMag and nMag form a heterodimer. In contrast with CRY2-CIB1, pMag and nMag are 150 amino acids, and are as small as FKBP (107 amino acids) and FRB (93 amino acids). The dynamic range of a dissociation rate of the Magnet system can be regulated by introducing mutation into pMag and/or nMag. In the present Example, a combination of pMag and nMagHigh1 was used as the Magnet. The nMagHigh1 is nMag having M135I mutation and M165I mutation (Kawano, 2015). When N713 and C714 were fused with each of the Magnet in order to investigate whether the Magnet can well rearrange Cas9 which has been divided by light irradiation or not, N713 and C714 which had been fused to pMag and nMagHigh1, respectively, exhibited the great Cas9 activity with dependence on light. Particularly, since in a combination of N713-pMag and nMagHigh1-C714, the 16.4 times activity was seen, and the background activity was lowest, in a later experiment, a pair of N713-pMag and nMagHigh1-C714 was used, and this pair was called paCas9-1 (FIG. 7).

PAM Requirement and DNA Target Specificity of paCas9

In order to investigate whether paCas9-1 recognizes PAM like full length Cas9 or not, a stop codon-inserted luciferase reporter having point mutation at NGG PAM was prepared (FIGS. 1d and 1e). When an experiment was performed with two kinds of luciferase reporters having an internal stop codon at different places (StopFluc-1 and StopFluc-2), it was confirmed that the Cas9-inducing activity of a luciferase reporter having PAM being not canonical is lower than the Cas9-inducing activity of a luciferase reporter having canonical PAM represented by NGG (N is A, T, C or G). Additionally, it was exhibited that there is no significant difference in the luciferase activity between paCas9-1 and full length Cas9. Further, specificity of paCas9-1 for a target DNA was assessed by the luciferase plasmid HDR assay (FIG. 1f). For doing this, a series of sgRNAs of StopFluc-1 having one base Watson-Crick transversion mutation was prepared. As a result, it was exhibited that there is no significant difference in DNA target specificity between paCas9-1 and full length Cas9. When this specificity assay was performed using further two reporters having an internal stop codon at different positions (StopFluc-2 and StopFluc-3) in order to further investigate DNA target specificity of paCas9-1, it was confirmed that DNA target specificity of paCas9-1 is comparable to that of full length Cas9 (FIGS. 1g and 1h). Consistent with the previous study, a pattern of sensitivity of short chain sgRNA-DNA mismatch was different depending on a target sequence (Hsu, P. D. et al. Nat. Biotechnol. 31, 827-832 (2013).; Mali, P. et al. Nat. Biotechnol. 31, 833-838 (2013).; Fu, Y. et al. Nat. Biotechnol. 31, 822-826 (2013).). From these experiments, it was seen that PAM requirement and target specificity of paCas9-1 are equivalent to those of full length Cas9.

Optogenetic Genome Editing

In order to verify that paCas9-1 can cut an endogenous genome gene locus of a target in a mammal cell with dependence on light, and induce indel mutation through non-homologous end joining (NHEJ), HEK293 cells were transfected with paCas9-1, and a sgRNA targeting a human CCR5 locus (FIG. 2a). And, the ability of paCas9-1 to induce indel mutation by light was quantitatively assessed using the mismatch-sensitive T7 endonuclease I cutting a hetero-double-stranded DNA which is formed by hybridization between a mutated DNA and a wild-type DNA (T7E1). In a dark place, the indel ratio of the cells which had been transfected with paCas9-1 targeting CCR5 was only 1.1%. However, when blue light was irradiated, the cells which had been transfected with paCas9-1 targeting CCR5 exhibited the significantly high indel ratio (20.5%) at a human CCR5 locus. The frequency of indel mutation which had been induced by paCas9-1 was about 60% of that of full length Cas9 (34.4%) (FIG. 2a). Indel mutation by paCas9-1 which had been generated in a target region of a human CCR5 locus was confirmed by the Sanger method sequencing. In order to search a possibility of generalization of optogenetic genome editing with paCas9-1 and a guide RNA (sgRNA), sgRNAs of 4 sites in three human genes (EMX1, VEGFA and AAVS1) were newly constructed. In all cases using respective sgRNAs, light-dependent indel mutation was seen (FIG. 2c). Additionally, analysis with time of indel mutation at an EMX1 locus which had been induced by paCas9-1 was performed (FIG. 8). As a result, the frequency of indel mutation became higher as the irradiation time of blue light became longer. In order to investigate whether paCas9-1 also induces indel mutation in other cell strains or not, paCas9-1, and a sgRNA targeting human EMX1 were transfected into HeLa cells (FIG. 9). As expected, light-dependent indel mutation at an EMX1 locus was also seen in HeLa cells. Further, whether paCas9-1 can induce indel mutation at a plurality of target sites or not was investigated (FIG. 2d). Using two sgRNAs targeting EMX1 and VEGFA at the same time, paCas9-1 induced indel mutation at human EMX1 and VEGFA loci with dependence on light. These results exhibited that paCas9-1 can multiply perform NHEJ-mediated indel mutation-induced optogenetic control, extensively in a genome sequence of a mammal.

Then, whether paCas9-1 can be used in genome editing through HDR or not was investigated (FIGS. 2e and 2f). In this study, a single-stranded oligodeoxynucleotide (ssODN) was used as a donor template. HEK293T cells were transfected with paCas9-1 targeting EMX1, and ssODN containing a HindIII site, and the frequency of HDR at an EMX1 locus was analyzed by restriction fragment length polymorphism (RFLP) analysis. As a result, it was confirmed that paCas9-1 can induce integration of a HindIII site into a human EMX1 locus at the frequency of 7.2%. This result exhibited that paCas9-1 can not only induce random indel mutation, but also induce designed alteration at a genome sequence through HDR, with dependence on light.

The paired nicking method using a Cas9 D10A mutant which does not cut a double strand, but nicks a target DNA, in order to reduce the off-target activity of Cas9, has been proposed (Ran, F. A. et al. Cell 154, 1380-1389 (2013).). In order to investigate whether paCas9-1 can also be converted into a photoactivatable nickase or not, paCas9-1 containing D10A mutation (paCas9 nickase) was prepared (FIG. 10). A paCas9 nickase and a sgRNA targeting one strand of EMX1 did not induce indel mutation in a human EMX1 locuexhibitever, when a pair of sgRNAs targeting an opposing strand of an EMX1 site was used, a paCas9 nickase generated light-dependent indel mutation. This result exhibited that a paCas9 nickase can also be utilized in a Cas9-mediated double nicking method for reducing off-target genome alteration.

Reduction in the Background Activity of paCas9 paCas9-1 sufficiently induced NHEJ-mediated indel mutation, and also exhibited the background activity slightly under the dark condition (FIGS. 2a and 2c). In order to reduce the background activity of paCas9-1, attention was paid to the regulatable dynamic range of the Magnet. Since the background activity was lower in a combination of pMag and nMag than in a combination of pMag and nMagHigh1 (Kawano, 2015), nMag was used in place of nMagHigh1. And, HEK293T cells were transfected with a pair of N713-pMag and nMag-C714 targeting a VEGFA locus (hereinafter, referred to as "paCas9-2") and a sgRNA, and induction of indel mutation under the bright condition and under the dark condition was measured (FIG. 3a). The indel mutation under the dark condition with paCas9-2 was reduced to the level which cannot be detected by the T7E1 assay. The induction frequency of light-dependent indel mutation with paCas9-2 was unchanged from that with paCas9-1 (FIG. 3b). Then, in a later experiment, paCas9-2 was used.

Spatial and Temporary Control of paCas9

Then, whether the Cas9 nuclease activity can be controlled by paCas9 spatially or not was investigated (FIGS. 3c, 3d and FIG. 11). In order to visualize indel mutation by Cas9-inducing NHEJ in live cells, the surrogate EGFP reporter system which expresses EGFP fluorescence when double strand cutting is introduced into a target sequence by Cas9 was used (Kim, H. et al. Nat. Methods 8, 941-943 (2011).; Ramakrishna, S. et al. Nat. Commun. 5, 3378 (2014).). HKE293T cells which had been transfected with paCas9-2, a surrogate EGFP reporter and a sgRNA targeting a reporter were irradiated with slit pattern blue light. After 24 hours, slit pattern EGFP expression was observed, and it was exhibited that paCas9-2 can spatially control gene editing by light. Additionally, whether activation of paCas9 is reversible or not was also investigated (FIGS. 3e, f). For doing this, first, HEK293T cells were transfected with paCas9-2 and a sgRNA targeting VEGFA, and incubated by irradiating blue light, in order to activate paCas9-2. After 6 hours, the incubated cells were divided into two, placed in a dark place or a bright plate, and secondarily transfected with a sgRNA targeting EMX1. The sample was placed in a dark place or a bright place until immediately before second transfection, and after transfection, the sample was placed in a dark place or a bright place again, respectively. After incubation, a genomic DNA was isolated, and analyzed by the T7E1 assay. In the cells which had been irradiated with blue light after first transfection with paCas9-2 and a sgRNA targeting VDGFA, indel mutation was seen at a VEGFA locus, and it was exhibited that paCas9-2 was activated with blue light. In the cells which had been continuously irradiated with blue light after second transfection using a sgRNA targeting EMX1, indel mutation was seen at an EMX1 locus. However, in the cells which had been transferred to a dark place, indel mutation at an EMX1 locus was not generated. This result exhibits that the activity of paCas9-2 is switched off by extinguishing blue light, that is, the nuclease activity of Cas9 can be reversibly controlled.

Reversible Control of RNA-Induced Transcription Interference

In order to further exhibit reversibility of paCas9, photo-activatable reversible control of RNA-induced transcription interference was tried. This was named photoactivation-type CRISPR interference after the previous CRISPR interference using dCas9 (Qi, L. S. et al. Cell 152, 1173-1183 (2013).; Gilbert, L. a et al. Cell 154, 442-451 (2013).). For doing this, paCas9-2 having mutations of D10A and H840A (padCas9) was prepared (FIG. 4a). Additionally, sgRNAs targeting different three regions of a CMV promoter-driving luciferase promoter containing PEST and a mRNA destabilized sequence (Voon, 2005) was designed. padCas9, and each sgRNA targeting a luciferase reporter suppressed the luciferase reporter activity with dependence on light (FIG. 4b). Thereby, it was exhibited that a paCas9 platform can also optogenetically control RNA-induced transcription interference.

Then, whether padCas9-madiated gene expression suppression can be switched off by stopping light irradiation or not was investigated (FIG. 4c). After light irradiation was stopped, the reporter activity was gradually recovered, and it was exhibited that padCas9 is reversible.

From the foregoing, it was exhibited that paCas9 can spatially, temporally and reversibly control genome editing and transcription control with a guide RNA.

In conclusion, the present inventors succeeded in development of photoactivatable Cas9. In a first experiment, rapamycin-induced Cas9 activation was attained with many Cas9 pairs (FIGS. 5, 6). We further converted rapamycin-induced Cas9 into paCas9 which is photoactivatable Cas9. For doing this, first, the CRY2-CIB1 system which is the most frequently used photoinduced dimerization system was used, but optogenetic control of the Cas9 nuclease activity could not be performed. However, when the Magnet system developed by the present inventors was used, optogenetic control of Cas9 became possible, and further, succeeded in development of paCas9-2 which can optogenetically control the Cas9 activity, and is reduced in the background activity. Furthermore, it was exhibited that paCas9 activation can also be controlled spatially, and can be precisely switched on/off. According to the present invention, there was provided a first optogenetic tool which can control the Cas9 activity spatially and temporally. Additionally, it was verified that PAM requirement and target specificity of divided Cas9 are the same as those of full length Cas9. Like full length Cas9, paCas9 could be applied to multiple indel mutation being HDR-meditated genome editing, nick formation in a DNA double strand, and transcription control. A nature of spatially, temporally and reversibly controllable paCas9 is suitable for application to disconnection of the function of a causative gene in a variety of biological processes and medical care, such as in vivo and ex vivo gene therapy. Additionally, paCas9 can reduce the off-target indel frequency in genome editing using Cas9. Since paCas9 can be switched off by stopping light irradiation, there is a possibility that off-target gene modification can be decreased, by controlling the activation time of paCas9 with light. This paCas9 platform can be further applied to CRISPR-Cas9. For example, in vivo use of Cas9 was limited by limitation of the package size of a virus vector. Since a cDNA which is a constituent element of paCas9 of the present invention is shorter than full length Cas9, it also becomes possible to package each fragment of paCas9 into a virus vector with limited size, and thereby, application of in vivo genome editing can be expanded. Additionally, by expressing each constituent element of paCas9 using two different tissue-specific promoters, it becomes possible to control the Cas9 activity by the activity of two promoters and light, and further, it is though that further ultra high precision gene editing becomes possible.

Preparation of Plasmid cDNAs encoding an N-terminal fragment and a C-terminal fragment of Cas9 derived from *Streptococcus pyogenes* in which codons had been optimized were prepared based on a plasmid (#42230) obtained from Addgene. In order to delete the nuclease activity of Cas9, D10A mutation was introduced into an N-terminal fragment of Cas9 by using the Multi Site-Directed Mutagenesis Kit (by MBL) according to a manual, and H840A mutation was introduced into a C-terminal fragment of Cas9. cDNAs encoding light switch proteins (pMag, nMagHigh1, nMag) were prepared according to a reference literature (Kawano, 2015). During amplification of pMag, nMagHigh1 and nMag by standard PCR, a linker composed of glycine and serine was added to a 5'-terminus and a 3'-terminus of them (FIGS. 18, 22, 23). A construct in which Cas9 N/C fragments and light switch proteins (pMag, nMagHigh1, nMag) and VP64 are ligated and the nuclease activity was deleted in this way, was introduced into a pcDNA3.1 V5/His-A vector having a CMV promoter (by Invitrogen) and a pCAGGS vector having a CAG promoter (by RIKEN Bio Resource Center, RDB08938).

Preparation of MS2 Effector cDNA encoding MS2 and p65-HSF1 were used after amplification from plasmids (#27122 and #61423, respectively) obtained from Addgene. During amplification of MS2 by standard PCR, a linker composed of glycine and serine and a nuclear-localized signal sequence were added to a 5'-terminus and a 3'-terminus (FIGS. 18, 24). The thus prepared NLS-MS2-NLS-p65-HSF1 was introduced into the pcDNA3.1 V5/His-A vector.

Preparation of a Guide RNA (sgRNA)

For expression of a sgRNA in a mammal cell, the pSPgRNA vector (Addgene plasmid #47108) was used. A sgRNA with an MS2-binding sequence introduced therein (called sgRNA 2.0) was amplified with the Addgene plasmid (#61424), and was used by introduction into the pSPgRNA vector. A sgRNA with a PP7-binding sequence introduced therein (called sgRNA 2.0-PP7) was uniquely prepared (FIG. 20), and used by introduction into the pSPgRNA vector. sgRNAs targeting ASCL1, IL1R2 and NEUROD1, respectively, were prepared by introducing an oligo DNA into a BbsI site of the pSPgRNA vector. Nucleoside sequences of them are as follows:

```
                                    (SEQ ID NO: 267)
ASCL1;  GCAGCCGCTCGCTGCAGCAG (SEQ ID NO: 268)
IL1R2;  GACCCAGCACTGCAGCCTGG (SEQ ID NO: 269)
NEUROD1; GGGGAGCGGTTGTCGGAGGA
```

Culturing of HEK293T Cells

HEK293T cells (by ATCC) were cultured under the condition of 37° C. and 5% $CO_2$ using Dulbecco's Modified Eagle Medium (DMEM, by Sigma Aldrich) to which 10% FBS (HyClone), 100 unit/ml penicillin and 100 µg/ml streptomycin (GIBCO) had been added.

Light Manipulation of Gene Expression in HEK293T Cells

HEK293T cells were seeded on a 96-well plate (by Thermo Scientific) at the density of $2.0 \times 10^4$ cells/well, and cultured under the condition of 37° C. and 5% $CO_2$ for 24 hours. Gene introduction into HEK293T cells was performed using Lipofectamine 3000 (by Thermo Scientific) according to a manual. The cells were transfected with vectors encoding pCMV-NES-N713d-pMag-NES, pCMV-nMagHigh1-C714d-NLS-VP64, pCMV-NLS-MS2-NLS-p65-HSF1 (FIGS. 22 to 24) and a sgRNA, respectively, at the ratio of 1:1:1:1 (FIG. 19). The cells were transfected with plasmids encoding pCMV-dCas9-CIB1 (or pCMV-CIB1-dCas9-CIB1), pCMV-CRY2-p65 (or pCMV-CRY2FL-VP64) and a sgRNA at the ratio of 2:1:1 (FIG. 19). The cells were transfected with pCMV-dCas9-VP64 and a sgRNA at the ratio of 3:1 (FIG. 19). The cells were transfected with pCMV-dCas9-VP64, pCMV-MS2-NLS-p65-HSF1 and a sgRNA at the ratio of 2:1:1 (FIG. 19). In addition, in any cases, a total amount of a plasmid used in transfection is 0.1 µg/well. Twenty four hours after transfection, the sample was cultured under blue light irradiation, or in a dark place. Twenty four hours after initiation of blue light irradiation, a total RNA was extracted, and subjected to quantitative real time PCR analysis.

Quantitative Real Time PCR Analysis

A total RNA was extracted using the Cells-to-Ct kit (by Thermo Fisher Scientific) according to a manual. Quantitative real time PCR analysis was performed using the StepOnePlus system (by Thermo Fisher Scientific) and the TaqMan Gene Expression Master Mix (by Thermo Fisher Scientific) according to a manual. As TaqMan probes for detecting respective target genes and endogenous-controlled GAPDH, the following probes were used (Life technologies, TaqMan Gene Expression Assay ID is as follows: ASCL1; Hs04187546_g1, IL1R2; Hs01030384_m1, NEUROD1; Hs01922995_s1). The relative mRNA level of each sample with respect to a negative control (obtained by treating cells with a vacant vector introduced therein in a dark place) was calculated by the standard $\Delta\Delta Ct$ method (FIGS. 19, 20).

Culturing of iPS Cells, Transfection, Differentiation into Nerve Cells by Blue Light Irradiation Human iPS cells (#454E2) were obtained from RIKEN Bio Resource Center, and cultured in an mTeSR1 medium (by Stemcell Technologies) using a 6-well culture plate (by Thermo Fisher Scientific) coated with Matrigel (by Corning, #354230). In order to introduce sgRNAs targeting pCAG-NES-N713d-pMag-NES, pCAG-nMagHigh1-C714d-NLS-VP64, pCAG-NLS-MS2dFG-NLS-p65-HSF1 and NEUROD1 into $1.0\times10^6$ iPS cells, the 4D-Nucleofector (utilizing CA-137 program by Lonza) and the P3 Primary Cell 4D-Nucleofector X Kit S (by Lonza) were used. The transfected cells were seeded on an 8-well chamber slide (by Thermo Scientific) coated with Matrigel, at the density of $2.5\times10^5$ cells/well, and cultured with an mTeSR1 medium containing 10 µM ROCK inhibitor (by WAKO). Six hours after transfection, the sample was cultured under blue light irradiation, or in a dark place. A new mTeSR1 medium containing 10 µM ROCK inhibitor (by WAKO) was added every day. After four days from initiation of blue light irradiation, analysis by a fluorescent antibody method and quantitative real time PCR analysis were performed.

Analysis of iPS Cells which were Differentiated into Nerve Cells by Light Irradiation, by a Fluorescent Antibody Method A sample was washed with PBS two times, and fixed with 4% paraformaldehyde (by WAKO) for 10 minutes, and thereafter, treated with PBS containing 0.2% Triton X-100 for 10 minutes. The sample was washed with PBS two times, blocked with 3% BSA and 10% FBS for 1 hour, and stained with the anti-beta III tubulin eFluor 660 conjugate (by eBioscience, catalog no. 5045-10, clone 2G10-TB3) for 3 hours. In addition, the anti-beta III tubulin eFluor 660 conjugate was used by diluting it with a blocking solution at 1:500. The sample was washed with PBS two times, and stained with the DAPI (by Thermo Scientific) for 10 minutes. The stained sample was fluorescently observed with a confocal laser scanning microscope (LSM710 by Carl Zeiss) mounted with an objection lens at magnification of 20 (FIG. 21).

Sequence Listing Free Text

SEQ ID No.: 1 represents an amino acid sequence of the Vivid protein.

SEQ ID No.: 2 represents a full length amino acid sequence of the Cas9 protein.

SEQ ID No.: 3 represents an amino acid sequence of a fused polypeptide (N713-pMag).

SEQ ID No.: 4 represents an amino acid sequence of a fused polypeptide (nMagHigh1-C714).

SEQ ID No.: 5 represents an amino acid sequence of a fused polypeptide (nMag-C714).

SEQ ID No.: 6 represents a DNA sequence of StopFluc-1.

SEQ ID No.: 7 represents a DNA sequence of StopFluc-2.

SEQ ID No.: 8 represents a DNA sequence of StopFluc-3.

SEQ ID No.: 9 represents an amino acid sequence of a fused polypeptide (dN713-pMag).

SEQ ID No.: 10 represents an amino acid sequence of a fused polypeptide (nMagHigh1-dC714-VP64).

SEQ ID No.: 11 represents an amino acid sequence of a fused polypeptide (MS2-p65-HSF1).

SEQ ID No.: 12 represents a DNA sequence of a luciferase reporter (StopFluc-1).

SEQ ID No.: 13 represents a DNA sequence of a luciferase reporter (StopFluc-2).

SEQ ID No.: 14 represents a DNA sequence of a sgRNA (StopFluc-1).

SEQ ID No.: 15 represents a DNA sequence of a sgRNA (StopFluc-2).

SEQ ID No.: 16 represents a DNA sequence of a sgRNA (StopFluc-3).

SEQ ID No.: 17 represents a DNA sequence of a sequence of a human CCR5 locus which was targeted by paCas9.

SEQ ID No.: 18 represents a DNA sequence of a 1 base deleted sequence of a human CCR5 locus which was targeted by paCas9.

SEQ ID No.: 19 represents a DNA sequence of 2 base deleted sequence of a human CCR5 locus which was targeted by paCas9.

SEQ ID No.: 20 represents a DNA sequence of a 4 base deleted sequence of a human CCR5 locus which was targeted by paCas9.

SEQ ID No.: 21 represents a DNA sequence of a 10 base deleted sequence of a human CCR5 locus which was targeted by paCas9.

SEQ ID No.: 22 represents a DNA sequence of a 13 base deleted sequence of a human CCR5 locus which was targeted by paCas9.

SEQ ID No.: 23 represents a DNA sequence of a 14 base deleted sequence of a human CCR5 locus which was targeted by paCas9.

SEQ ID No.: 24 represents a DNA sequence (5'→3') of a human EMX1 locus which was targeted by paCas9.

SEQ ID No.: 25 represents a DNA sequence (3'→5') of a human EMX1 locus which was targeted by paCas9.

SEQ ID No.: 26 represents a DNA sequence of an ssODN donor template.

SEQ ID No.: 27 represents a DNA sequence (5'→3') of a human EMX1 locus which was targeted by a paCas9 nickase.

SEQ ID No.: 28 represents a DNA sequence (3'→5') of a human EMX1 locus which was targeted by a paCas9 nickase.

What is claimed is:

1. A set of two protein fragments selected from the group consisting of:
   a) an N-terminal fragment comprising amino acids 1-230 in an amino acid sequence of SEQ ID NO: 2, and a C-terminal fragment comprising amino acids 231-1368 of SEQ ID NO: 2,
   b) an N-terminal fragment comprising amino acids 1-257 in an amino acid sequence of SEQ ID NO: 2, and a C-terminal fragment comprising amino acids 258-1368 of SEQ ID NO: 2,
   c) an N-terminal fragment comprising amino acids 1-384 in an amino acid sequence of SEQ ID NO: 2, and a C-terminal fragment comprising amino acids 385-1368 of SEQ ID NO: 2,
   d) an N-terminal fragment comprising amino acids 1-532 in an amino acid sequence of SEQ ID NO: 2, and a C-terminal fragment comprising amino acids 533-1368 of SEQ ID NO: 2,
   e) an N-terminal fragment comprising amino acids 1-574 in an amino acid sequence of SEQ ID NO: 2, and a C-terminal fragment comprising amino acids 575-1368 of SEQ ID NO: 2,
   f) an N-terminal fragment comprising amino acids 1-640 in an amino acid sequence of SEQ ID NO: 2, and a C-terminal fragment comprising amino acids 641-1368 of SEQ ID NO: 2,
   g) an N-terminal fragment comprising amino acids 1-672 in an amino acid sequence of SEQ ID NO: 2, and a C-terminal fragment comprising amino acids 673-1368 of SEQ ID NO: 2,
   h) an N-terminal fragment comprising amino acids 1-687 in an amino acid sequence of SEQ ID NO: 2, and a C-terminal fragment comprising amino acids 688-1368 of SEQ ID NO: 2,
   i) an N-terminal fragment comprising amino acids 2-713 in an amino acid sequence of SEQ ID NO: 2, and a C-terminal fragment comprising amino acids 714-1368 of SEQ ID NO: 2,
   j) an N-terminal fragment comprising amino acids 1-940 in an amino acid sequence of SEQ ID NO: 2, and a C-terminal fragment comprising amino acids 941-1368,
   k) an N-terminal fragment comprising amino acids 1-1048 in an amino acid sequence of SEQ ID NO: 2, and a C-terminal fragment comprising amino acids 1049-1368 of SEQ ID NO: 2;
   l) an N-terminal fragment comprising amino acids 1-711 in an amino acid sequence of SEQ ID NO: 2, and a C-terminal fragment comprising amino acids 712-1368 of SEQ ID NO: 2;
   m) an N-terminal fragment comprising amino acids 1-712 in an amino acid sequence of SEQ ID NO: 2, and a C-terminal fragment comprising amino acids 713-1368 of SEQ ID NO: 2;
   n) an N-terminal fragment comprising amino acids 1-715 in an amino acid sequence of SEQ ID NO: 2, and a C-terminal fragment comprising amino acids 716-1368 of SEQ ID NO: 2;
   o) an N-terminal fragment comprising amino acids 1-716 in an amino acid sequence of SEQ ID NO: 2, and a C-terminal fragment comprising amino acids 717-1368 of SEQ ID NO: 2;
   p) an N-terminal fragment comprising amino acids 1-717 in an amino acid sequence of SEQ ID NO: 2, and a C-terminal fragment comprising amino acids 718-1368 of SEQ ID NO: 2;

q) an N-terminal fragment comprising amino acids 2-713 in an amino acid sequence of SEQ ID NO: 2, and a C-terminal fragment comprising amino acids 712-1368 of SEQ ID NO: 2;

r) an N-terminal fragment comprising amino acids 1-715 in an amino acid sequence of SEQ ID NO: 2, and a C-terminal fragment comprising amino acids 714-1368 of SEQ ID NO: 2;

s) an N-terminal fragment comprising amino acids 1-716 in an amino acid sequence of SEQ ID NO: 2, and a C-terminal fragment comprising amino acids 715-1368 of SEQ ID NO: 2;

t) an N-terminal fragment comprising amino acids 1-717 in an amino acid sequence of SEQ ID NO: 2, and a C-terminal fragment comprising amino acids 716-1368 of SEQ ID NO: 2;

u) an N-terminal fragment comprising amino acids 1-715 in an amino acid sequence of SEQ ID NO: 2, and a C-terminal fragment comprising amino acids 712-1368 of SEQ ID NO: 2;

v) an N-terminal fragment comprising amino acids 1-716 in an amino acid sequence of SEQ ID NO: 2, and a C-terminal fragment comprising amino acids 713-1368 of SEQ ID NO: 2;

w) an N-terminal fragment comprising amino acids 1-717 in an amino acid sequence of SEQ ID NO: 2, and a C-terminal fragment comprising amino acids 714-1368 of SEQ ID NO: 2; and x) an N-terminal fragment comprising amino acids 1-717 in an amino acid sequence of SEQ ID NO: 2, and a C-terminal fragment comprising amino acids 712-1368 of SEQ ID NO: 2; wherein the amino acid at position 10 may be substituted and/or the amino acid at position 840 may be substituted.

2. The set of two protein fragments according to claim 1, wherein the amino acid at position 10 is a D10A substitution.

3. A method of cutting a target double-stranded nucleic acid, which comprises incubating the target double-stranded nucleic acid with the set of protein fragments according to claim 2, and a guide RNA or a pair of guide RNAs which comprise a sequence complementary to a portion of a strand of the target double-stranded nucleic acid, wherein the target double-stranded nucleic acid is cut.

4. The set of two protein fragments according to claim 1, wherein the amino acid at position 840 is an H840 substitution.

5. A method of suppressing expression of a target gene, which comprises incubating the target gene with the set of protein fragments according to claim 4, and a guide RNA or a pair of guide RNAs which comprise a sequence complementary to a portion of the target gene, wherein expression of the target gene is suppressed.

6. The set of two protein fragments according to claim 1, the amino acid at position 10 is a D10A substitution and the amino acid at position 840 is an H840 substitution.

7. A method of activating expression of a target gene, which comprises incubating the target gene with the set of protein fragments according to claim 6, and a guide RNA or a pair of guide RNAs which comprise a sequence complementary to a portion of the target gene, wherein expression of the target gene is activated.

8. The set of two protein fragments according to claim 1, wherein the N-terminal fragment has a first polypeptide covalently attached thereto and the C-terminal fragment has a second polypeptide covalently attached thereto, wherein said first and second polypeptides are heterologous to SEQ ID NO: 2 and wherein said first and second polypeptides may be the same or different.

9. A nucleic acid encoding the set of protein fragments according to claim 8.

10. An expression vector comprising the nucleic acid according to claim 9.

11. A kit comprising the expression vector according to claim 10.

12. A kit comprising the nucleic acid according to claim 9.

13. A kit comprising the set of two protein fragments according to claim 8.

14. A nucleic acid encoding the set of protein fragments according to claim 1.

15. An expression vector comprising the nucleic acid according to claim 14.

16. A kit comprising the expression vector according to claim 15.

17. A kit comprising the nucleic acid according to claim 14.

18. A method of cutting a target double-stranded nucleic acid, which comprises incubating the target double-stranded nucleic acid with the set of protein fragments according to claim 1, and a guide RNA or a pair of guide RNAs which comprise a sequence complementary to a portion of a strand of the target double-stranded nucleic acid, wherein the target double-stranded nucleic acid is cut.

19. A kit comprising the set of two protein fragments according to claim 1.

* * * * *